US010529935B2

United States Patent
Lee et al.

(10) Patent No.: US 10,529,935 B2
(45) Date of Patent: Jan. 7, 2020

(54) ORGANOMETALLIC COMPOUND, ORGANIC LIGHT EMITTING DEVICE, AND COMPOSITION FOR DIAGNOSING INCLUDING ORGANOMETALLIC COMPOUND

(71) Applicant: SAMSUNG ELECTRONICS CO., LTD., Suwon-si, Gyeonggi-do (KR)

(72) Inventors: Jiyoun Lee, Seoul (KR); Yoonhyun Kwak, Seoul (KR); Ohyun Kwon, Seoul (KR); Sunyoung Lee, Seoul (KR); Hyeonho Choi, Seoul (KR); Jiwhan Kim, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 241 days.

(21) Appl. No.: 15/218,714

(22) Filed: Jul. 25, 2016

(65) Prior Publication Data

US 2017/0237022 A1    Aug. 17, 2017

(30) Foreign Application Priority Data

Feb. 11, 2016  (KR) .................. 10-2016-0015675

(51) Int. Cl.
*H01L 51/00* (2006.01)
*C09K 11/06* (2006.01)
*C07F 15/00* (2006.01)
*H01L 51/50* (2006.01)

(52) U.S. Cl.
CPC ...... *H01L 51/0087* (2013.01); *C07F 15/0086* (2013.01); *C09K 11/06* (2013.01); *H01L 51/0094* (2013.01); *C09K 2211/1007* (2013.01); *C09K 2211/1011* (2013.01); *C09K 2211/1044* (2013.01); *C09K 2211/185* (2013.01); *H01L 51/5016* (2013.01)

(58) Field of Classification Search
CPC combination set(s) only.
See application file for complete search history.

(56) References Cited

U.S. PATENT DOCUMENTS

| 8,389,725 B2 | 3/2013 | Li et al. |
|---|---|---|
| 8,962,838 B2 | 2/2015 | De Cola et al. |
| 2007/0296329 A1 | 12/2007 | Sotoyama et al. |
| 2011/0028723 A1* | 2/2011 | Li ...................... C07F 15/0086 546/4 |

FOREIGN PATENT DOCUMENTS

| JP | 2008-069268 A | 3/2008 |
|---|---|---|
| WO | 2012-117082 A1 | 9/2012 |

* cited by examiner

*Primary Examiner* — Jennifer A Chriss
*Assistant Examiner* — Sean M DeGuire
(74) *Attorney, Agent, or Firm* — Cantor Colburn LLP

(57) ABSTRACT

An organometallic compound represented by Formula 1:

$M(L_1)(L_2)$    Formula 1 wherein, in Formula 1, M, $L_1$, and $L_2$ are the same as described in the specification.

14 Claims, 1 Drawing Sheet

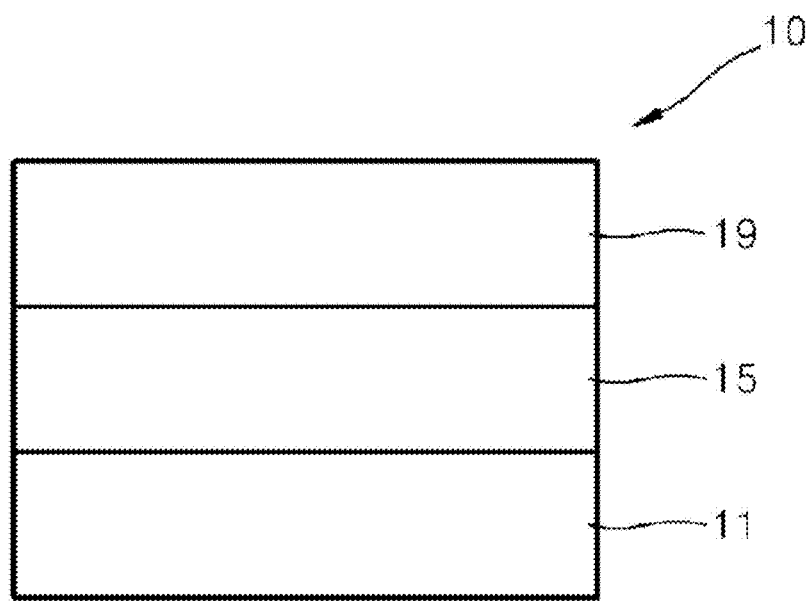

… (US 10,529,935 B2)

ORGANOMETALLIC COMPOUND, ORGANIC LIGHT EMITTING DEVICE, AND COMPOSITION FOR DIAGNOSING INCLUDING ORGANOMETALLIC COMPOUND

CROSS-REFERENCE TO RELATED APPLICATION

This application claims priority to Korean Patent Application No. 10-2016-0015675, filed on Feb. 11, 2016 in the Korean Intellectual Property Office, and all the benefits accruing therefrom under 35 U.S.C. § 119, the content of which is incorporated herein in its entirety by reference.

BACKGROUND

1. Field

The present disclosure relates to an organometallic compound, an organic light-emitting device including the organometallic compound, and a composition for diagnosing including the organometallic compound.

2. Description of the Related Art

Organic light-emitting devices (OLEDs) are self-emission devices, which have wide viewing angles, exhibit excellent driving voltage and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Further, light-emitting compounds, e.g., phosphorescent emitting compounds, can also be used in monitoring, sensing, or detecting of biological materials including a variety of cells and proteins.

Various types of organic light emitting devices are known. However, there still remains a need in OLEDs having low driving voltage, high efficiency, high brightness, and long lifespan.

SUMMARY

Provided are an organometallic compound, an organic light-emitting device including the organometallic compound, and a composition for diagnosing the organometallic compound.

Additional aspects will be set forth in part in the description which follows and, in part, will be apparent from the description, or may be learned by practice of the presented embodiments.

According an aspect of an embodiment, an organometallic compound is represented by Formula 1:

$M(L_1)(L_2)$   Formula 1

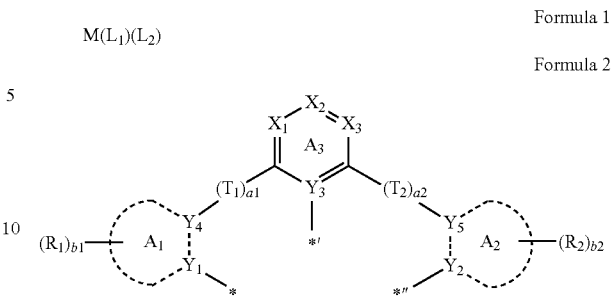

Formula 2 wherein, in Formulae 1 and 2,

M may be beryllium, magnesium, aluminum, calcium, titanium, manganese, cobalt, copper, zinc, gallium, germanium, zirconium, ruthenium, rhodium, palladium, silver, rhenium, gold, or platinum, $L_1$ may be selected from tridentate ligands represented by Formula 2, $L_2$ may be selected from monodentate organic ligands,

*, *', and *'' in Formula 2 may each indicate a binding site to M in Formula 1, $Y_1$ to $Y_3$ may each be nitrogen, $Y_4$ and $Y_5$ may each be carbon, $Y_1$ may be bound to $Y_4$ via a single or double bond, $Y_2$ may be bound to $Y_5$ via a single or double bond, provided that one selected from a bond between $Y_1$ and M, a bond between $Y_2$ and M, and a bond between ligand $L_2$ and M may be a coordinate bond, while the rest are each a covalent bond, a bond between $Y_3$ and M may be a coordinate bond, ring $A_1$ may be a 5-membered ring including at least one nitrogen as a ring-forming atom, ring $A_2$ may be a 6-membered ring including at least one nitrogen as a ring-forming atom, $X_1$ may be N or $C(R_3)$, $X_2$ may be N or $C(R_4)$, $X_3$ may be N or $C(R_5)$, at least two selected from $R_3$ to $R_5$ may optionally be bound to each other to form a substituted or unsubstituted $C_5$-$C_{30}$ carbocyclic group or a substituted or unsubstituted $C_2$-$C_{30}$ heterocyclic group, $T_1$ may be a group selected from a single bond, *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*, Si($R_6$)($R_7$)—*', and *—P($R_6$)($R_7$)—*', wherein * and *' in each of the foregoing groups independently indicate a binding site to a neighboring atom, $T_2$ may be a group selected from *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom, $R_6$ and $R_7$ may optionally be bound to each other to form a substituted or unsubstituted $C_5$-$C_{30}$ carbocyclic group or a substituted or unsubstituted $C_2$-$C_{30}$ heterocyclic group, a1 and a2 may be each independently an integer selected from 1 to 3, $R_1$ to $R_7$ may be each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), b1 and b2 may be each independently an integer selected from 0 to 3, and when b1 is 2 or greater, groups $R_1$ may be identical to or different from each other, and when b2 is 2 or greater, groups $R_2$ may be identical to or different from each other, two of the b1 number of groups $R_1$ may optionally be bound to each other to form a substituted or unsubstituted $C_5$-$C_{30}$ carbocyclic group or a substituted or unsubstituted $C_2$-$C_{30}$ heterocyclic group, two of the b2 number of groups $R_2$ may optionally be bound to each other to form a substituted or unsubstituted $C_5$-$C_{30}$ carbocyclic group or a substituted or unsubstituted $C_2$-$C_{30}$ heterocyclic group, at least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to an aspect of another embodiment, an organic light-emitting device includes:

a first electrode;

a second electrode; and an organic layer disposed between the first electrode and the second electrode, wherein the organic layer includes an emission layer and at least one organometallic compound described above.

In the emission layer, the organometallic compound may serve as a dopant.

According to an aspect of another embodiment, there is provided a composition for diagnosing that includes at least one organometallic compound represented by Formula 1.

BRIEF DESCRIPTION OF THE DRAWINGS

These and/or other aspects will become apparent and more readily appreciated from the following description of the embodiments, taken in conjunction with the accompanying drawings in which:

the FIGURE is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound is represented by Formula 1:

$$M(L_1)(L_2) \qquad \text{Formula 1}$$

wherein, in Formula 1, M may be beryllium, magnesium, aluminum, calcium, titanium, manganese, cobalt, copper, zinc, gallium, germanium, zirconium, ruthenium, rhodium, palladium, silver, rhenium, gold, or platinum (Pt). For example, in Formula 1, M may be platinum (Pt).

$L_1$ in Formula 1 may be selected from tridentate ligands represented by Formula 2, $L_2$ may be selected from monodentate organic ligands, and *, *', and *" in Formula 2 each indicate a binding site to M in Formula 1.

Formula 2

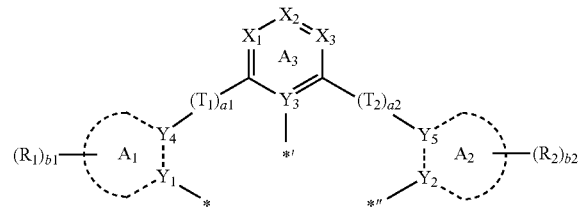

wherein, in Formula 2, $Y_1$ to $Y_3$ may each be nitrogen (N), $Y_4$ and $Y_5$ may each be carbon (C), a bond between $Y_1$ and $Y_4$ may be a single bond or double bond, and a bond between $Y_2$ and $Y_5$ may be a single bond or a double bond.

In Formula 2, a bond between $Y_1$ and M and a bond between ligand $L_2$ and M may each be a covalent bond, and a bond between $Y_3$ and M and a bond between $Y_2$ and M may each be a coordinate bond, a bond between $Y_1$ and M and a bond between $Y_2$ and M may each be a covalent bond, and a bond between $Y_3$ and M and a bond between ligand $L_2$ and M may each be a coordinate bond, or a bond between $Y_2$ and M and a bond between ligand $L_2$ and M may each be a covalent bond, and a bond between $Y_1$ and M and a bond between $Y_3$ and M may each be a coordinate bond.

Thus, the organometallic compound represented by Formula 1 may be electrically neutral, non-ionic compound having no charge.

Ring $A_1$ in Formula 2 may be a 5-membered ring including at least one nitrogen as a ring-forming atom, and ring $A_2$ may be a 6-membered ring including at least one nitrogen as a ring-forming atom.

According to an embodiment, ring $A_1$ in Formula 2 may be a 5-membered ring including at least two nitrogens as ring-forming atoms, but embodiments are not limited thereto.

In various embodiments, ring $A_1$ in Formula 2 may be selected from a pyrrole ring, a pyrazole ring, an imidazole ring, a triazole ring, a tetrazole ring, an oxazole ring, an isoxazole ring, a thiazole ring, an isothiazole ring, an oxadiazole ring, thiadiazole ring, a benzopyrazole ring, and a benzoimidazole ring.

According to some embodiments, ring $A_1$ in Formula 2 may be selected from a pyrazole ring, an imidazole ring, a triazole ring, a tetrazole ring, an oxadiazole ring, a thiadiazole ring, a benzopyrazole ring, and a benzoimidazole ring.

According to some embodiments, ring $A_2$ may be selected from a pyridine ring, a pyrimidine ring, a pyrazine ring, a pyridazine ring, a triazine ring, a quinoline ring, an isoquinoline ring, a quinoxaline ring, a quinazoline ring, and a phenanthroline ring.

According to some embodiments, in Formula 2, ring $A_1$ may be selected from a pyrazole ring, an imidazole ring, a triazole ring, a benzopyrazole ring, and a benzoimidazole ring, and ring $A_2$ may be selected from a pyridine ring, a pyrimidine ring, a quinoline ring, an isoquinoline ring, a quinoxaline ring, and a quinazoline ring, but embodiments are not limited thereto.

In Formula 2, $X_1$ may be N or $C(R_3)$, $X_2$ may be N or $C(R_4)$, and $X_3$ may be N or $C(R_5)$, wherein at least two of $R_3$ to $R_5$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted pentadiene group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, a substituted or unsubstituted naphthalene group, a substituted or unsubstituted anthracene group, a substituted or unsubstituted tetracene group, a substituted or unsubstituted phenanthrene group, a substituted or unsubstituted dihydronaphthalene group, a substituted or unsubstituted phenalene group, a substituted or unsubstituted benzothiophene group, a substituted or unsubstituted benzofuran group, a substituted or unsubstituted indene group, or a substituted or unsubstituted indole group).

Ring $A_3$ in Formula 2 may include one or two nitrogens as ring-forming atoms.

In Formula 2, $T_1$ may be a group selected from a single bond, *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom, and $T_2$ may be a group selected from *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom, wherein $R_6$ and $R_7$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted cyclopropane group, a substituted or unsubstituted cyclobutane group, a substituted or unsubstituted cyclopentane group, a substituted or unsubstituted cyclohexane group, a substituted or unsubstituted benzene group, or a substituted or unsubstituted naphthalene group). $R_6$ and $R_7$ are as provided herein.

a1 and a2 in Formula 1 may be each independently an integer selected from 1 to 3. a1 indicates the number of groups $T_1$, and when a1 is 2 or greater, groups $T_1$ may be identical to or different from each other, and a2 indicates the number of groups $T_2$, and when a2 is 2 or greater, groups $T_2$ may be identical to or different from each other. For example, a1 and a2 may be each independently 1 or 2.

A moiety in Formula 2 represented by

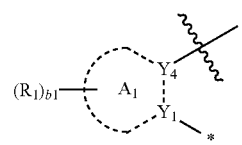

may be represented by one of Formulae 3-1 to 3-25, 3-31 to 3-74, and 3-81 to 3-92, a moiety in Formula 2 represented by

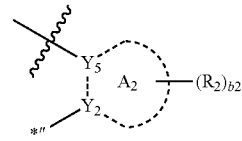

may be represented by one of Formulae 4-1 to 4-53, and a moiety in Formula 2 represented by

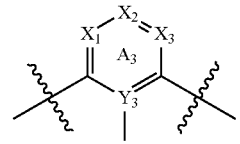

may be represented by one of Formulae 5-1 to 5-48:

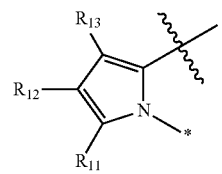

Formula 3-1

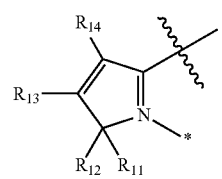

Formula 3-2

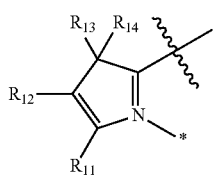
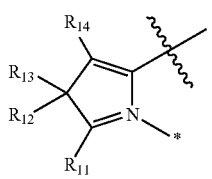
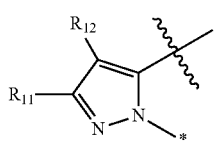
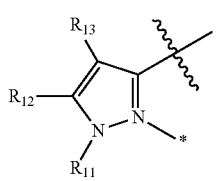
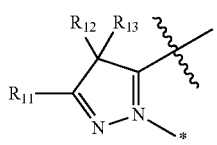
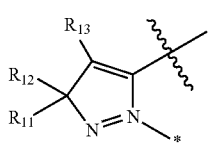
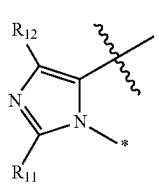
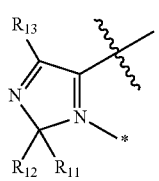
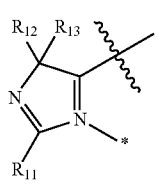
Formula 3-3
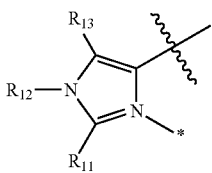
Formula 3-4
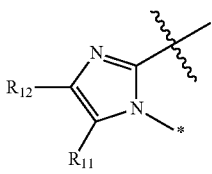
Formula 3-5
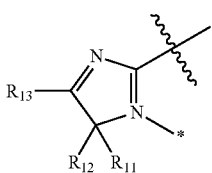
Formula 3-6
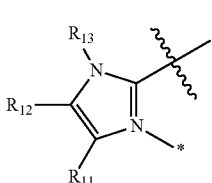
Formula 3-7
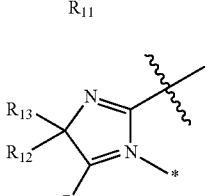
Formula 3-8
Formula 3-9
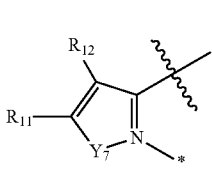
Formula 3-10
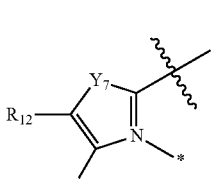
Formula 3-11
Formula 3-12
Formula 3-13
Formula 3-14
Formula 3-15
Formula 3-16
Formula 3-17
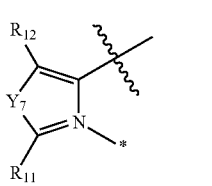
Formula 3-18
Formula 3-19
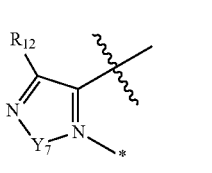
Formula 3-20

Formula 3-21
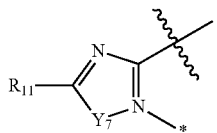
Formula 3-22
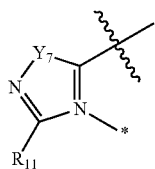
Formula 3-23
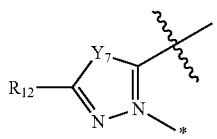
Formula 3-24
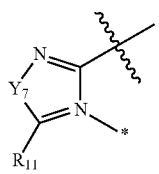
Formula 3-25
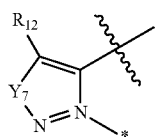
Formula 3-31
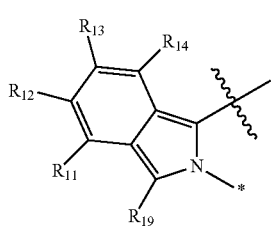
Formula 3-32
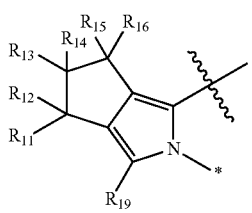
Formula 3-33
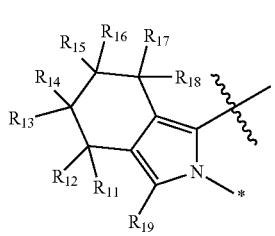
Formula 3-34
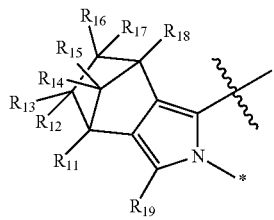
Formula 3-35
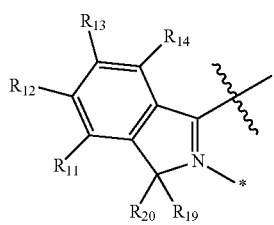
Formula 3-36

Formula 3-37
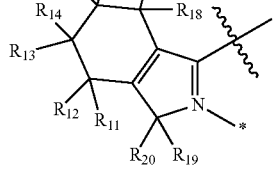
Formula 3-38
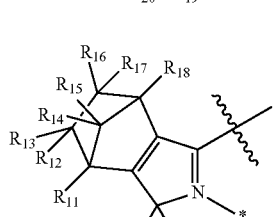
Formula 3-39
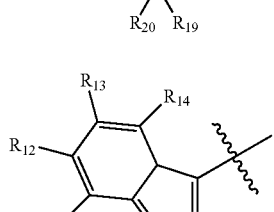
Formula 3-40
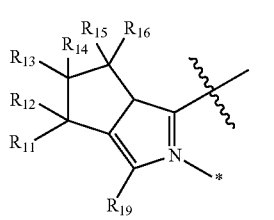

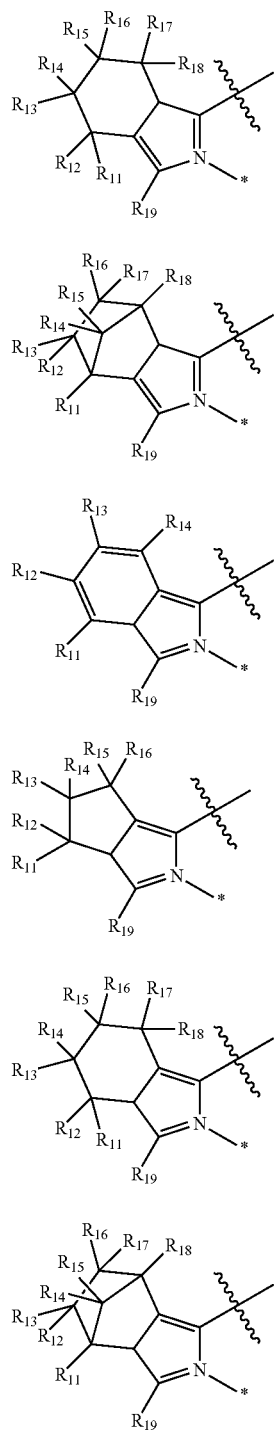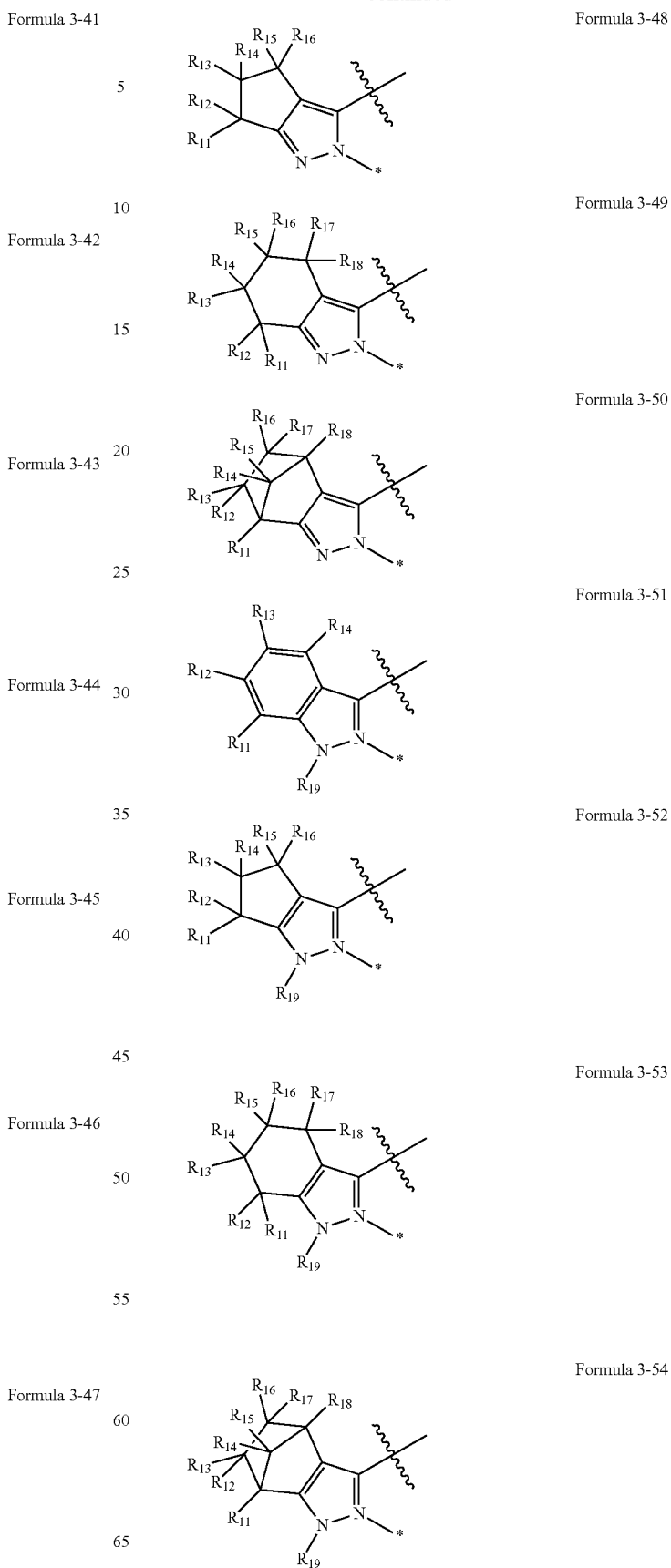

-continued
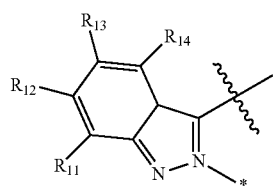
Formula 3-55
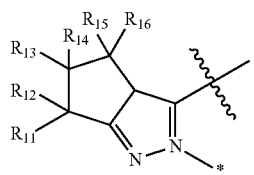
Formula 3-56
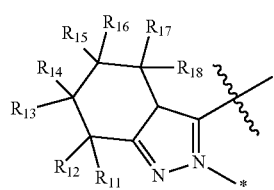
Formula 3-57
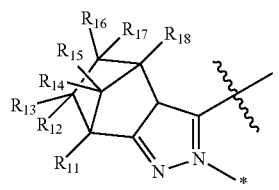
Formula 3-58
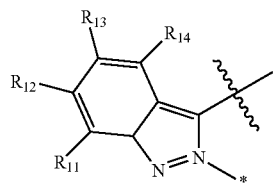
Formula 3-59
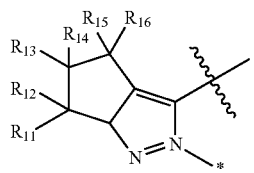
Formula 3-60
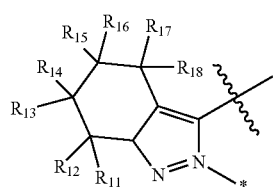
Formula 3-61
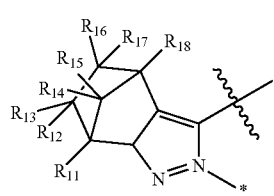
Formula 3-62
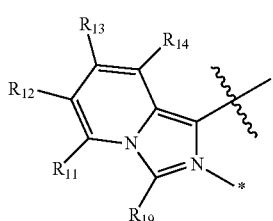
Formula 3-63
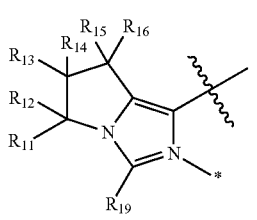
Formula 3-64
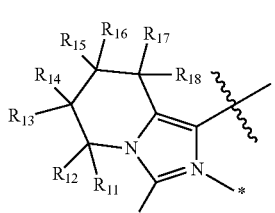
Formula 3-65
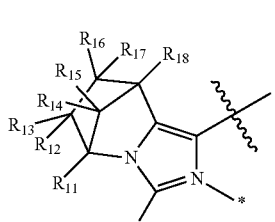
Formula 3-66
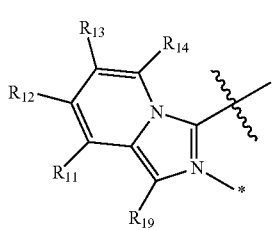
Formula 3-67
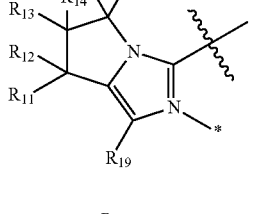
Formula 3-68
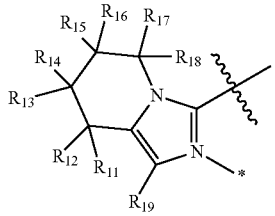
Formula 3-69

-continued
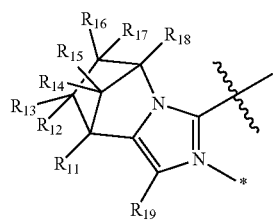
Formula 3-70
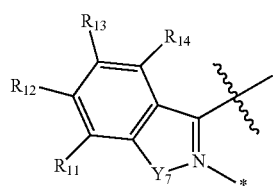
Formula 3-71
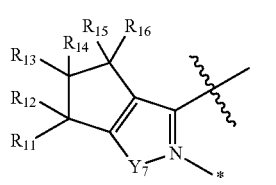
Formula 3-72
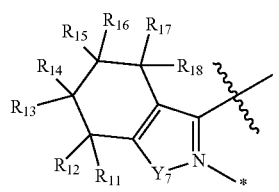
Formula 3-73
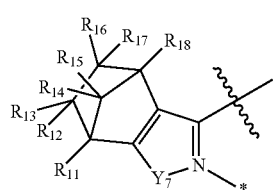
Formula 3-74
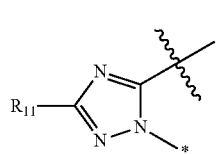
Formula 3-81
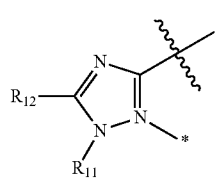
Formula 3-82
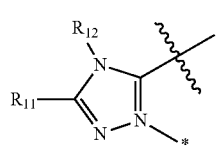
Formula 3-83
-continued
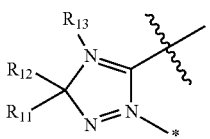
Formula 3-84
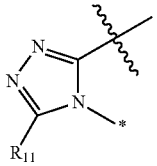
Formula 3-85
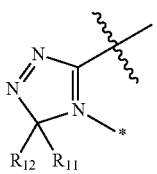
Formula 3-86
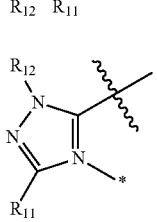
Formula 3-87
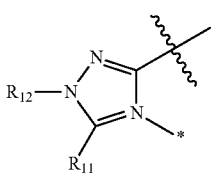
Formula 3-88
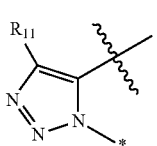
Formula 3-89
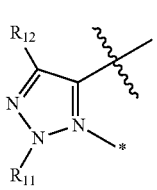
Formula 3-90
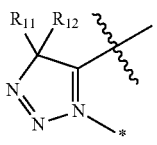
Formula 3-91
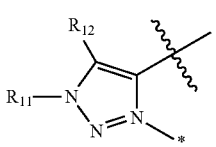
Formula 3-92

-continued
Formula 4-1
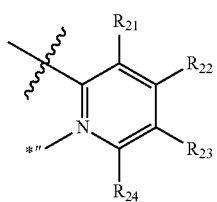
Formula 4-2
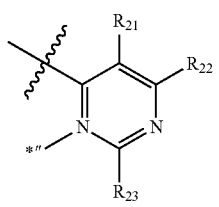
Formula 4-3
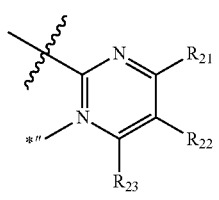
Formula 4-4
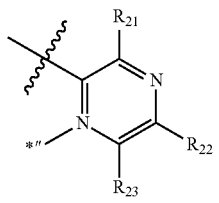
Formula 4-5
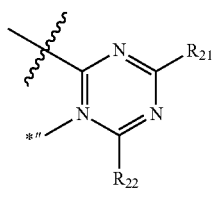
Formula 4-6
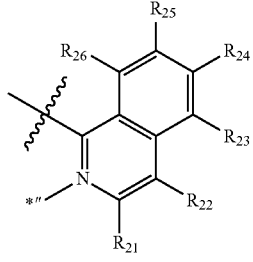
Formula 4-7
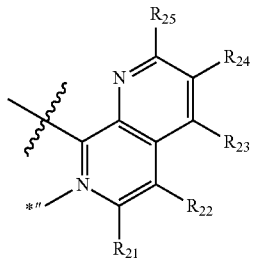
-continued
Formula 4-8
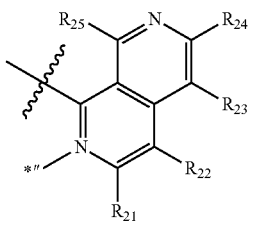
Formula 4-9
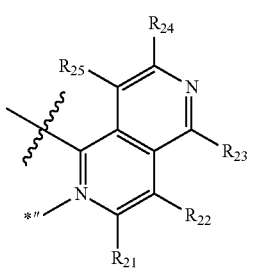
Formula 4-10
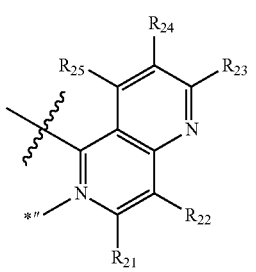
Formula 4-11
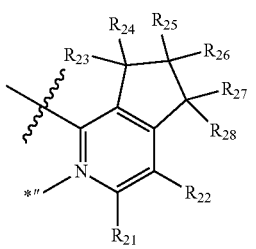
Formula 4-12
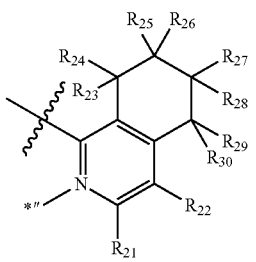
Formula 4-13
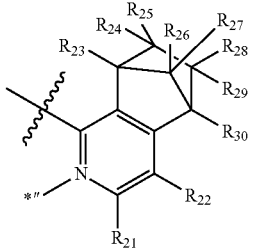

-continued
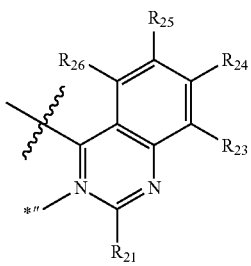
Formula 4-14
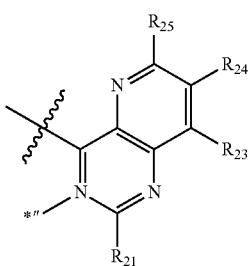
Formula 4-15
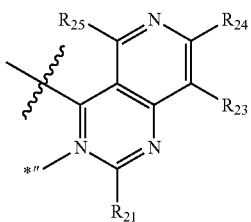
Formula 4-16
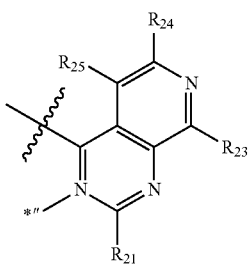
Formula 4-17
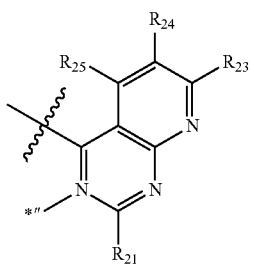
Formula 4-18
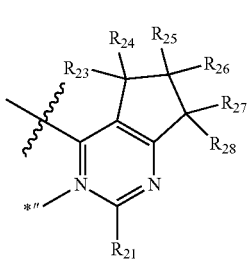
Formula 4-19
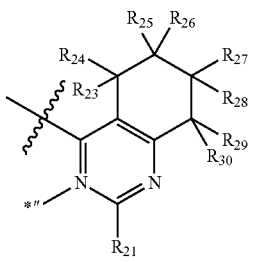
Formula 4-20
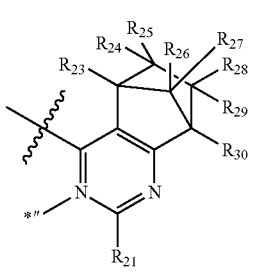
Formula 4-21
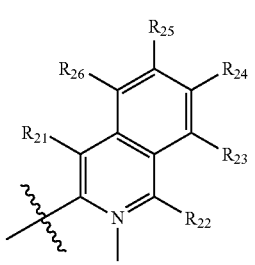
Formula 4-22
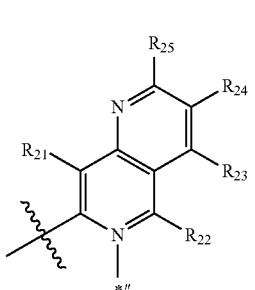
Formula 4-23
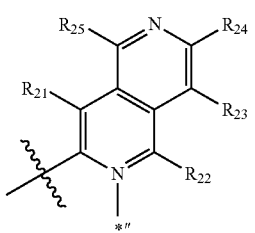
Formula 4-24
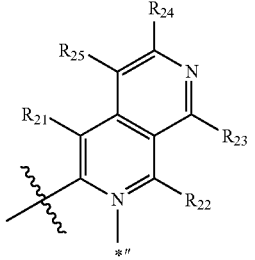
Formula 4-25

Formula 4-26
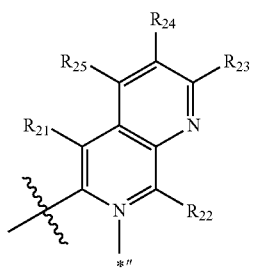
Formula 4-27
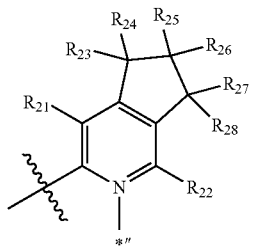
Formula 4-28
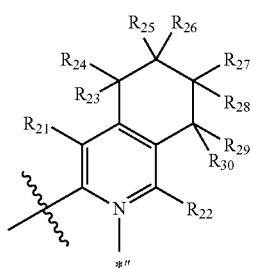
Formula 4-29
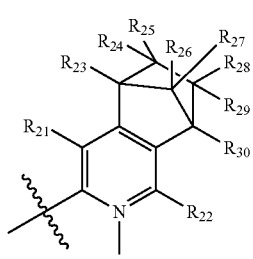
Formula 4-30
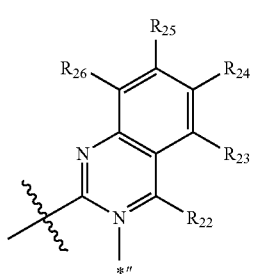
Formula 4-31
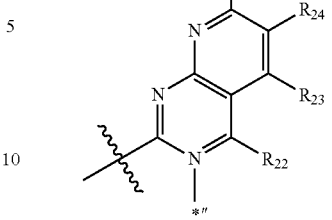
Formula 4-32
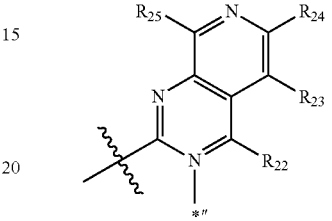
Formula 4-33
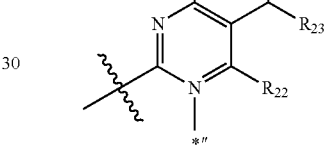
Formula 4-34
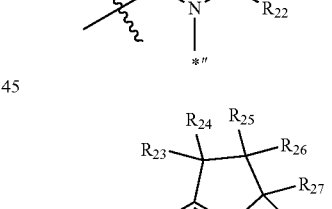
Formula 4-35
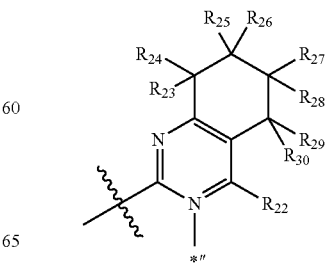
Formula 4-36
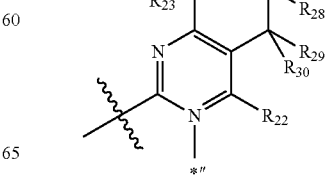

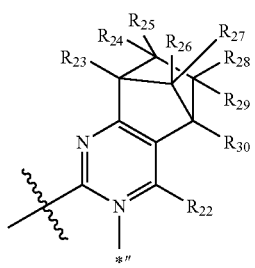
Formula 4-37
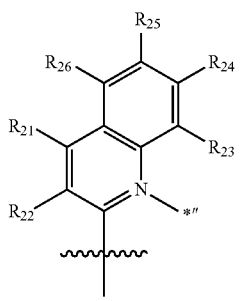
Formula 4-38
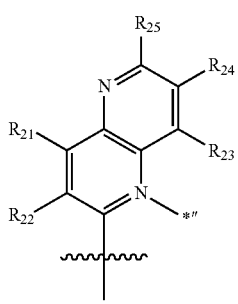
Formula 4-39
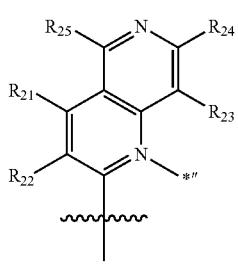
Formula 4-40
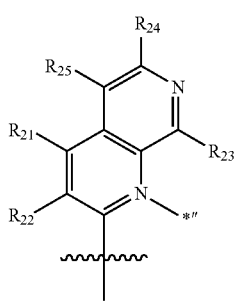
Formula 4-41
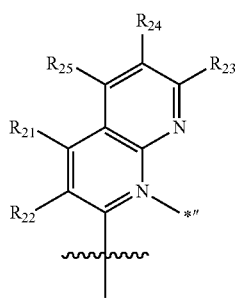
Formula 4-42
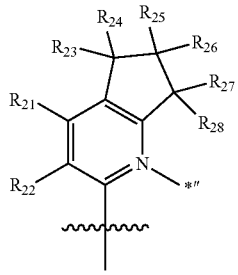
Formula 4-43
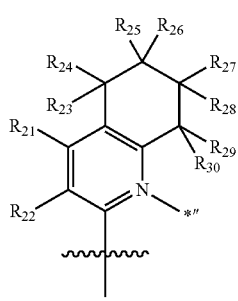
Formula 4-44
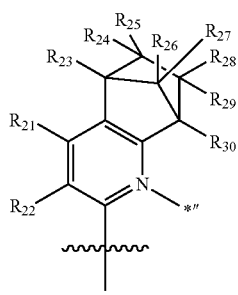
Formula 4-45
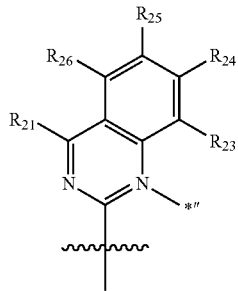
Formula 4-46

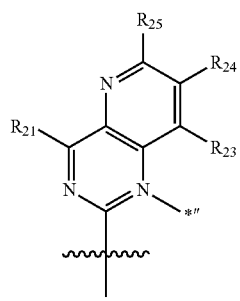
Formula 4-47
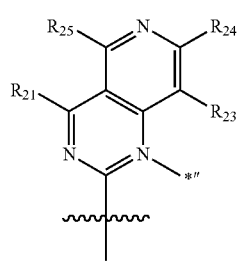
Formula 4-48
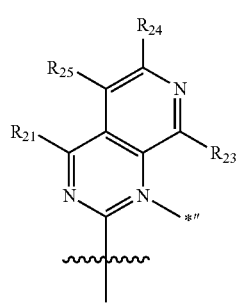
Formula 4-49
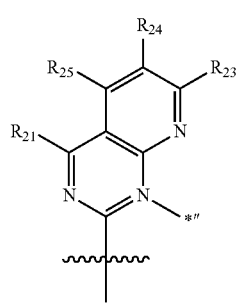
Formula 4-50
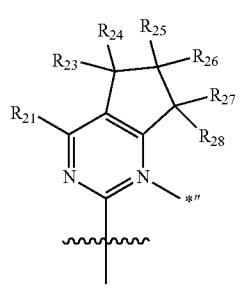
Formula 4-51
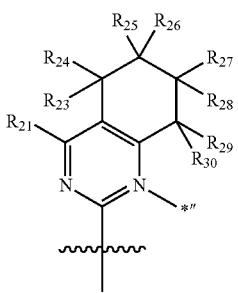
Formula 4-52
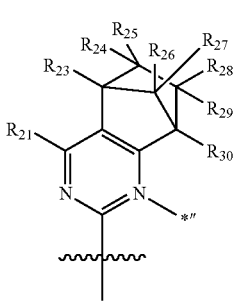
Formula 4-53
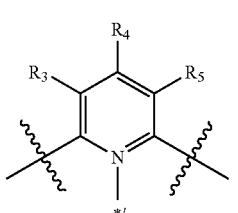
Formula 5-1
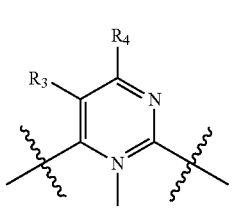
Formula 5-2
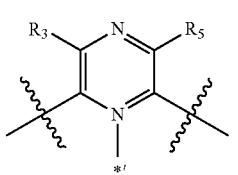
Formula 5-3
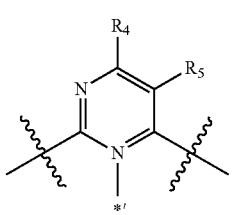
Formula 5-4

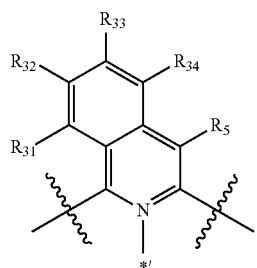
Formula 5-5
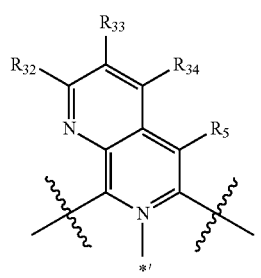
Formula 5-6
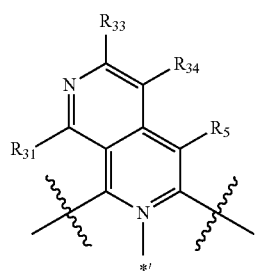
Formula 5-7
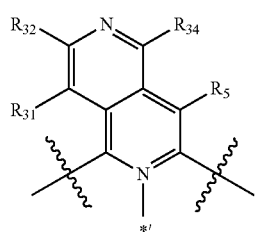
Formula 5-8
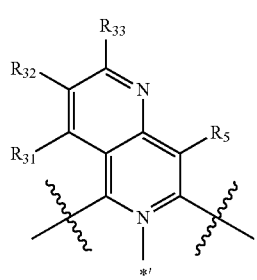
Formula 5-9
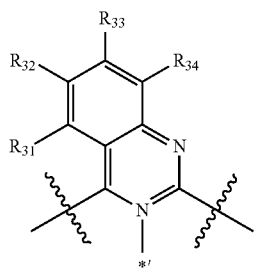
Formula 5-10
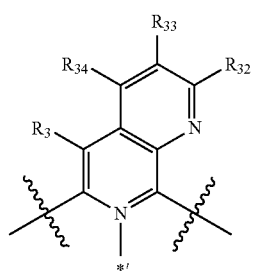
Formula 5-11
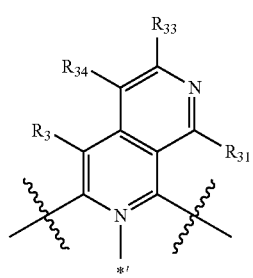
Formula 5-12
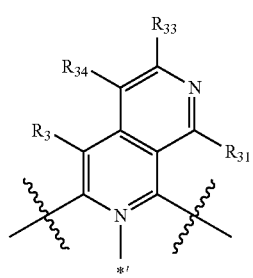
Formula 5-13
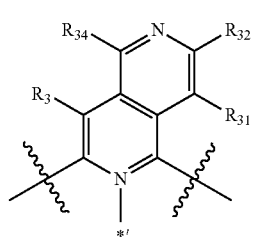
Formula 5-14

Formula 5-15
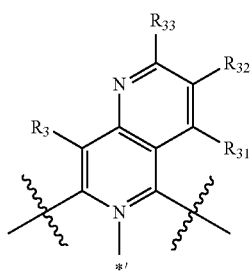
Formula 5-16
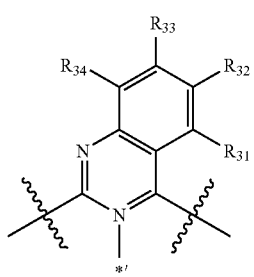
Formula 5-17
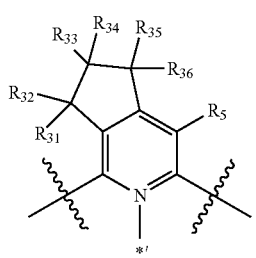
Formula 5-18
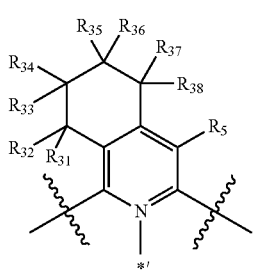
Formula 5-19
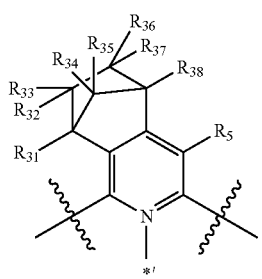
Formula 5-20
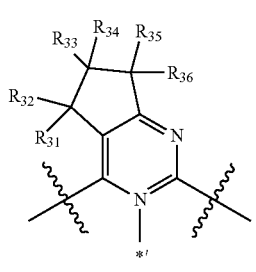
Formula 5-21
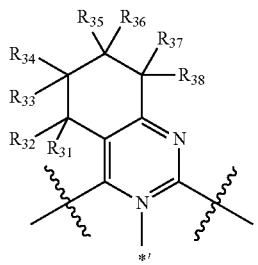
Formula 5-22
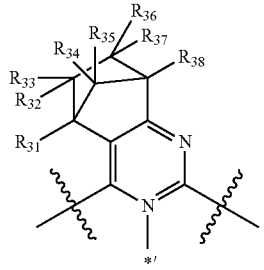
Formula 5-23
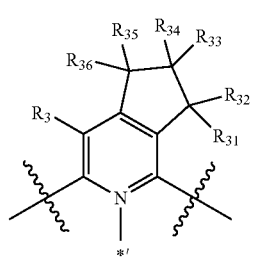
Formula 5-24
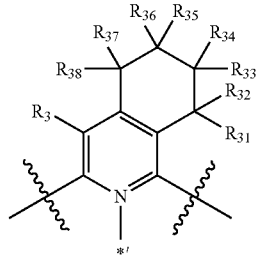
Formula 5-25
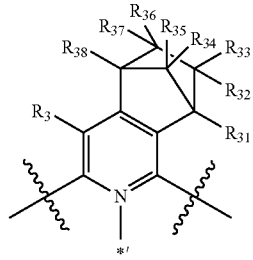
Formula 5-26
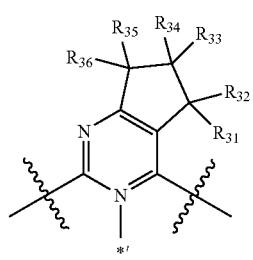

Formula 5-27
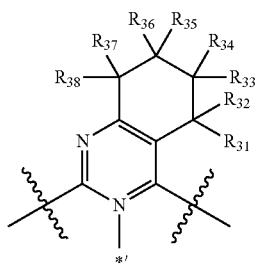
Formula 5-28
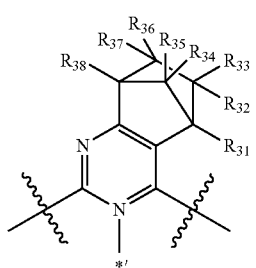
Formula 5-29
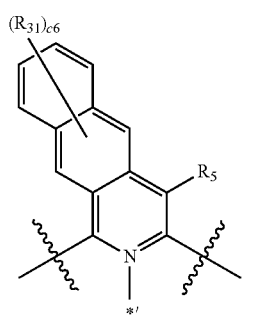
Formula 5-30
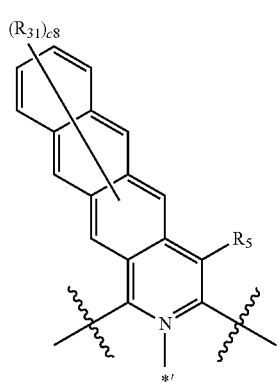
Formula 5-31
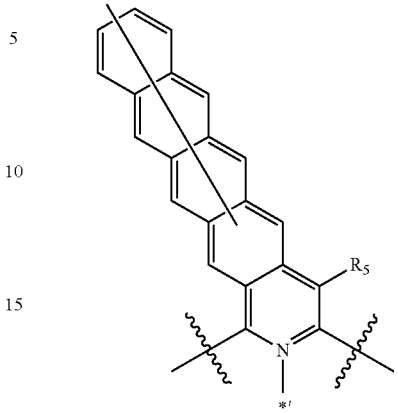
Formula 5-32
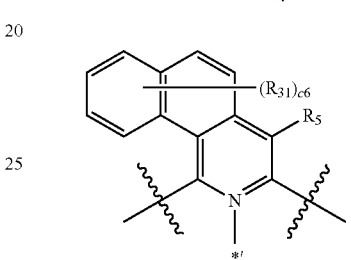
Formula 5-33
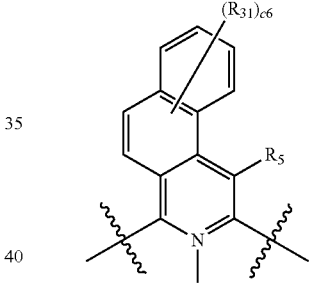
Formula 5-34
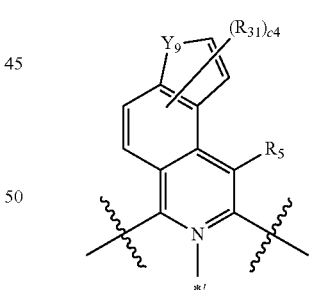
Formula 5-35
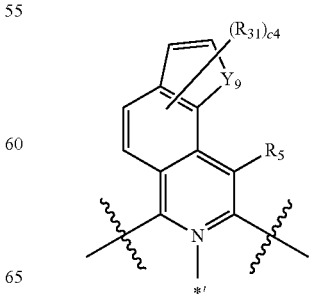

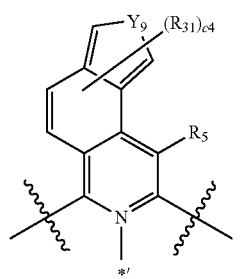 Formula 5-36
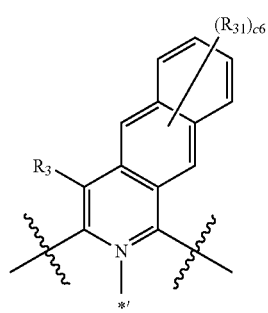 Formula 5-37
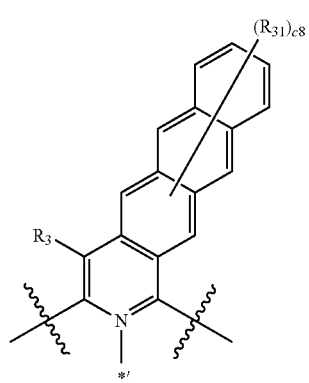 Formula 5-38
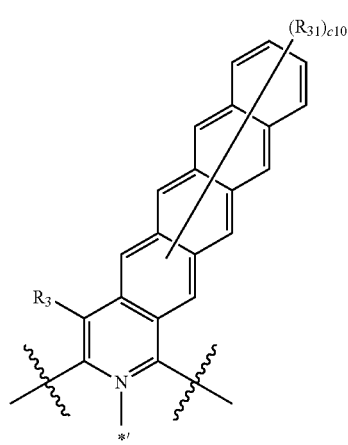 Formula 5-39
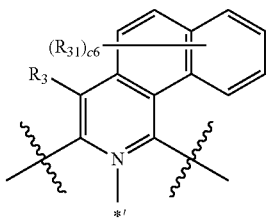 Formula 5-40
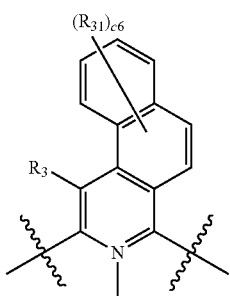 Formula 5-41
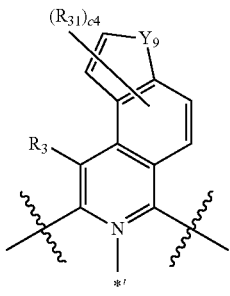 Formula 5-42
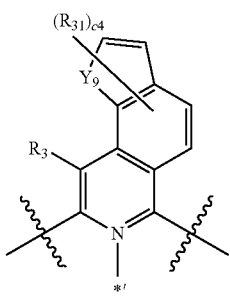 Formula 5-43
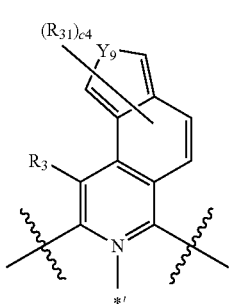 Formula 5-44

-continued

Formula 5-45
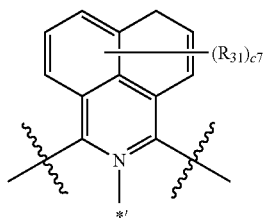

Formula 5-46
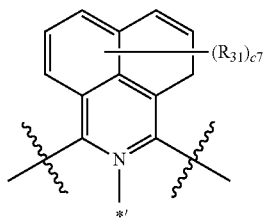

Formula 5-47
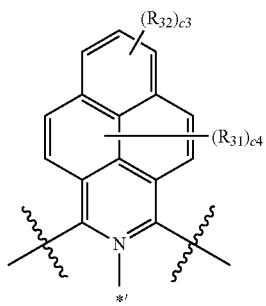

Formula 5-48
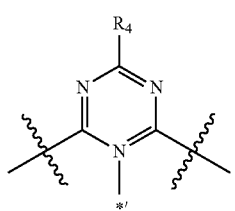

wherein, in Formulae 3-1 to 3-25, 3-31 to 3-74, 3-81 to 3-92, 4-1 to 4-53, and 5-1 to 5-48, $Y_7$ and $Y_8$ may be each independently O or S, $Y_9$ may be O, S, or $N(R_{39})$, $R_3$ to $R_5$ may be the same as those described herein, $R_{11}$ to $R_{20}$ may be each independently the same as $R_1$ described herein, $R_{21}$ to $R_{30}$ may be each independently the same as $R_2$ described herein, $R_{31}$ to $R_{39}$ may be each independently the same as $R_3$ described herein, c3 may be an integer selected from 0 to 3, c4 may be an integer selected from 0 to 4, c6 may be an integer selected from 0 to 6, c7 may be an integer selected from 0 to 7, c8 may be an integer selected from 0 to 8, c10 may be an integer selected from 0 to 10, and

*, *', and *'' may each indicate a binding site to M in Formula 1.

$R_3$ to $R_5$ and $R_{11}$ to $R_{39}$ in Formulae 3-1 to 3-25, 3-31 to 3-74, 3-81 to 3-92, 4-1 to 4-53, and 5-1 to 5-48 are as provided herein.

$R_1$ to $R_7$ and $R_{11}$ to $R_{39}$ may be each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$).

According to an embodiment, $R_1$ to $R_7$ and $R_{11}$ to $R_{39}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzothiazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and
—N(Q$_1$)(Q$_2$), —Si(Q$_3$)(Q$_4$)(Q$_5$), —B(Q$_6$)(Q$_7$), and —P(=O)(Q$_8$)(Q$_9$),
wherein Q$_1$ to Q$_9$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, R$_1$ to R$_7$ and R$_{11}$ to R$_{39}$ may be each independently selected from
hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;
a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and
—N(Q$_1$)(Q$_2$), —Si(Q$_3$)(Q$_4$)(Q$_5$), —B(Q$_6$)(Q$_7$), and —P(=O)(Q$_8$)(Q$_9$),
wherein Q$_1$ to Q$_9$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, $R_1$ to $R_7$ and $R_{11}$ to $R_{39}$ may be each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-38, and —Si(Q$_3$)(Q$_4$)(Q$_5$), but embodiments are not limited thereto:

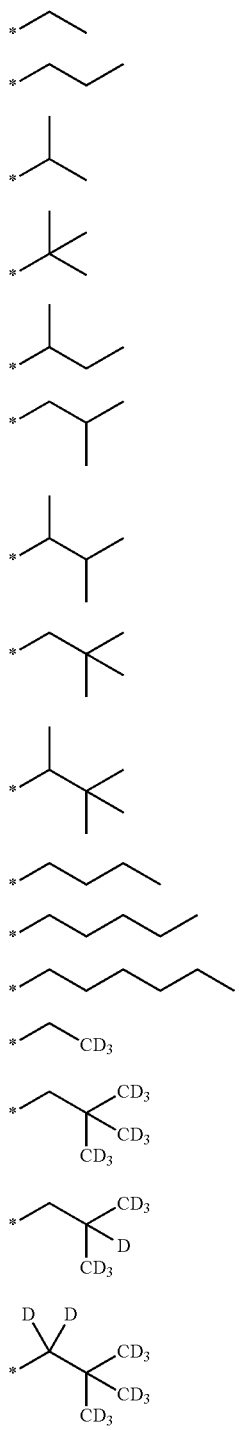

Formula 9-1
Formula 9-2
Formula 9-3
Formula 9-4
Formula 9-5
Formula 9-6
Formula 9-7
Formula 9-8
Formula 9-9
Formula 9-10
Formula 9-11
Formula 9-12
Formula 9-13
Formula 9-14
Formula 9-15
Formula 9-16

-continued

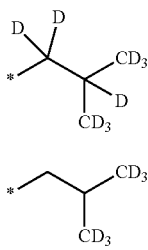

Formula 9-17

Formula 9-18

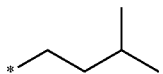

Formula 9-19

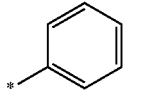

Formula 10-1

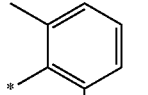

Formula 10-2

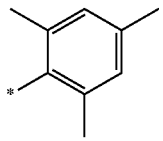

Formula 10-3

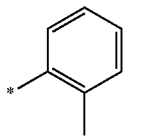

Formula 10-4

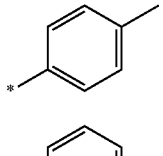

Formula 10-5

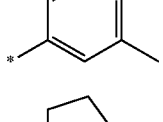

Formula 10-6

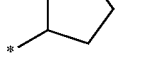

Formula 10-7

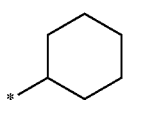

Formula 10-8

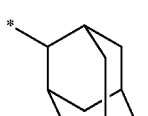

Formula 10-9

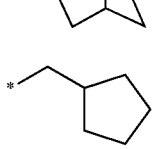

Formula 10-10

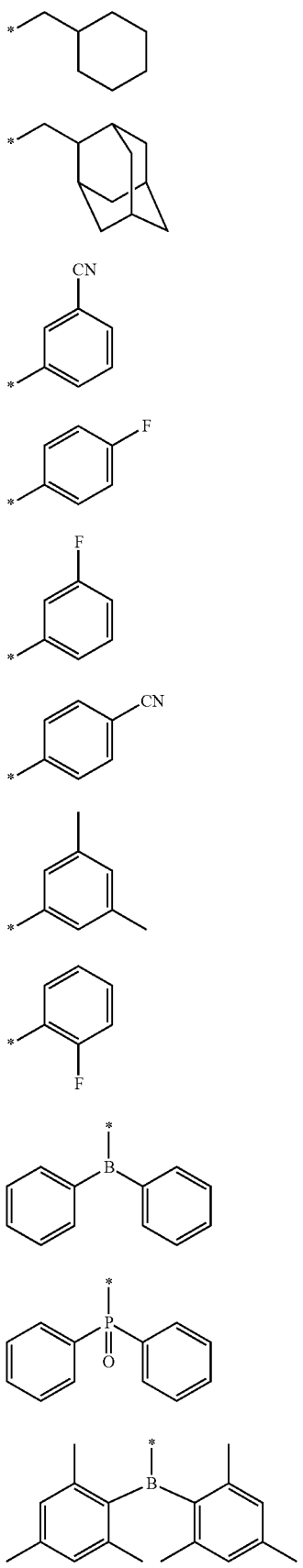
Formula 10-11
Formula 10-12
Formula 10-13
Formula 10-14
Formula 10-15
Formula 10-16
Formula 10-17
Formula 10-18
Formula 10-19
Formula 10-20
Formula 10-21
Formula 10-22
Formula 10-23
Formula 10-24
Formula 10-25
Formula 10-26
Formula 10-27
Formula 10-28
Formula 10-29
Formula 10-30
Formula 10-31

-continued

Formula 10-32
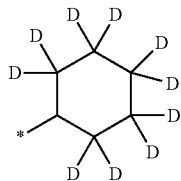

Formula 10-33
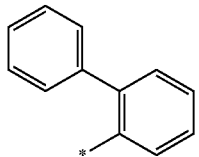

Formula 10-34
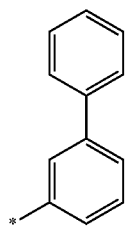

Formula 10-35
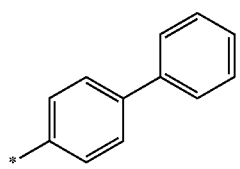

Formula 10-36
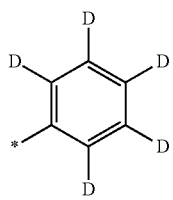

Formula 10-37
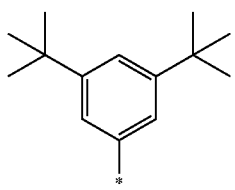

Formula 10-38
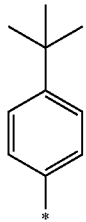

wherein, in Formulae 9-1 to 9-19 and 10-1 to 10-38, * indicates a binding site to an adjacent atom.

In Formula 2, b1 and b2 may be each independently an integer selected from 0 to 3, and when b1 is 2 or greater, groups $R_1$ may be identical to or different from each other, and when b2 is 2 or greater, groups $R_2$ may be identical to or different from each other.

In Formula 2, two of the b1 number of groups $R_1$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted cyclopentane group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, or a substituted or unsubstituted naphthalene group).

In Formula 2, two of the b2 number of groups $R_2$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted cyclopentane group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, or a substituted or unsubstituted naphthalene group).

According to an embodiment, a moiety represented by

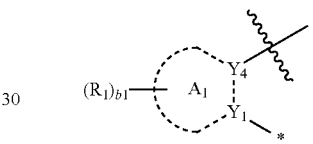

in Formula 2 may be represented by one of Formulae 3-1, 3-5, 3-9, 3-13, 3-31 to 3-34, 3-47 to 3-50, 3-81, 3-85, and 3-89, but embodiments are not limited thereto.

In various embodiments, a moiety represented by

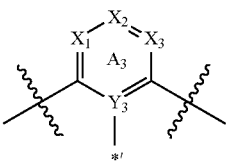

in Formula 2 may be represented by one of Formulae 5-1 to 5-28, 5-29, and 5-45, but embodiments are not limited thereto.

In some embodiments, in Formula 2, $T_2$ may be a group selected from *—O—*', *—S—*', *—C($R_6$)($R_7$)—*', *—N($R_6$)—*', and *—Si($R_6$)($R_7$)—*', wherein * and *' in each of the foregoing groups independently indicate a binding site to a neighboring atom, and $R_6$ and $R_7$ may optionally be bound to each other via a first linking group, wherein the first linking group may be selected from a single bond, a $C_1$-$C_3$ alkylene group, and a $C_2$-$C_3$ alkenylene group;

a $C_1$-$C_3$ alkylene group and a $C_2$-$C_3$ alkenylene group, each substituted with at least one selected from deuterium, a cyano group, $C_1$-$C_{10}$ alkyl group, $C_1$-$C_{10}$ alkoxy group, a phenyl group, and a biphenyl group, and a2 may be 1.

In some embodiments, in Formula 2, $T_1$ may be a single bond, $T_2$ may be a group selected from *—O—*', *—S—*', *—C($R_6$)($R_7$)—*', *—N($R_6$)—*', and *—Si($R_6$)($R_7$)—*', wherein * and *' in each of the foregoing groups independently indicate a binding site to a neighboring atom, $R_6$ to $R_7$ may be each independently selected from hydrogen, deuterium, a $C_1$-$C_{10}$ alkyl group, a $C_1$-$C_{10}$ alkoxy group, a phenyl group, and a biphenyl group; and a $C_1$-$C_{10}$ alkyl group, a $C_1$-$C_{10}$ alkoxy group, a phenyl group, and a biphenyl group, each substituted with at least one selected from deuterium, a cyano group, a $C_1$-$C_{10}$ alkyl group, a $C_1$-$C_{10}$ alkoxy group, and a phenyl group, wherein $R_6$ and $R_7$ may optionally be bound to each other via a single bond, and a1 may be 1.

According to some embodiments, $L_1$ in Formula 1 may be selected from ligands represented by Formula 2-1:

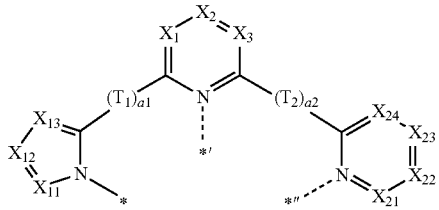

Formula 2-1 wherein, in Formula 2-1, $T_1$, $T_2$, a1, a2, $X_1$ to $X_3$, *, *', and *'' are the same as those described herein, $X_{11}$ may be C or N($R_{11a}$), $X_{12}$ may be C or N($R_{12a}$), $X_{13}$ may be C or N($R_{13a}$), $X_{21}$ may be C or N($R_{21a}$), $X_{22}$ may be C or N($R_{22a}$), $X_{23}$ may be C or N($R_{23a}$), $X_{24}$ may be C or N($R_{24a}$), $R_{11a}$ to $R_{13a}$ are each the same as described herein in connection with $R_1$, $R_{21a}$ to $R_{24a}$ are each the same as described herein in connection with $R_2$, at least two of $R_{11a}$ to $R_{13a}$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted cyclopentane group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, or a substituted or unsubstituted naphthalene group), and at least two of $R_{21a}$ to $R_{24a}$ may optionally be bound to each other to form a substituted or unsubstituted $C_5$-$C_{30}$ carbocyclic group or a substituted or unsubstituted $C_2$-$C_{30}$ heterocyclic group (e.g., a substituted or unsubstituted cyclopentane group, a substituted or unsubstituted cyclohexane group, a substituted or unsubstituted adamantane group, a substituted or unsubstituted benzene group, a substituted or unsubstituted pyridine group, a substituted or unsubstituted pyrimidine group, a substituted or unsubstituted pyrazine group, a substituted or unsubstituted pyridazine group, or a substituted or unsubstituted naphthalene group).

According to an embodiment, in Formula 2-1, a) two of $R_{11a}$ to $R_{13a}$ or b) two of $R_{21a}$ to $R_{24a}$ may optionally be bound to each other to form one selected from a cyclopentane group, a cyclohexane group, an adamantane group, a norbornane group, a benzene group, a pyridine group, a pyrimidine group, a naphthalene group, a pyrene group, and a chrysene group; and a cyclopentane group, a cyclohexane group, an adamantane group, a norbornane group, a benzene group, a pyridine group, a pyrimidine group, a naphthalene group, a pyrene group, and a chrysene group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, but embodiments are not limited thereto.

According to some embodiments, $L_1$ in Formula 1 may be selected from ligands represented by one of Formulae 2A to 2C:

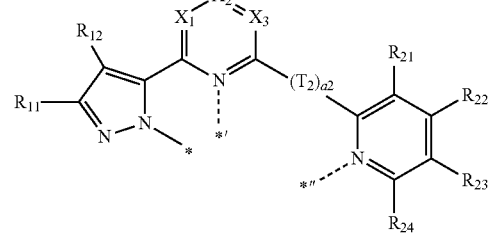

Formula 2A

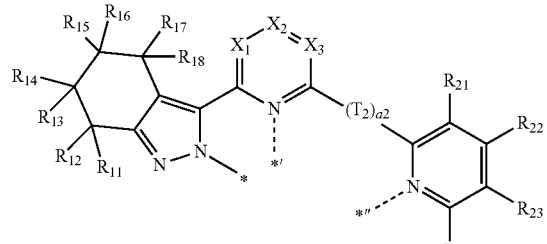

Formula 2B

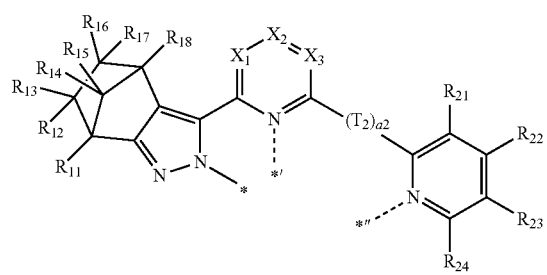

Formula 2C wherein, in Formulae 2A to 2C, $T_2$, a2, $X_1$ to $X_3$, *, *', and *'' are the same as those described herein, $R_{11}$ to $R_{18}$ are each the same as described herein in connection with $R_1$, $R_{21}$ to $R_{24}$ are each the same as described herein in connection with $R_2$, and at least two of $R_{21}$ to $R_{24}$ may optionally be bound to each other to form a substituted or unsubstituted $C_5$-$C_{30}$ carbocyclic group or a substituted or unsubstituted $C_2$-$C_{30}$ heterocyclic group.

$L_2$ in Formula 1 may be selected from ligands represented by Formula 6-1:

$$*\!\!-\!\!(T_3)_{a3}\!\!-\!\!R_{61} \qquad \text{Formula 6-1}$$

wherein, in Formula 6-1, $T_3$ may be a group selected from a single bond, *—O—*', *—S—*', *—C($R_{62}$)($R_{63}$)—*', *—C($R_{62}$)=*', *=C($R_{62}$)—*', *—C($R_{62}$)=C($R_{63}$)—*', *—C(=O)—*', *—C(=S)—*', *—C≡C—*', and *—N($R_{62}$)—*', wherein * and *' in each of the foregoing groups independently indicate a binding site to a neighboring atom, a3 may be an integer selected from 1 to 5, $R_{61}$ may be selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), —P(=O)($Q_8$)($Q_9$), and P($Q_{41}$)($Q_{42}$)($Q_{43}$), wherein $Q_1$ to $Q_9$ and $Q_{41}$ to $Q_{43}$ may be each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, $R_{62}$ to $R_{63}$ may be each independently selected from hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, $R_{62}$ and $R_{63}$ may optionally be bound to each other to form a substituted or unsubstituted $C_5$-$C_{30}$ carbocyclic group or a substituted or unsubstituted $C_2$-$C_{30}$ heterocyclic group, and

* in Formula 1 indicates a binding site to M.

In some embodiments, $R_{61}$ may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N(Q$_1$)(Q$_2$), —Si(Q$_3$)(Q$_4$)(Q$_5$), —B(Q$_6$)(Q$_7$), —P(=O)(Q$_8$)(Q$_9$), and P(Q$_{41}$)(Q$_{42}$)(Q$_{43}$), wherein Q$_1$ to Q$_9$ and Q$_{41}$ to Q$_{43}$ may be each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, but embodiments are not limited thereto.

According to an embodiment, L$_2$ in Formula 1 may be selected from ligands represented by one of Formulae 12-2 to 12-5, but embodiments are not limited thereto:

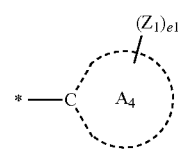

Formula 12-2

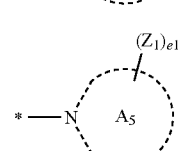

Formula 12-3

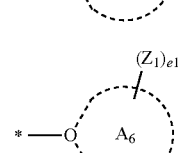

Formula 12-4

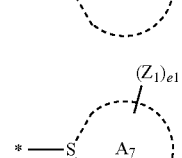

Formula 12-5 wherein, in Formulae 12-2 to 12-5, ring A$_4$ may be selected from a cyclopentene ring, a cyclohexene ring, a cycloheptene ring, a benzene ring, an indene ring, a naphthalene ring, an azulene ring, a heptalene ring, an indacene ring, acenaphthylene ring, a fluorene ring, a spiro-bifluorene ring, a benzofluorene ring, a dibenzofluorene ring, a phenalene ring, a phenanthrene ring, an anthracene ring, a fluoranthene ring, a triphenylene ring, a pyrene ring, a chrysene ring, a naphthacene ring, a picene ring, a perylene ring, a pentacene ring, a hexacene ring, a pentaphene ring, a rubicene ring, a coronene ring, an ovalene ring, a pyrrole ring, a thiophene ring, a furan ring, an imidazole ring, a pyrazole ring, a thiazole ring, an isothiazole ring, an oxazole ring, an isoxazole ring, a pyridine ring, a pyrazine ring, a pyrimidine ring, a pyridazine ring, an iso-indole ring, an indole ring, indazole ring, a purine ring, a quinoline ring, an isoquinoline ring, a benzoquinoline ring, a quinoxaline ring, a quinazoline ring, a cinnoline ring, a naphthyridine ring, a carbazole ring, a phenanthroline ring, a benzoimidazole ring, a benzofuran ring, a benzothiophene ring, a benzothiazole ring, an iso-benzothiazole ring, a benzoxazole ring, an isobenzoxazole ring, a triazole ring, a tetrazole ring, an oxadiazole ring, a thiadiazole ring, a triazine ring, a dibenzofuran ring, a dibenzothiophene ring, a benzocarbazole ring, a dibenzocarbazole ring, an imidazopyridine ring, and an imidazopyrimidine ring, ring $A_5$ may be selected from a pyrrole ring, an imidazole ring, a pyrazole ring, a thiazole ring, an isothiazole ring, an oxazole ring, an isoxazole ring, a pyridine ring, a pyrazine ring, a pyrimidine ring, a pyridazine ring, an iso-indole ring, an indole ring, an indazole ring, a purine ring, a quinoline ring, an isoquinoline ring, a benzoquinoline ring, a quinoxaline ring, a quinazoline ring, a cinnoline ring, a naphthyridine ring, a carbazole ring, a phenanthroline ring, a benzoimidazole ring, a benzofuran ring, a benzothiazole ring, an iso-benzothiazole ring, a benzoxazole ring, an isobenzoxazole ring, a triazole ring, a tetrazole ring, an oxadiazole ring, a thiadiazole ring, a triazine ring, a benzocarbazole ring, a dibenzocarbazole ring, an imidazopyridine ring, and an imidazopyrimidine ring, ring $A_6$ may be selected from a furan ring, an oxazole ring, an isoxazole ring, a benzofuran ring, a benzoxazole ring, an isobenzoxazole ring, an oxadiazole ring, and a dibenzofuran ring, ring $A_7$ may be selected from a thiophene ring, a thiazole ring, an isothiazole ring, a benzothiophene ring, a benzothiazole ring, an iso-benzothiazole ring, a thiadiazole ring, and a dibenzothiophene ring, $Z_1$ may be each independently selected from hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), wherein $Q_{31}$ to $Q_{39}$ may be each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, two of groups $Z_1$ may optionally be bound to each other to form a substituted or unsubstituted C$_5$-C$_{30}$ carbocyclic group or a substituted or unsubstituted C$_2$-C$_{30}$ heterocyclic group, e1 may be an integer selected from 0 to 8, and

* in Formula 1 indicates a binding site to M.

In some embodiments, $L_2$ in Formula 1 may be selected from ligands represented by one of Formulae 13-1 to 13-49 and 14-1 to 14-28, but embodiments are not limited thereto:

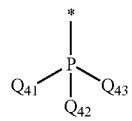

Formula 13-1

Formula 13-2

Formula 13-3

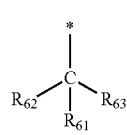

Formula 13-4

-continued
Formula 13-5
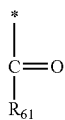
Formula 13-6
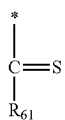
Formula 13-7
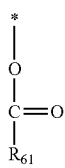
Formula 13-8
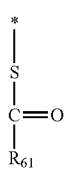
Formula 13-9
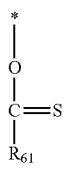
Formula 13-10
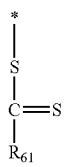
Formula 13-11
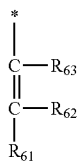
Formula 13-12
Formula 13-13
Formula 13-14
Formula 13-15
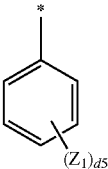
Formula 13-16
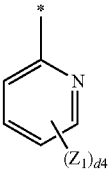
Formula 13-17
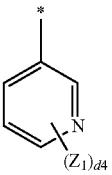
Formula 13-18
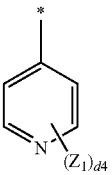
Formula 13-19
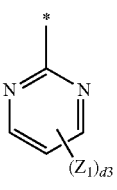
Formula 13-20
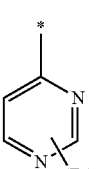
Formula 13-21
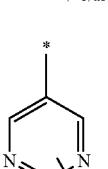

Formula 13-22
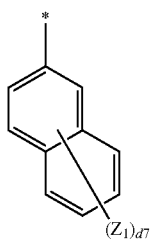
Formula 13-23
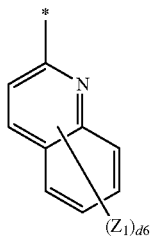
Formula 13-24
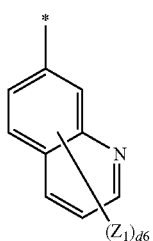
Formula 13-25
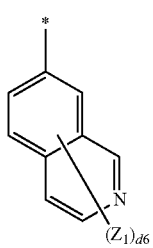
Formula 13-26
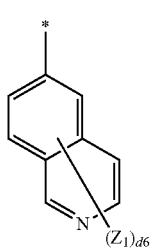
Formula 13-27
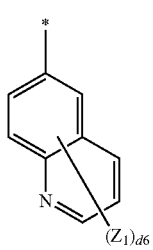
Formula 13-28
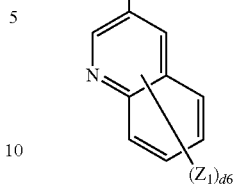
Formula 13-29
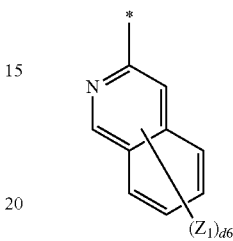
Formula 13-30
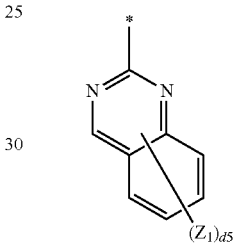
Formula 13-31
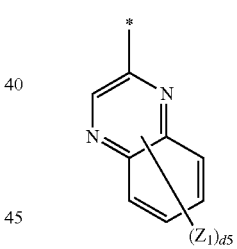
Formula 13-32
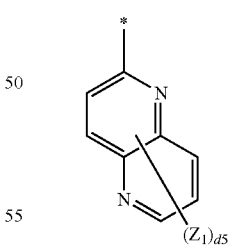
Formula 13-33
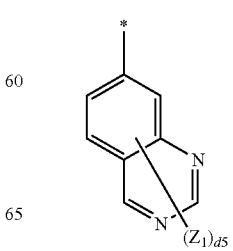

-continued
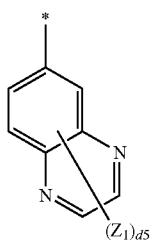
Formula 13-34
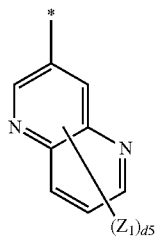
Formula 13-35
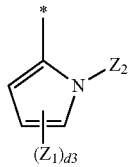
Formula 13-36
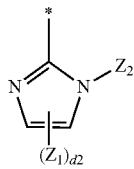
Formula 13-37
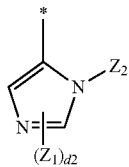
Formula 13-38
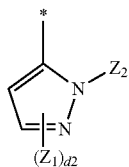
Formula 13-39
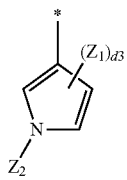
Formula 13-40
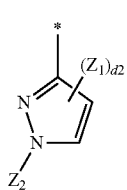
Formula 13-41
-continued
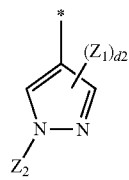
Formula 13-42
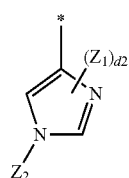
Formula 13-43
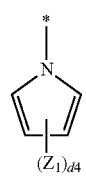
Formula 13-44
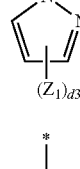
Formula 13-45
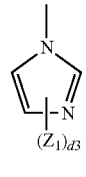
Formula 13-46
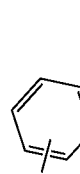
Formula 13-47
Formula 13-48
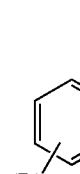
Formula 13-49
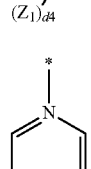
Formula 14-1

Formula 14-2
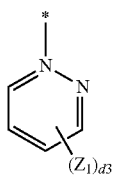
Formula 14-3
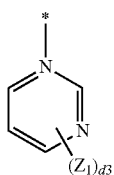
Formula 14-4
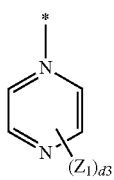
Formula 14-5
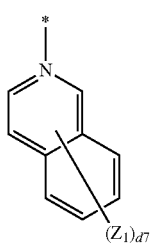
Formula 14-6
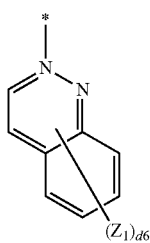
Formula 14-7
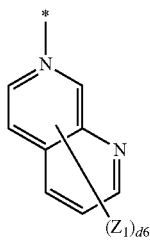
Formula 14-8
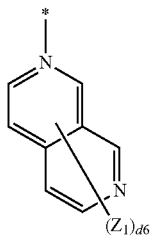
Formula 14-9
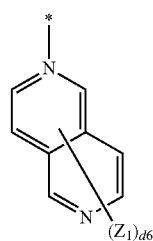
Formula 14-10
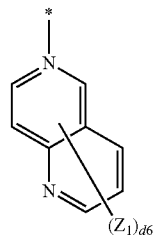
Formula 14-11
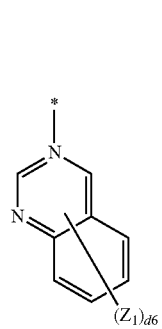
Formula 14-12
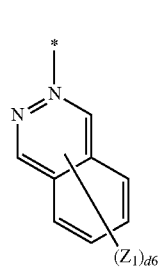
Formula 14-13
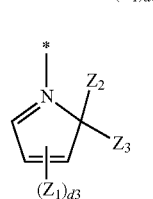
Formula 14-14
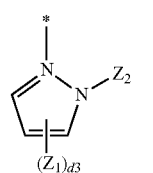
Formula 14-15
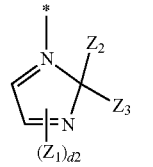

Formula 14-16
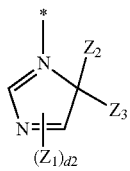

Formula 14-17
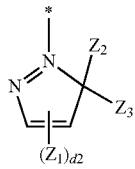

Formula 14-18
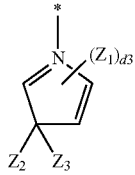

Formula 14-19
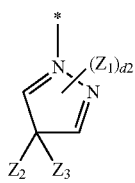

Formula 14-20
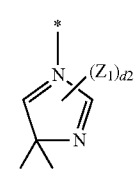

Formula 14-21
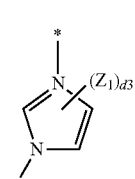

Formula 14-22
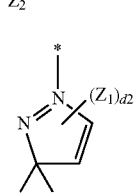

Formula 14-23
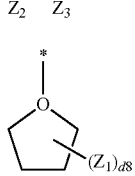

Formula 14-24
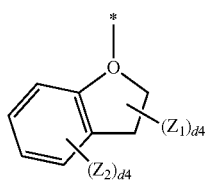

Formula 14-25
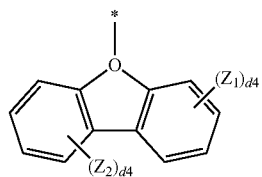

Formula 14-26
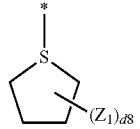

Formula 14-27
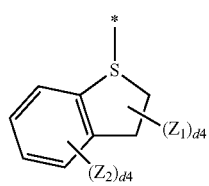

Formula 14-28
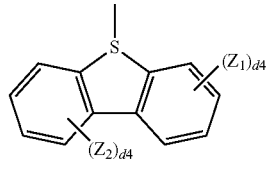

wherein, in Formulae 13-1 to 13-49 and 14-1 to 14-28, $R_{61}$ may be the same as described herein, $Z_1$ may be the same as described herein, $Z_2$ and $Z_3$ may be each independently the same as described herein in connection with $Z_1$, d2 may be an integer selected from 1 and 2, d3 may be an integer selected from 1 to 3, d4 may be an integer selected from 1 to 4, d5 may be an integer selected from 1 to 5, d6 may be an integer selected from 1 to 6, d7 may be an integer selected from 1 to 7, d8 may be an integer selected from 1 to 8, and

* in Formula 1 indicates a binding site to M.

The organometallic compound represented by Formula 1 may be one of Compounds 1 to 180, but embodiments are not limited thereto:

1

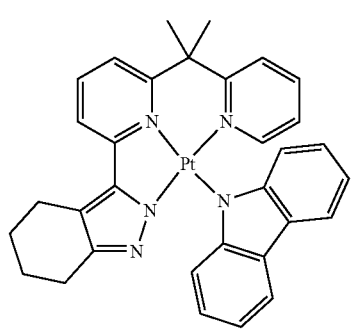

2
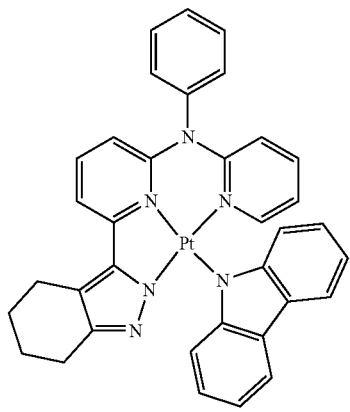
3
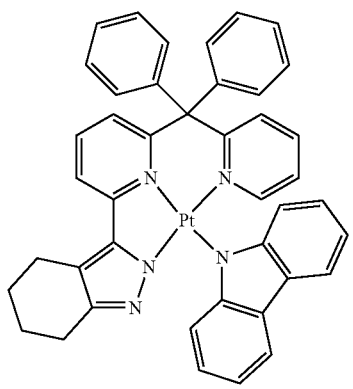
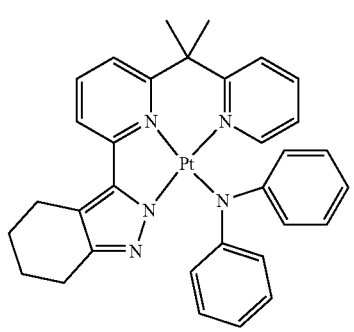
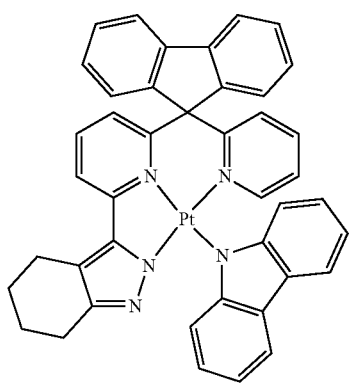
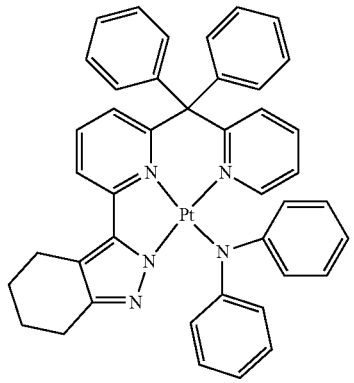
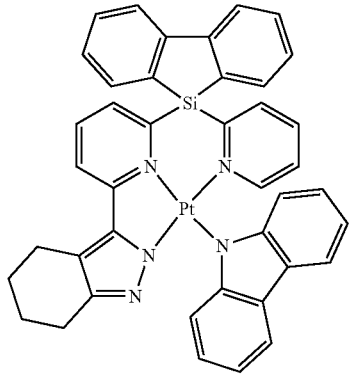
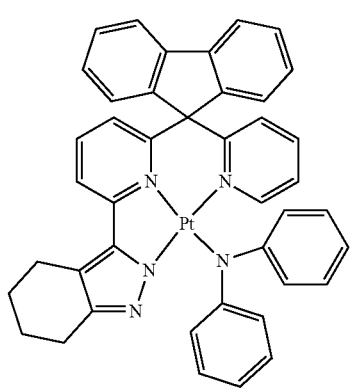
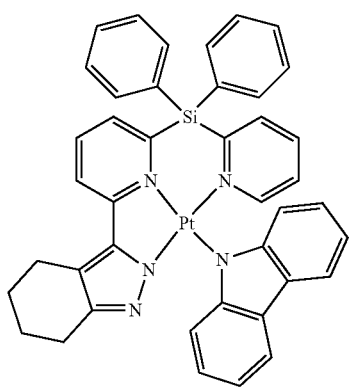

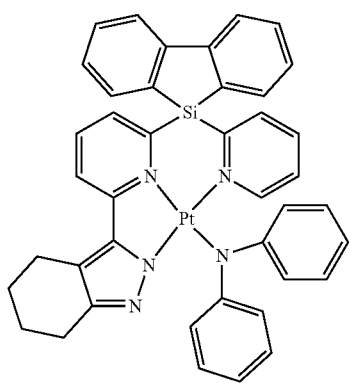
10
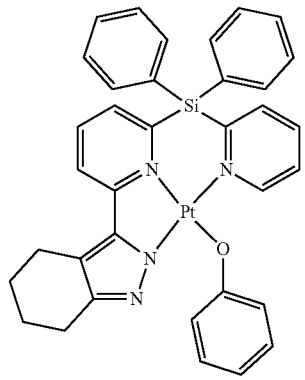
14
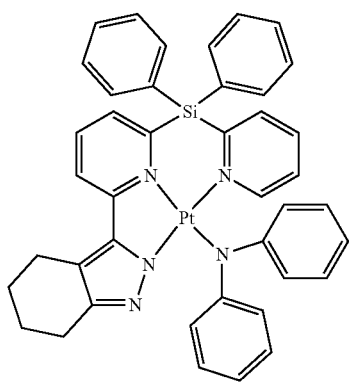
11
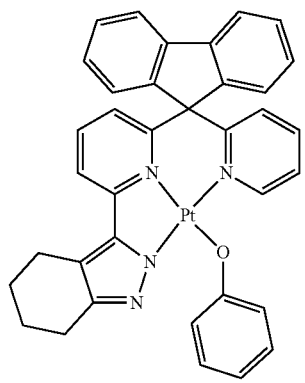
15
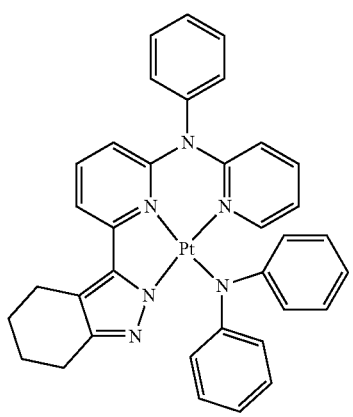
12
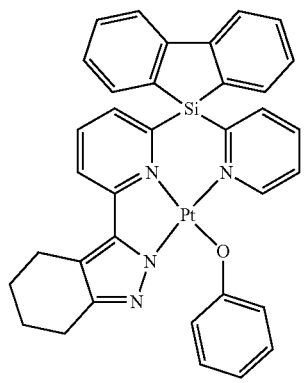
16
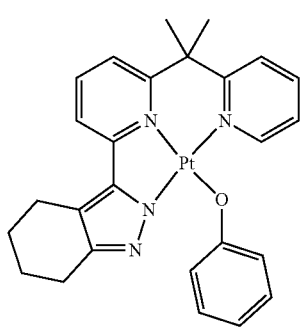
13
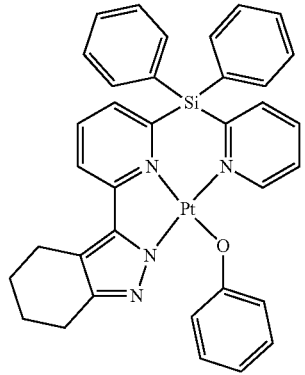
17

18
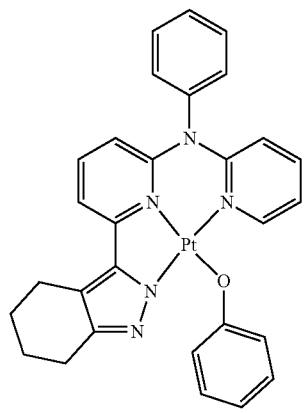
19
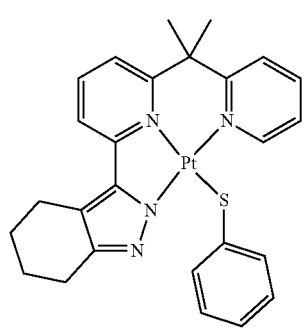
20
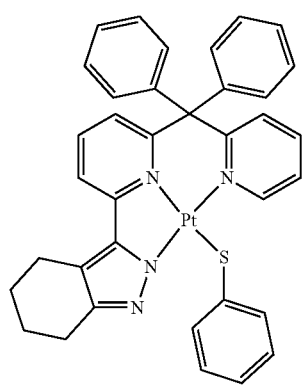
21
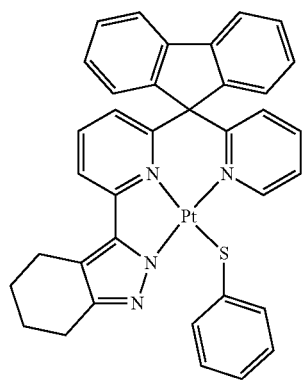
22
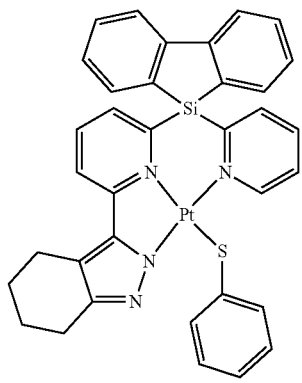
23
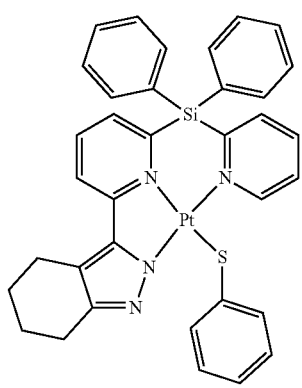
24
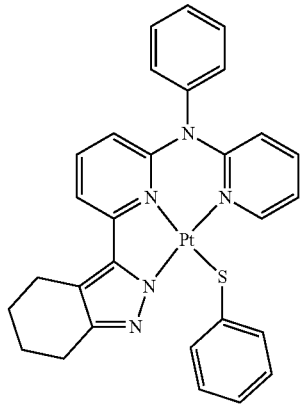
25
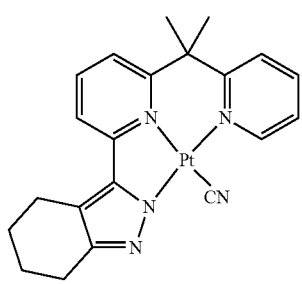

26
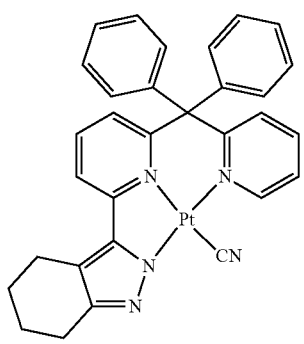
27
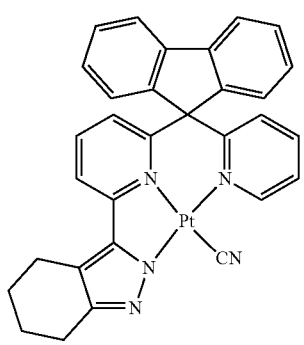
28
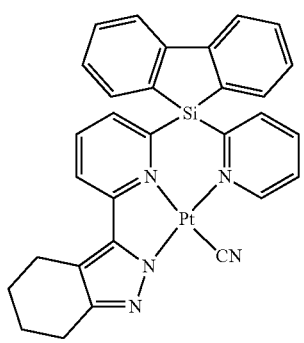
29
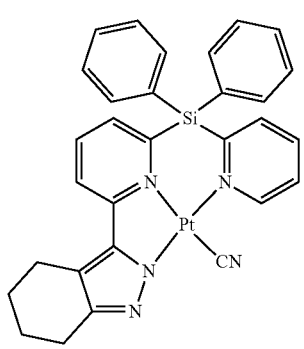
30
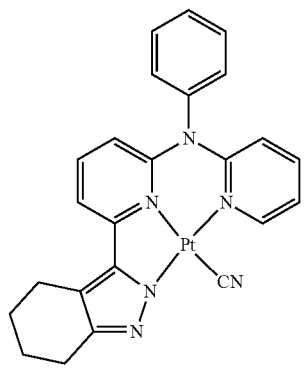
31
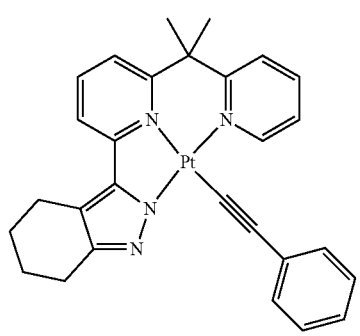
32
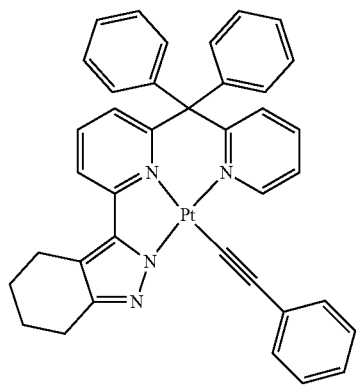
33
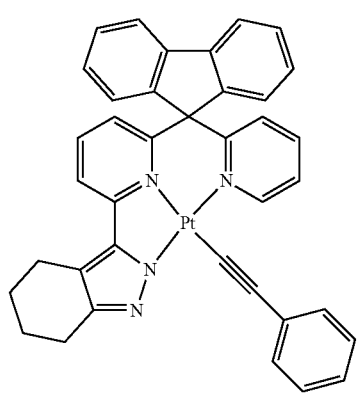

-continued
34
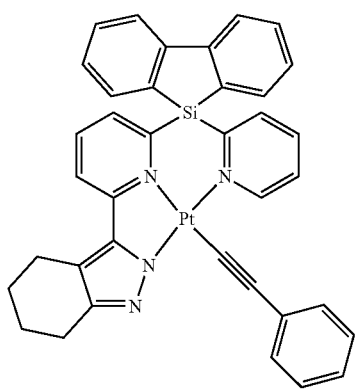
35
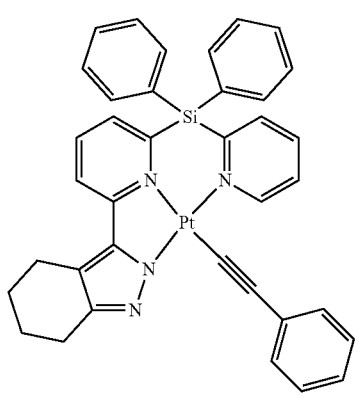
36
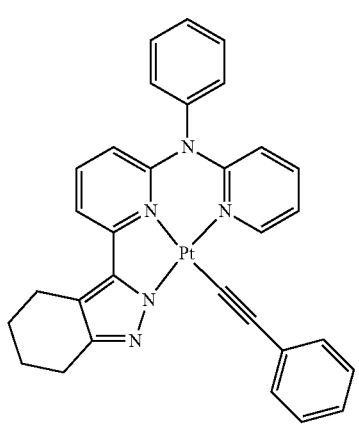
37
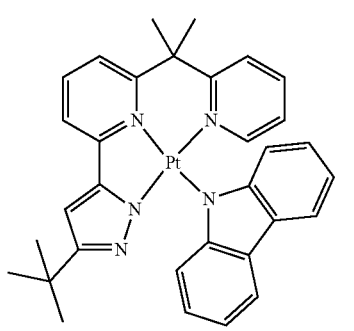
-continued
38
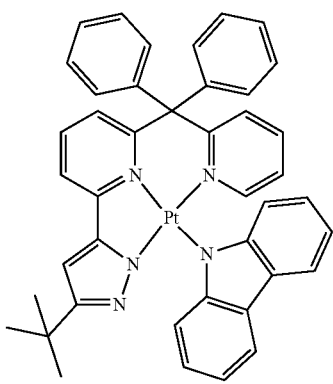
39
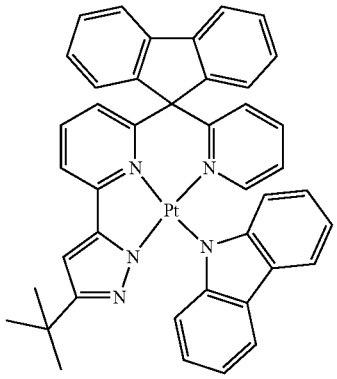
40
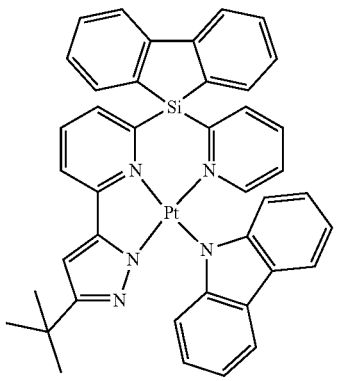
41
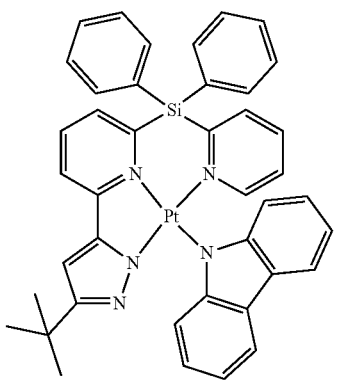

75
-continued
42
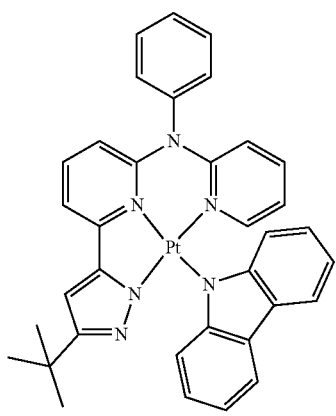
43
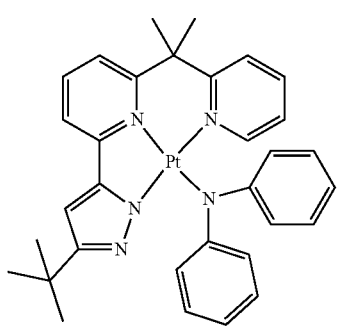
44
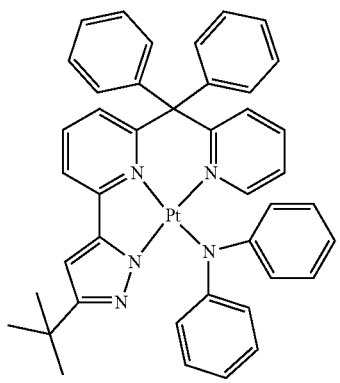
45
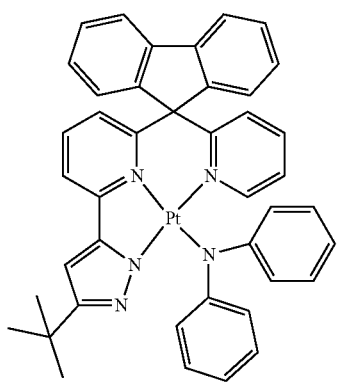
76
-continued
46
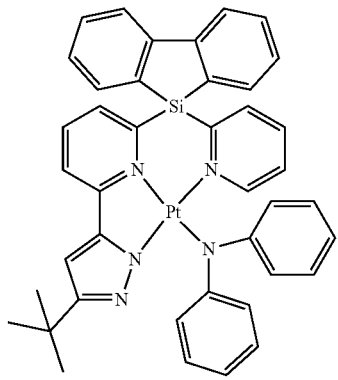
47
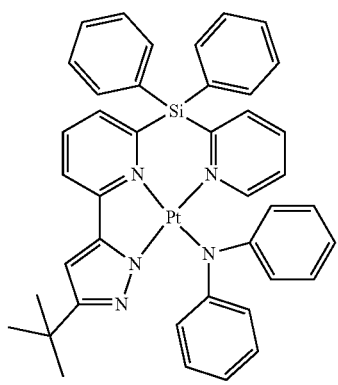
48
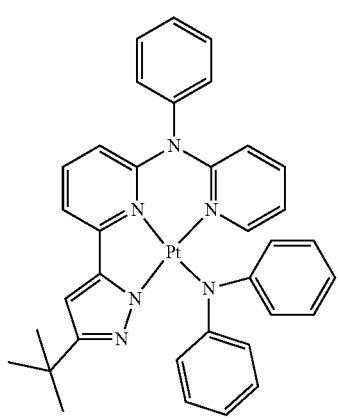
49
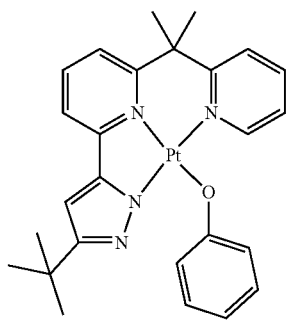

-continued
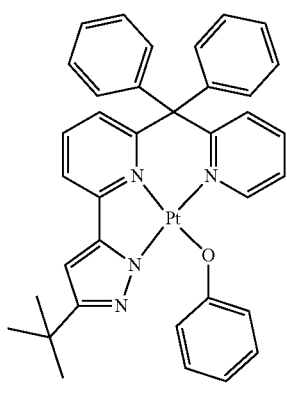
50
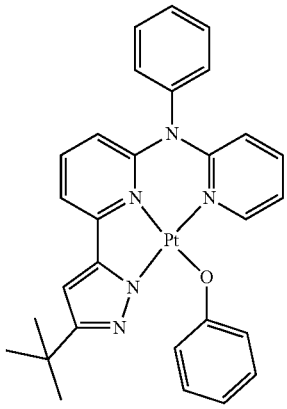
51
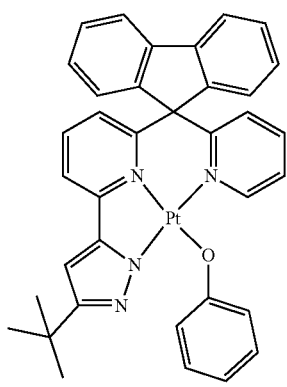
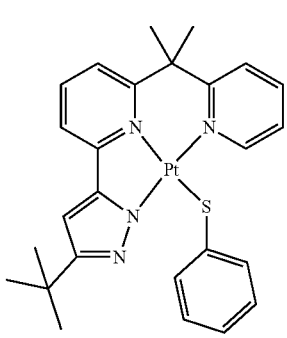
52
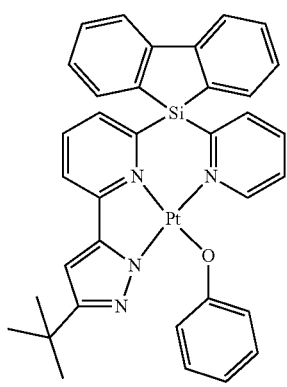
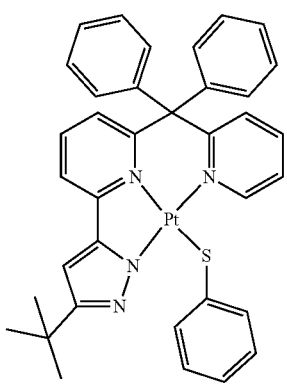
53
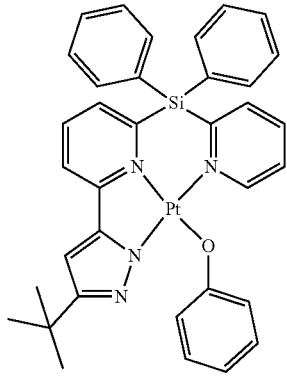
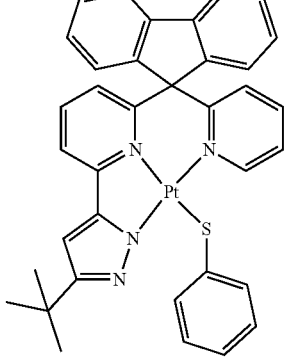

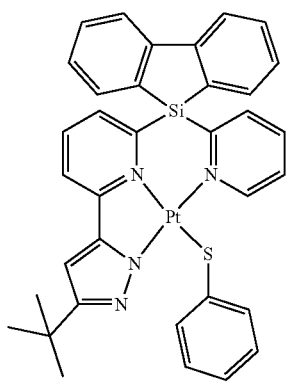
58
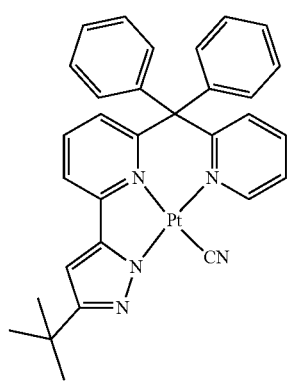
62
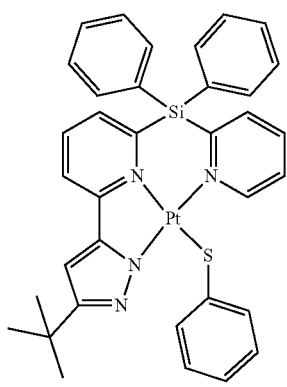
59
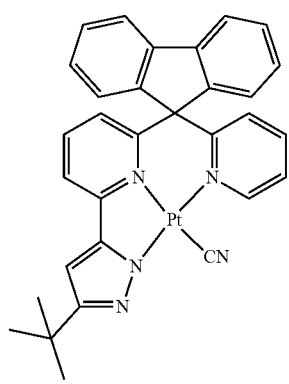
63
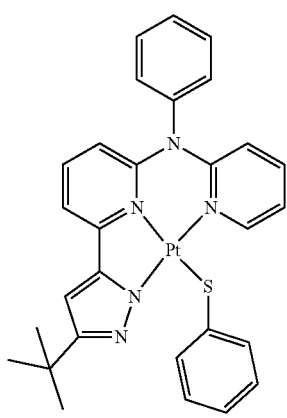
60
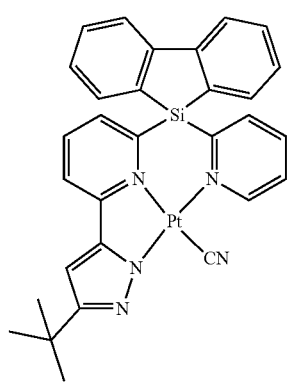
64
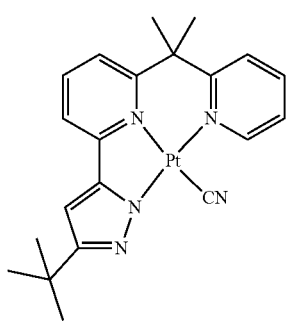
61
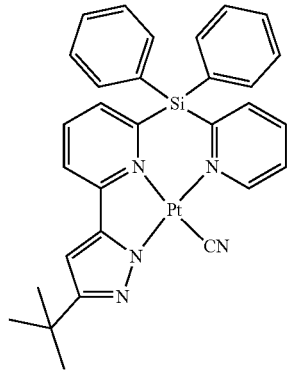
65

81
-continued
66
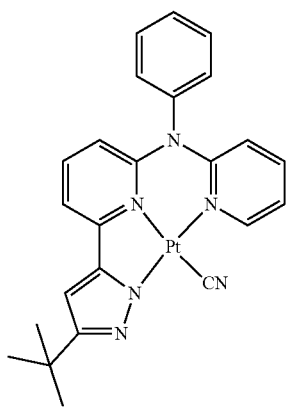
67
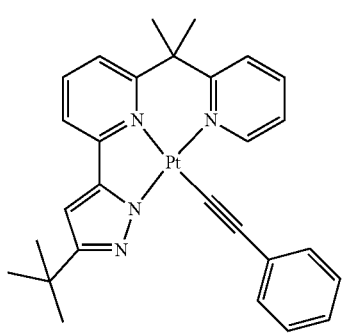
68
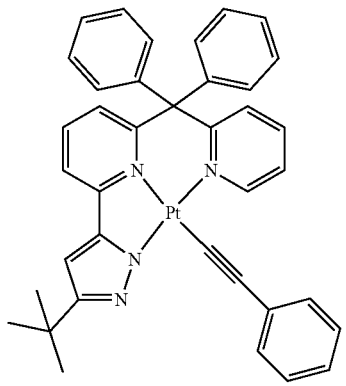
69
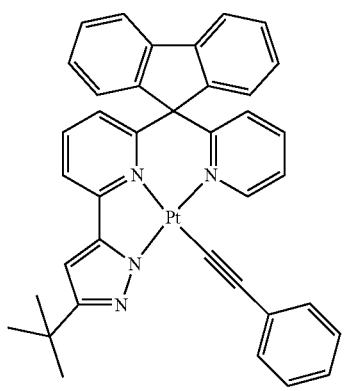
82
-continued
70
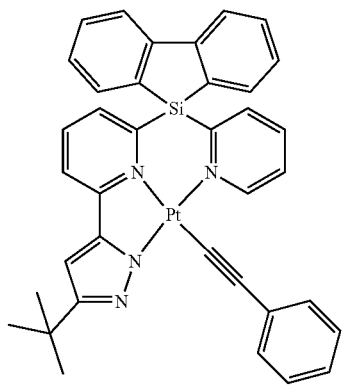
71
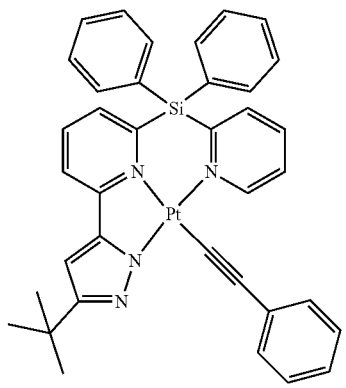
72
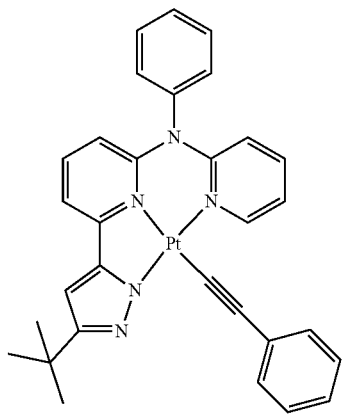
73
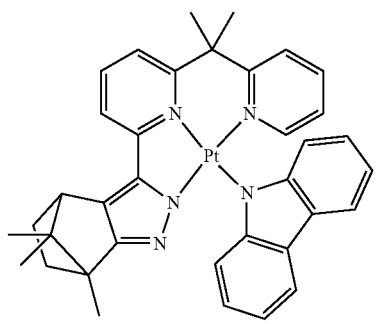

74
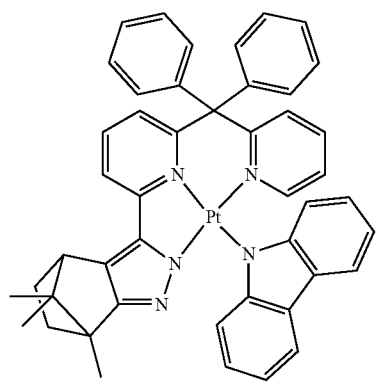
75
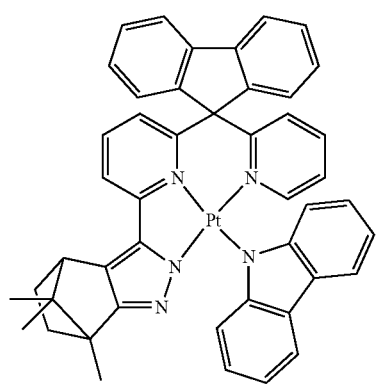
76
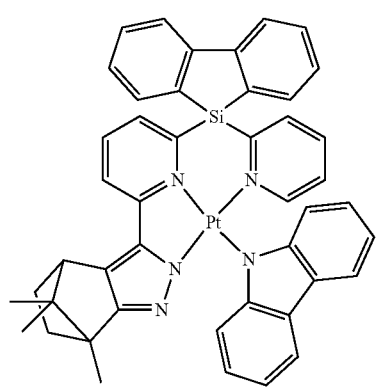
77
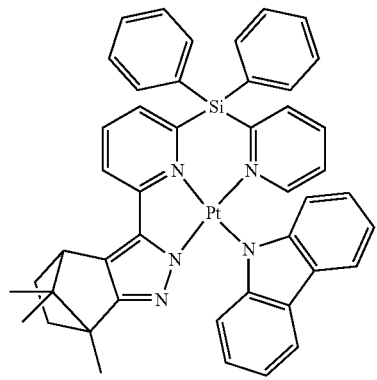
78
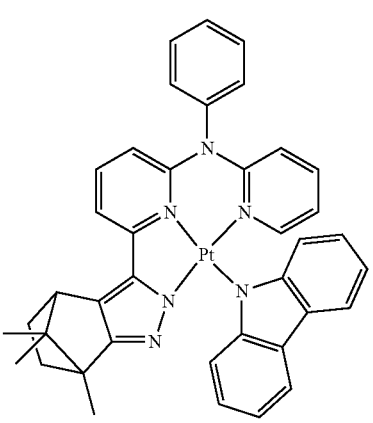
79
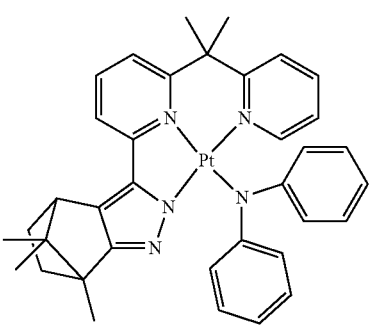
80
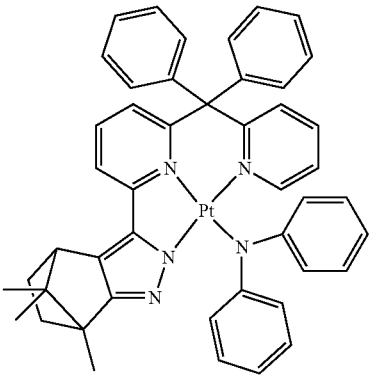
81
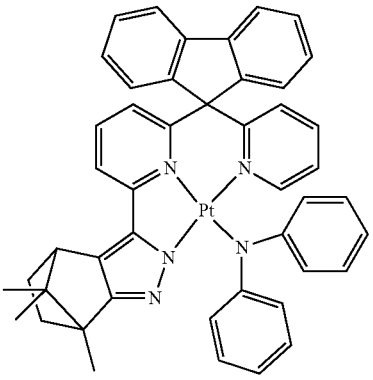

82
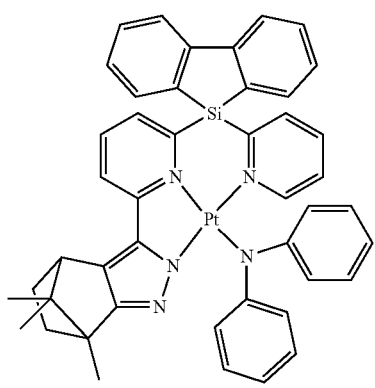
83
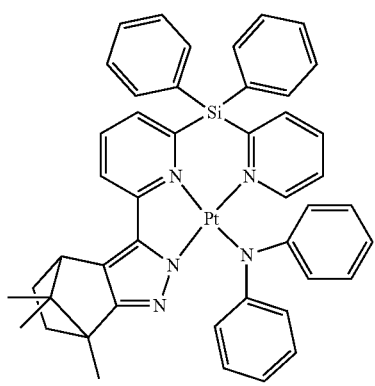
84
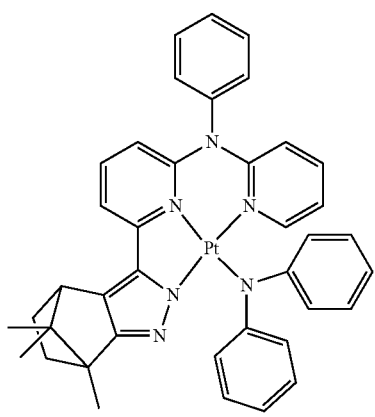
85
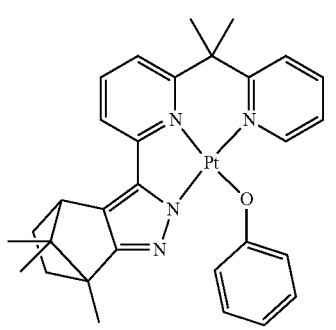
86
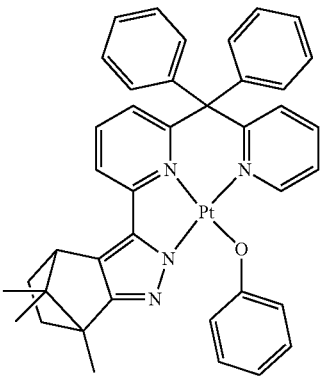
87
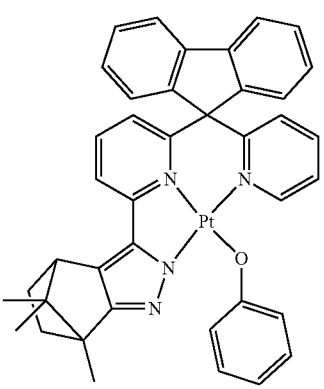
88
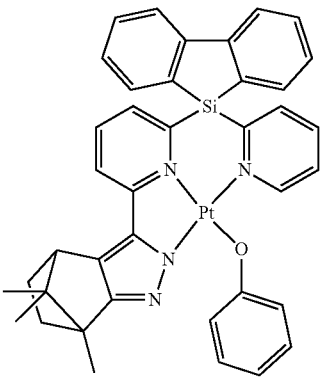
89
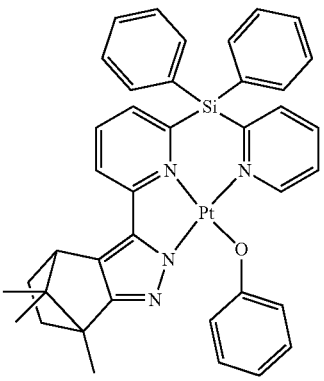

87
88
90
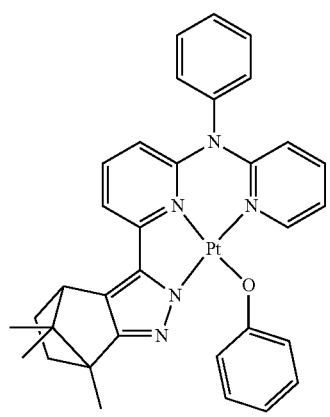
91
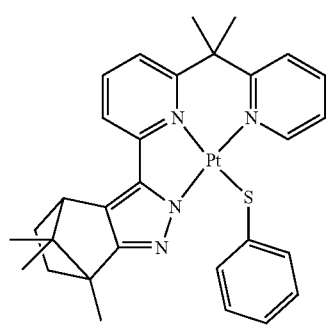
92
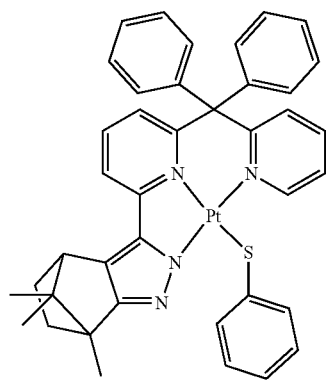
93
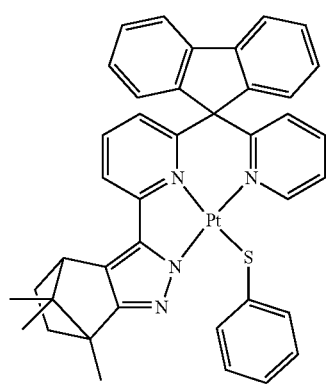
94
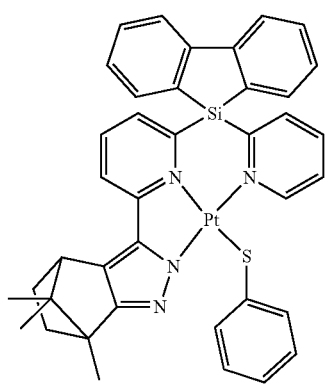
95
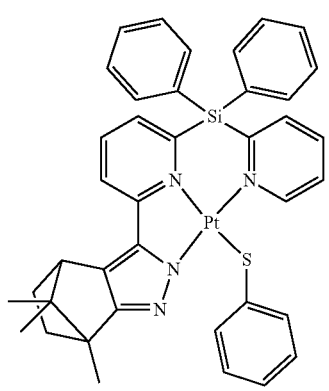
96
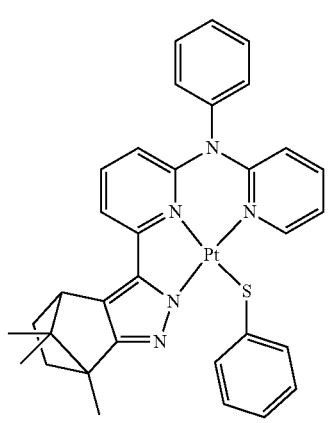
97
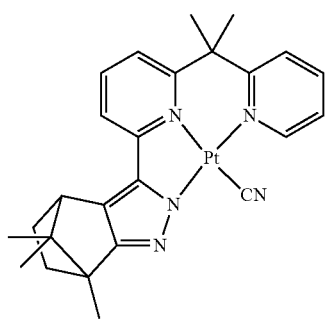

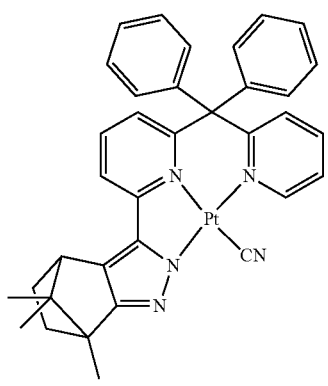
98
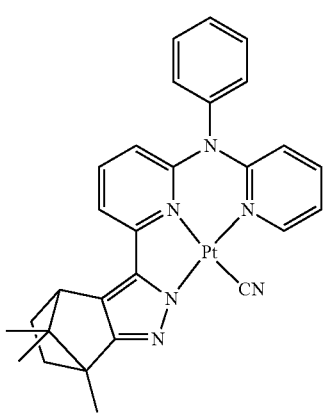
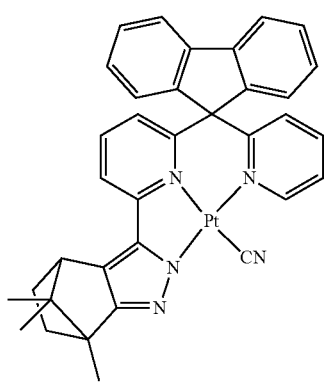
99
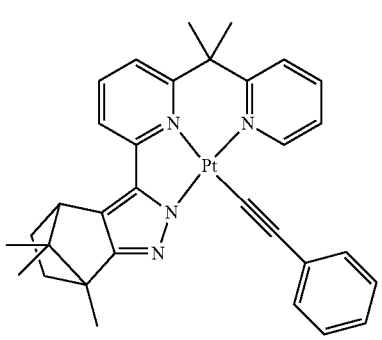
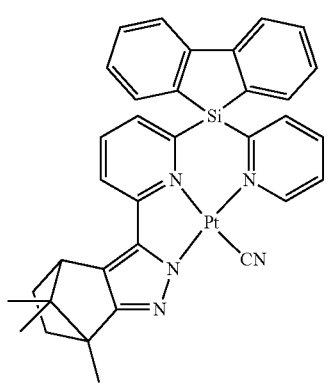
100
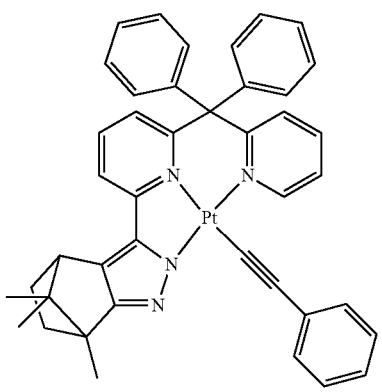
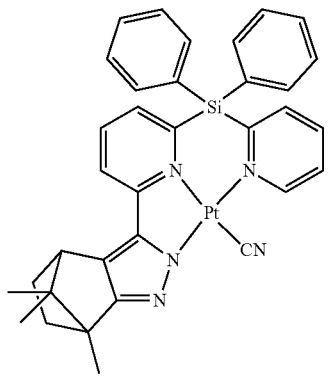
101
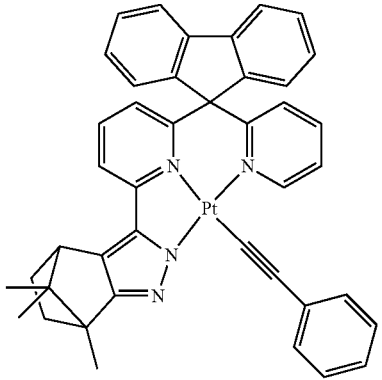

106 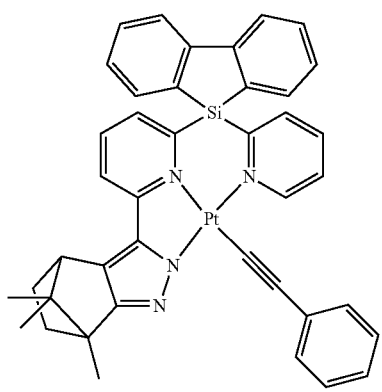
107 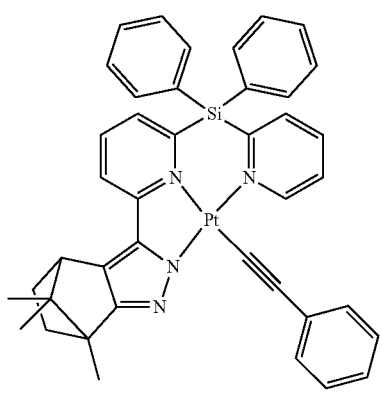
108 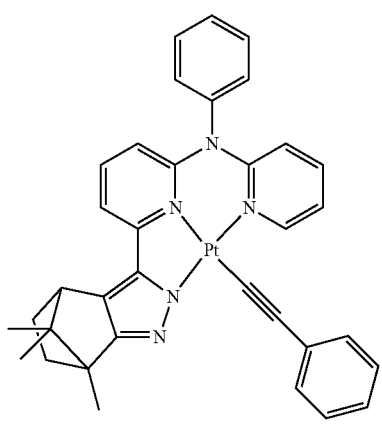
109 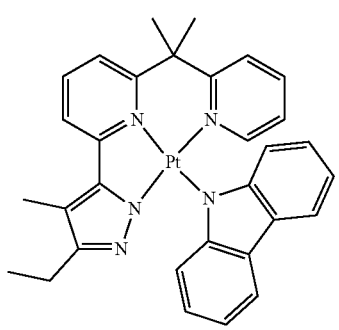
110 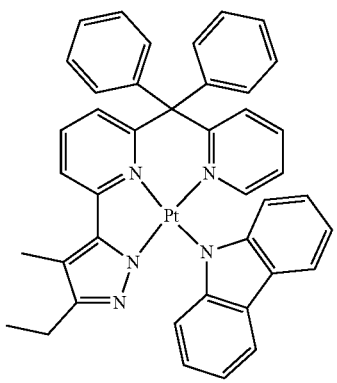
111 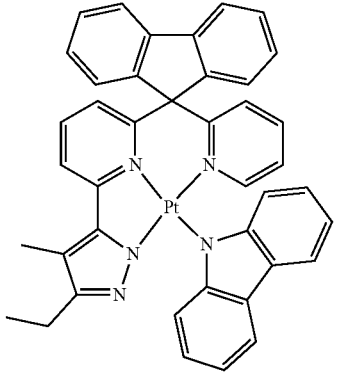
112 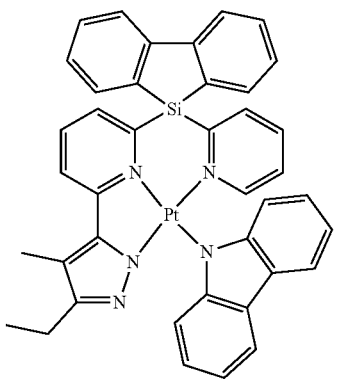
113 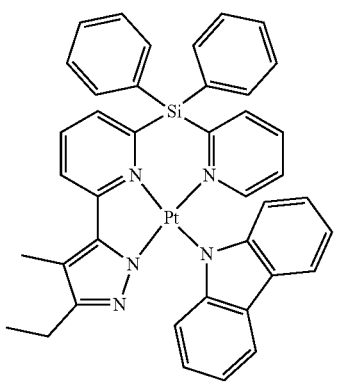

114
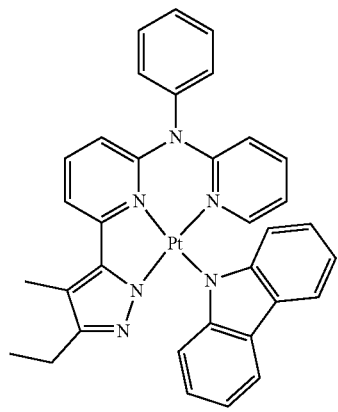
115
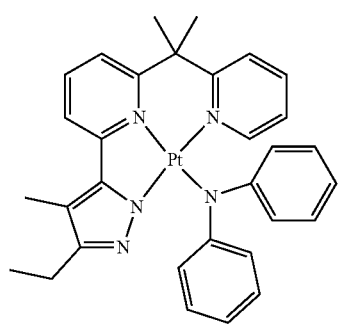
116
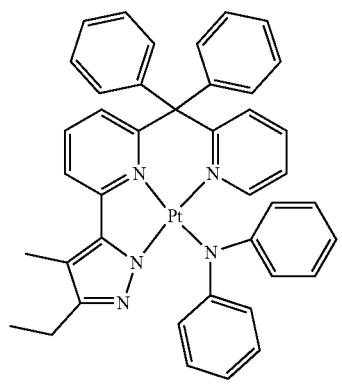
117
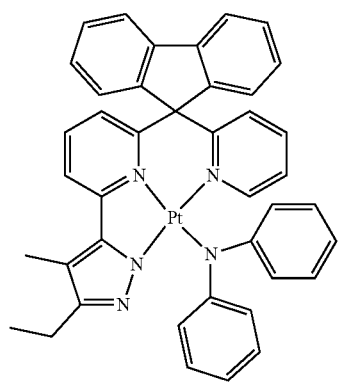
118
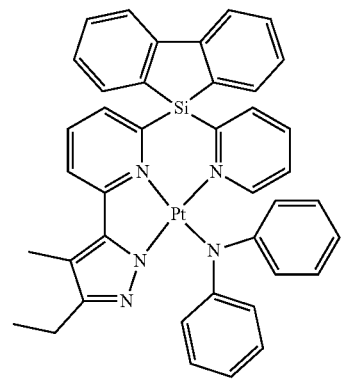
119
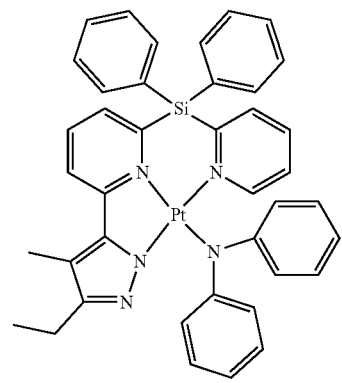
120
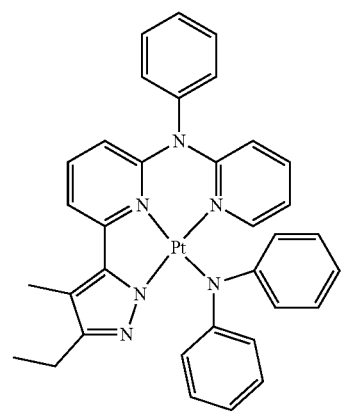
121
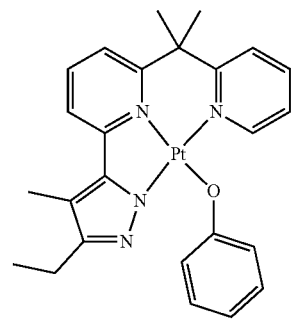

-continued
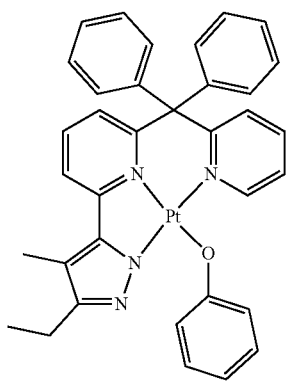
122
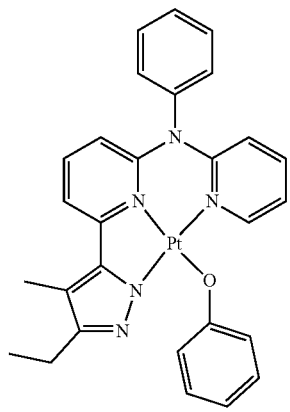
126
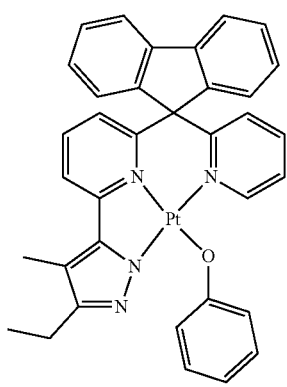
123
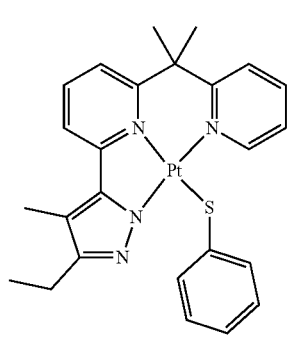
127
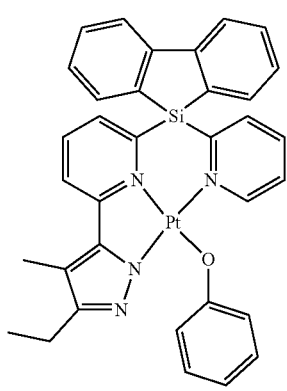
124
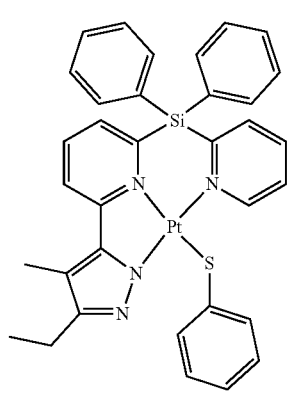
128
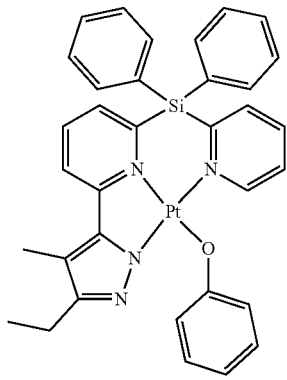
125
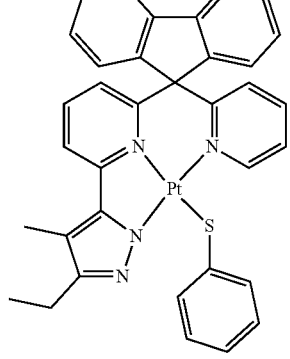
129

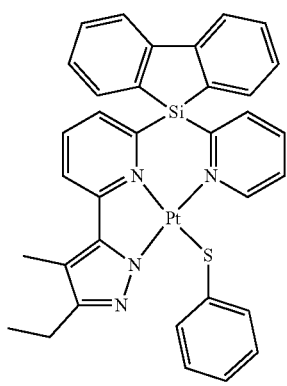
130
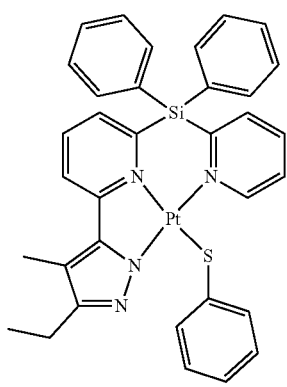
131
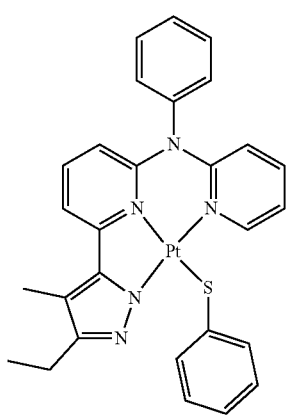
132
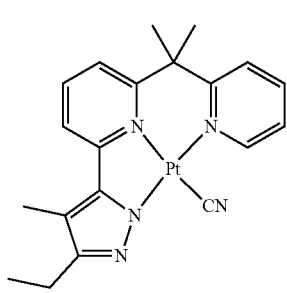
133
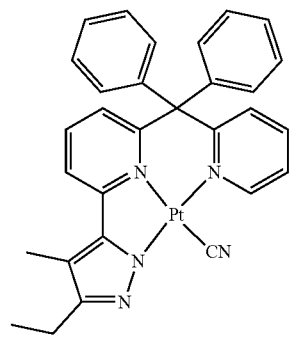
134
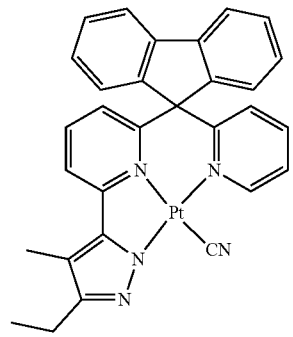
135
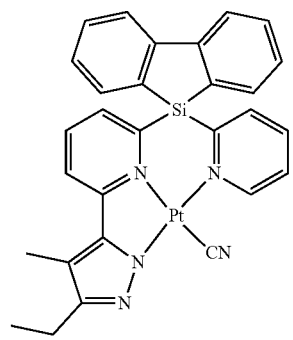
136
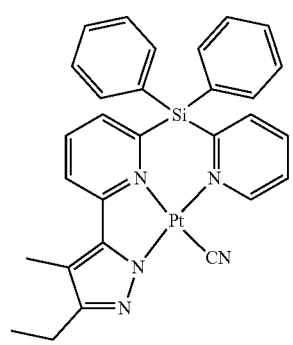
137

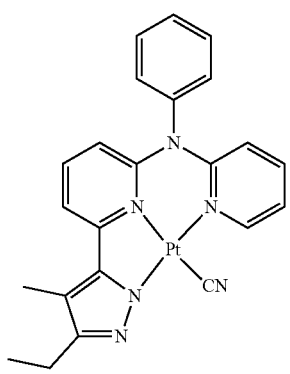
138
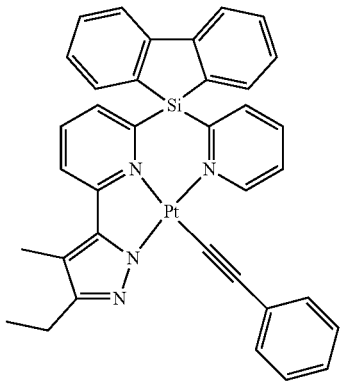
142
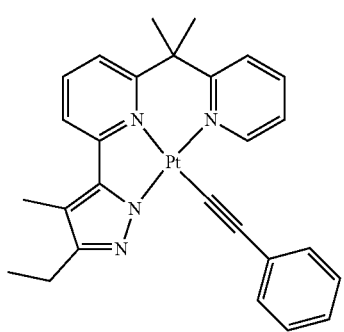
139
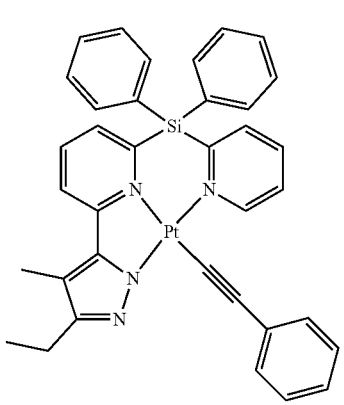
143
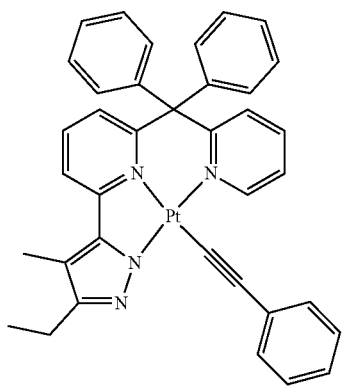
140
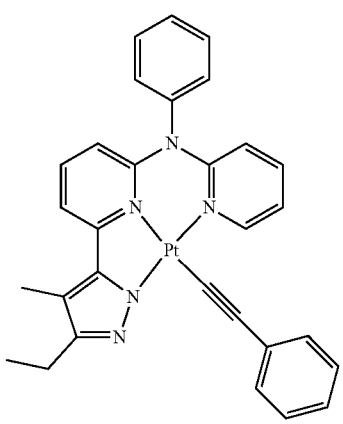
144
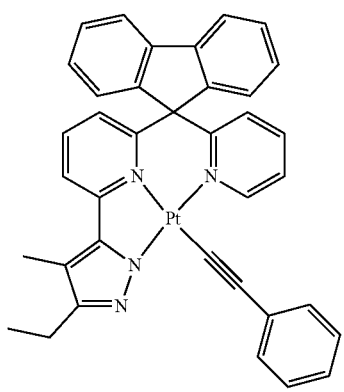
141
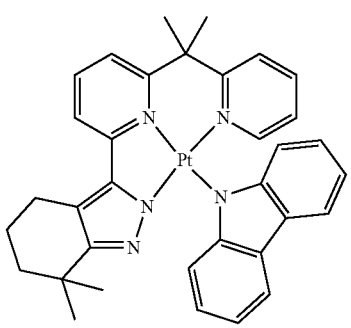
145

146
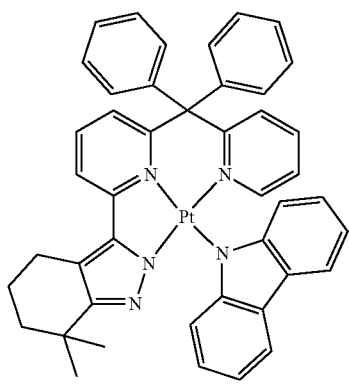
150
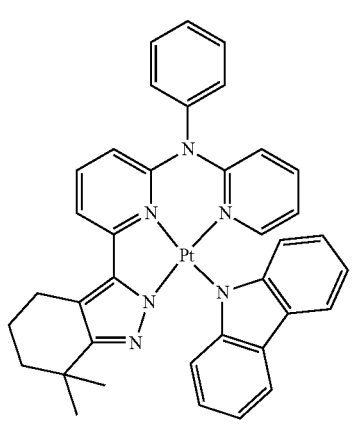
147
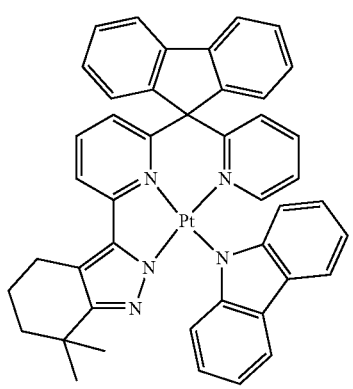
151
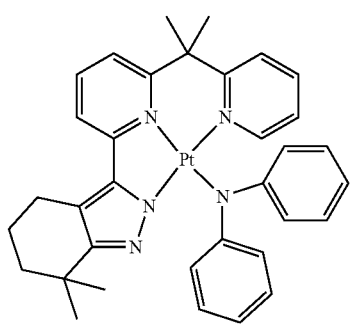
148
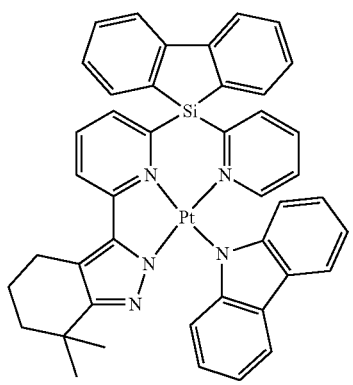
152
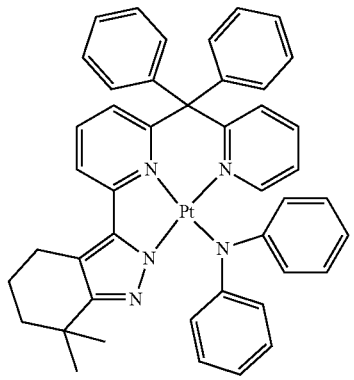
149
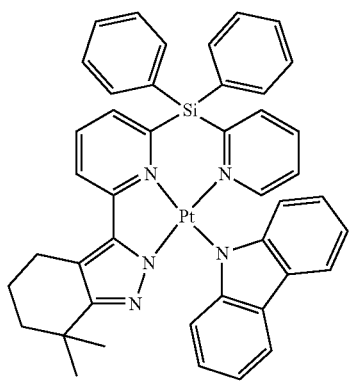
153
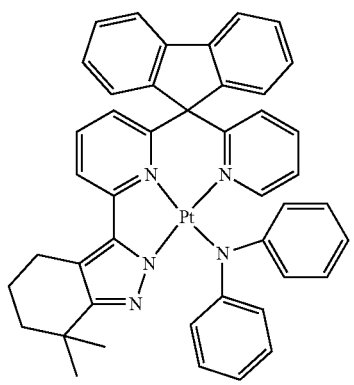

103
-continued
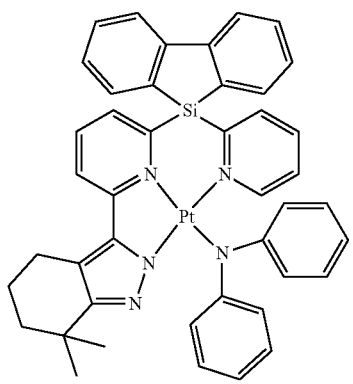
154
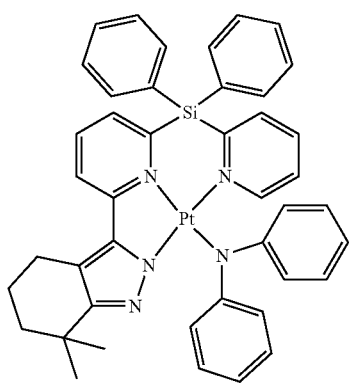
155
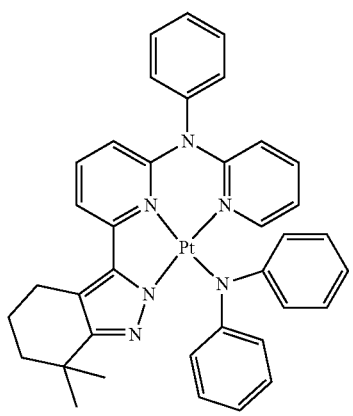
156
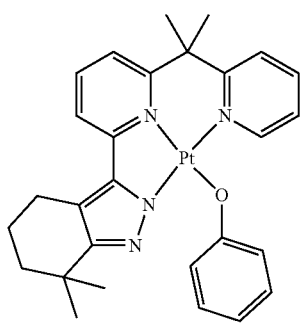
157
104
-continued
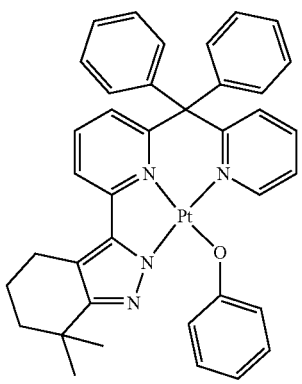
158
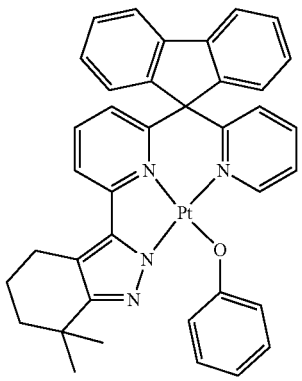
159
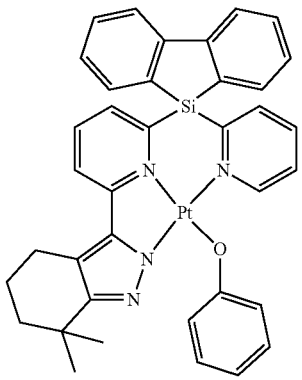
160
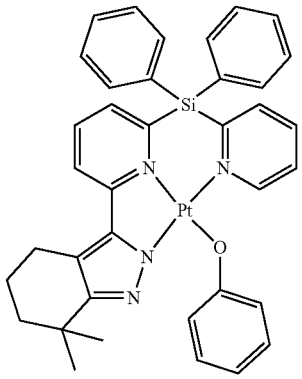
161

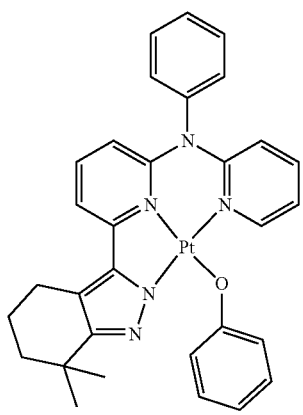
162
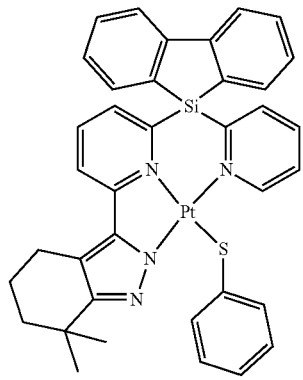
166
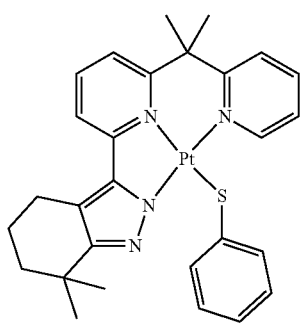
163
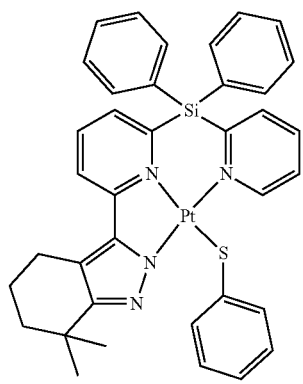
167
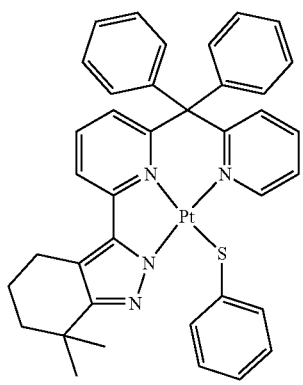
164
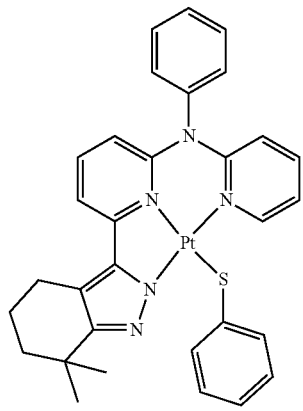
168
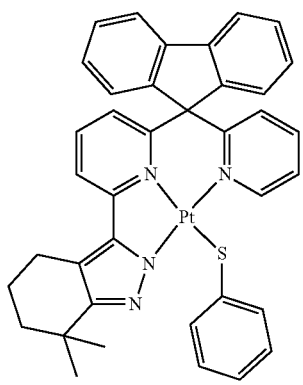
165
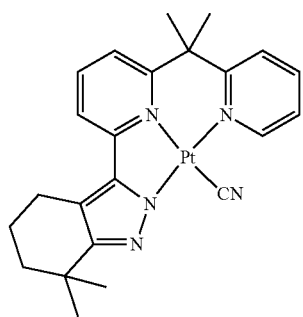
169

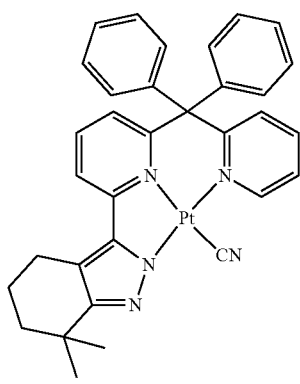
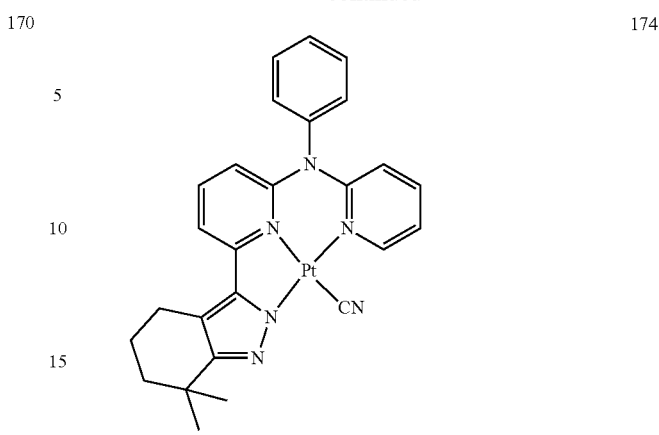
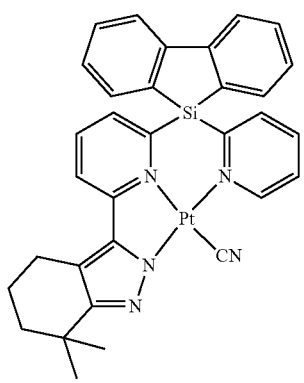
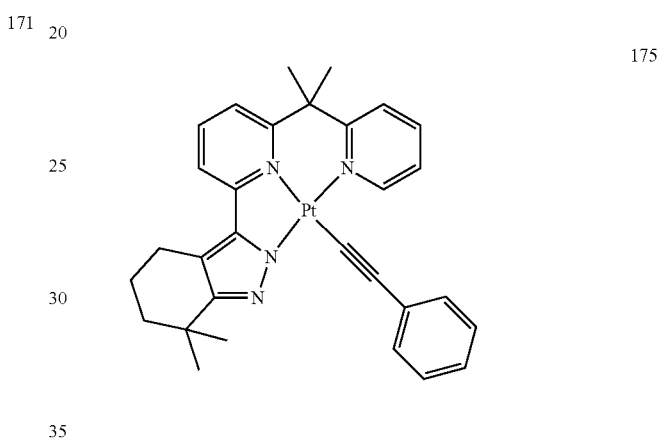
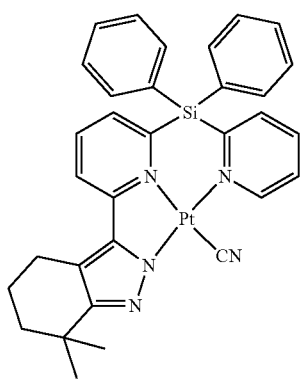
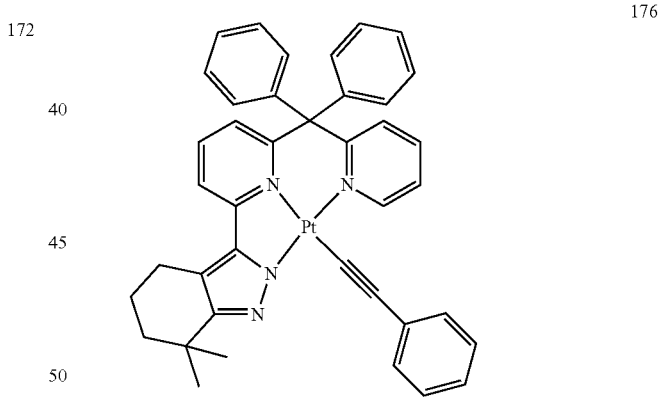
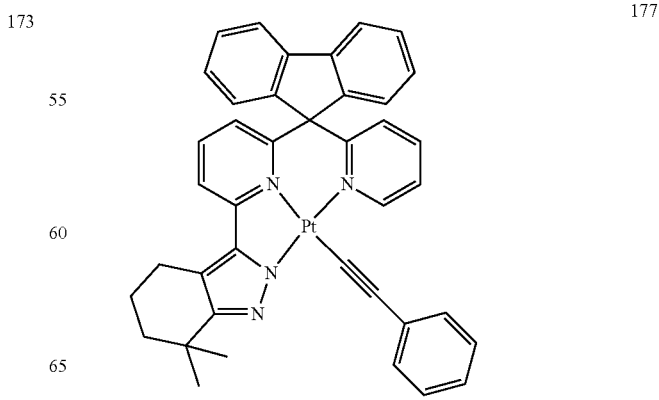

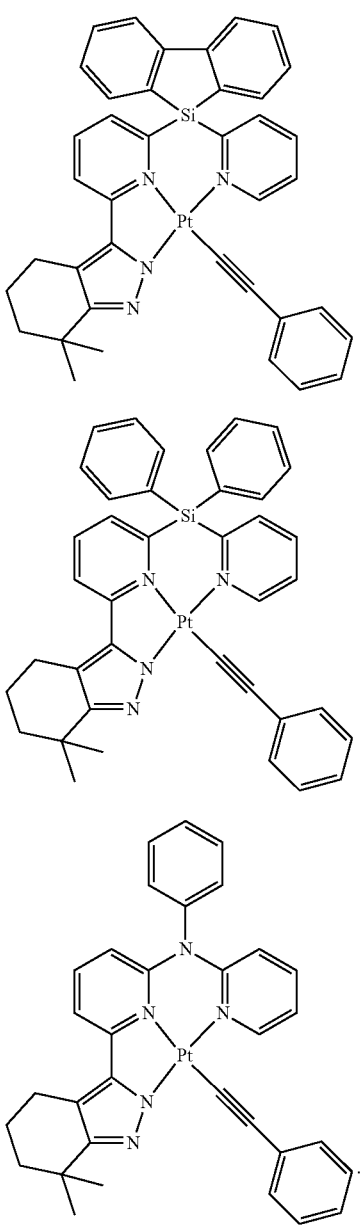

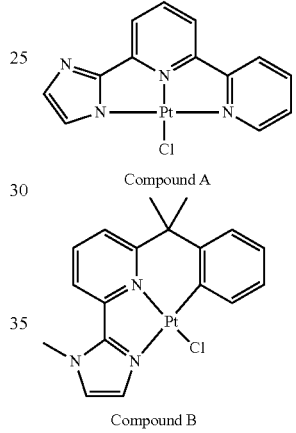

For example, the HOMO, LUMO, singlet (Si), and triplet (Ti) energy levels of the organometallic compounds above and Compounds A and B were evaluated by using Gaussian according to a density functional theory (DFT) method (structure optimization is performed at a degree of B3LYP, and 6-31G(d,p)). The results thereof are shown in Table 1.

TABLE 1

| Compound No. | HOMO (eV) | LUMO (eV) | $S_1$ energy level (eV) | $T_1$ energy level (eV) |
|---|---|---|---|---|
| 33 | −4.864 | −1.722 | 2.557 | 2.445 |
| 34 | −4.902 | −1.913 | 2.423 | 2.32 |
| 69 | −4.920 | −1.766 | 2.568 | 2.454 |
| 70 | −4.960 | −1.954 | 2.438 | 2.337 |
| 105 | −4.850 | −1.712 | 2.554 | 2.450 |
| 106 | −4.876 | −1.904 | 2.406 | 2.314 |
| 108 | −4.772 | −1.688 | 3.084 | 2.518 |
| 141 | −4.872 | −1.728 | 2.559 | 2.443 |
| 142 | −4.906 | −1.922 | 2.419 | 2.317 |
| 177 | −4.897 | −1.731 | 2.581 | 2.456 |
| 178 | −4.922 | −1.924 | 2.431 | 2.330 |
| A | −5.488 | −2.800 | 2.103 | 1.809 |
| B | −5.094 | −2.236 | 2.166 | 2.035 |

Compound A

Compound B

Referring to the results of Table 1, the organometallic compound of Formula 1 was found to have suitable electric characteristics as a dopant for use in an electron device, e.g., an organic light-emitting device.

Synthesis methods of the organometallic compound represented by Formula 1 may be recognizable by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer that is disposed between the first electrode and the second electrode, wherein the organic layer includes an emission layer and at least one organometallic compound represented by Formula 1.

The organic light-emitting device may have, due to the inclusion of an organic layer including the organometallic compound represented by Formula 1, low driving voltage, high efficiency, high power, high quantum efficiency, long lifespan, and excellent color coordination.

The organometallic compound of Formula 1 may be used between a pair of electrodes of an organic light-emitting Ligand $L_1$ in the organometallic compound represented by Formula 1 may be selected from ligands represented by Formula 2, provided that $T_2$ in Formula 2 is not a single bond. Hence, the organometallic compound represented by Formula 1 may emit light of a relatively short wavelength and have the highest occupied molecular orbital (HOMO) and the lowest unoccupied molecular orbital (LUMO) energy levels that are suitable in migration of charges. Therefore, the quality of an electron device, e.g., an organic light-emitting device that includes the organometallic compound may be excellent.

In addition, $Y_1$, $Y_2$, and $Y_3$ in Formula 2 are each nitrogen. Thus, the organometallic compound represented by Formula 1 may provide excellent emission efficiency, which lead to improved emission efficiency of an electron device, e.g., an organic light-emitting device, including the organometallic compound.

device. For example, the organometallic compound represented by Formula 1 may be included in the emission layer. In this regard, the organometallic compound may act as a dopant, and the emission layer may further include a host (that is, an amount of the organometallic compound represented by Formula 1 may be less than an amount of the host).

The expression that "(an organic layer) includes at least one of organometallic compounds" used herein may refer to an embodiment in which "(an organic layer) includes identical organometallic compounds represented by Formula 1" and to an embodiment in which "(an organic layer) includes two or more different organometallic compounds represented by Formula 1".

For example, the organic layer may include only Compound 1 as the organometallic compound. In this regard, Compound 1 may be included only in the emission layer of the organic light-emitting device. In various embodiments, the organic layer may include, as the organometallic compound, Compound 1 and Compound 2. In this regard, Compound 1 and Compound 2 may be included in an identical layer (for example, Compound 1 and Compound 2 both may be in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, in the organic light-emitting device, the first electrode may be an anode, the second electrode may be a cathode, and the organic layer may further include a hole transport region disposed between the first electrode and the emission layer and an electron transport region disposed between the emission layer and the second electrode, wherein the hole transport region may include a hole injection layer, a hole transport layer, an electron blocking layer, or any combinations thereof, and the electron transport region may include a hole blocking layer, an electron transport layer, an electron injection layer, or any combinations thereof.

The term "organic layer" as used herein refers to a single layer and/or a plurality of layers disposed between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device, according to an embodiment, will be described in connection with the FIGURE. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by vacuum depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). In various embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer or hole injection layer/hole transport layer/electron blocking layer, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201 below, and a compound represented by Formula 202 below:

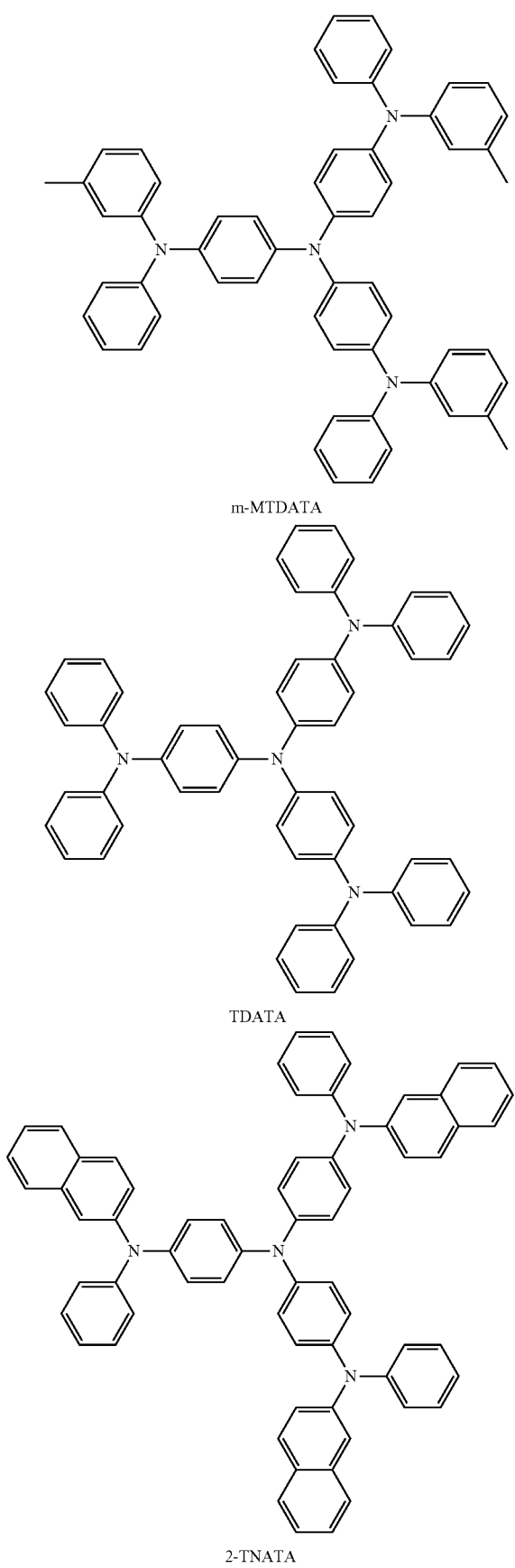
m-MTDATA
TDATA
2-TNATA
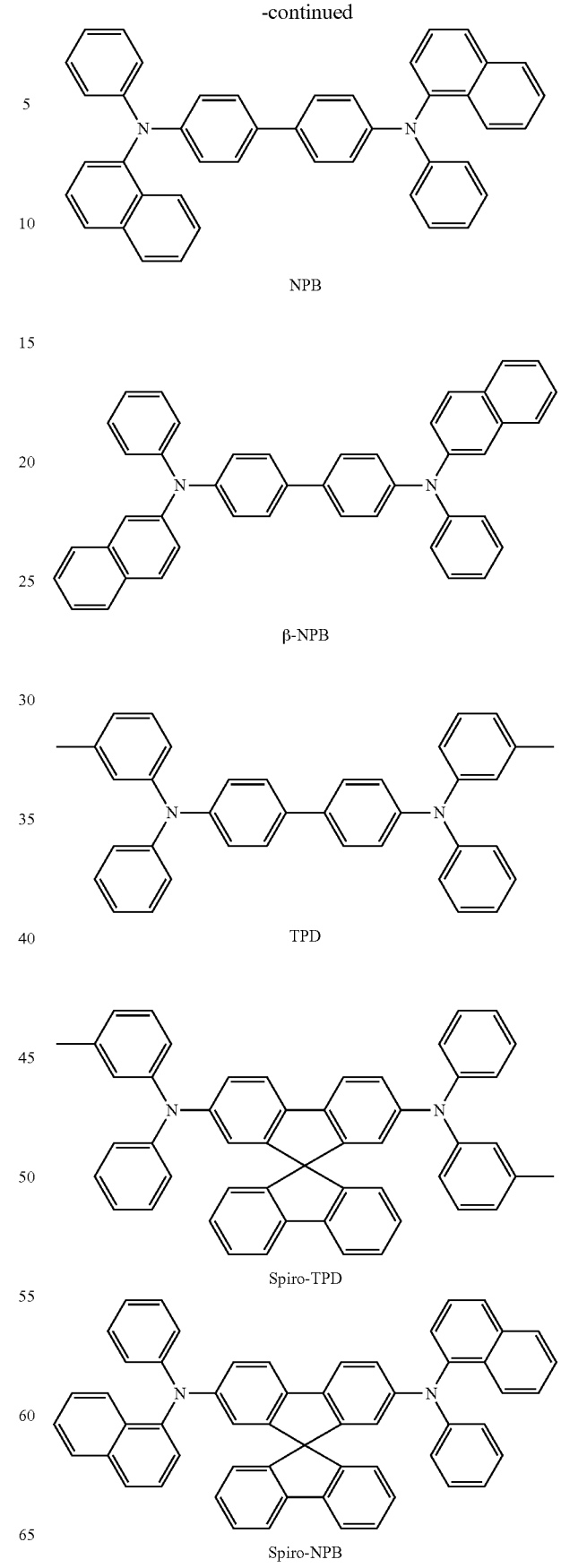
NPB
β-NPB
TPD
Spiro-TPD
Spiro-NPB

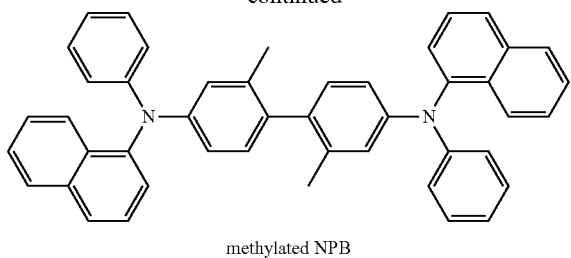

methylated NPB

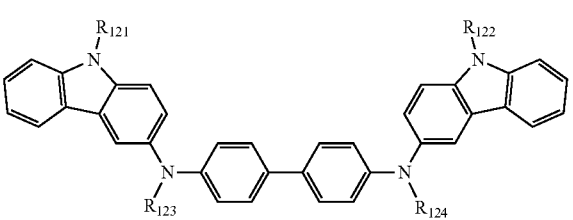

Formula 202

TAPC

HMTPD

Formula 201

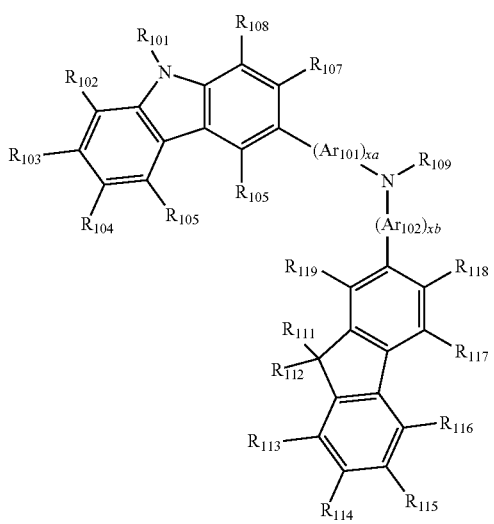

wherein in Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5. Alternatively, xa and xb may be each independently an integer selected from 0, 1, and 2. In some embodiments, xa may be 1 and xb may be 0, but embodiments are not limited thereto.

$R_{101}$ to $R_{108}$, $R_{111}$ to $R_{119}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from a phenyl group, a naphthyl group, an anthracenyl group, and a pyridinyl group; and a phenyl group, a naphthyl group, an anthracenyl group and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

Formula 201A

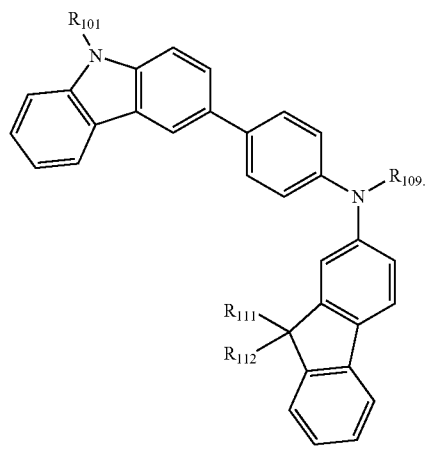

$R_{101}$, $R_{111}$, $R_{112}$, and $R_{109}$ in Formula 201A may be the same as those described herein.

For example, the compound represented by Formula 201 and the compound represented by Formula 202 may include Compounds HT1 to HT20, but embodiments are not limited thereto:

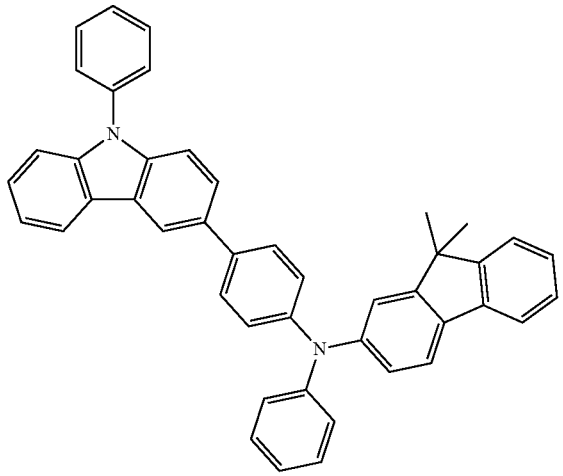

HT1

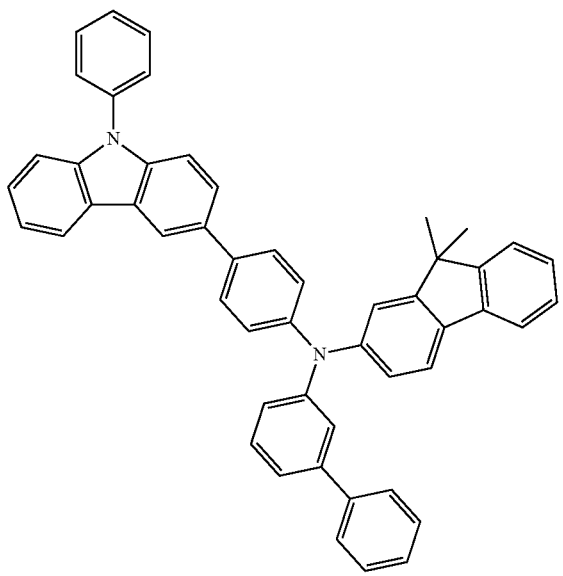

HT2

119
-continued
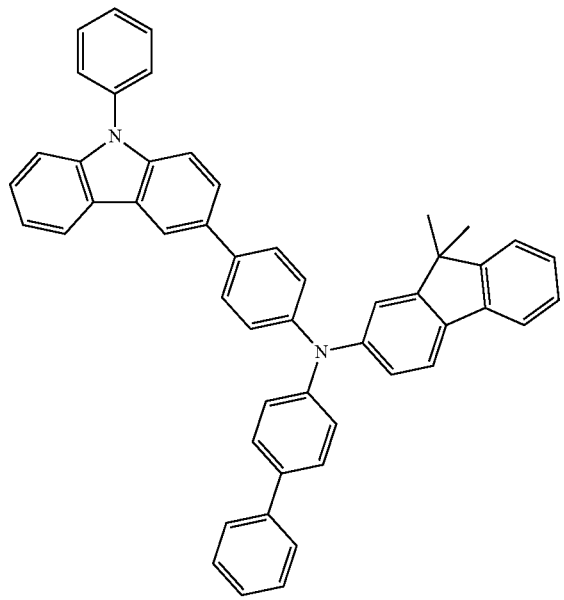
HT3
120
-continued
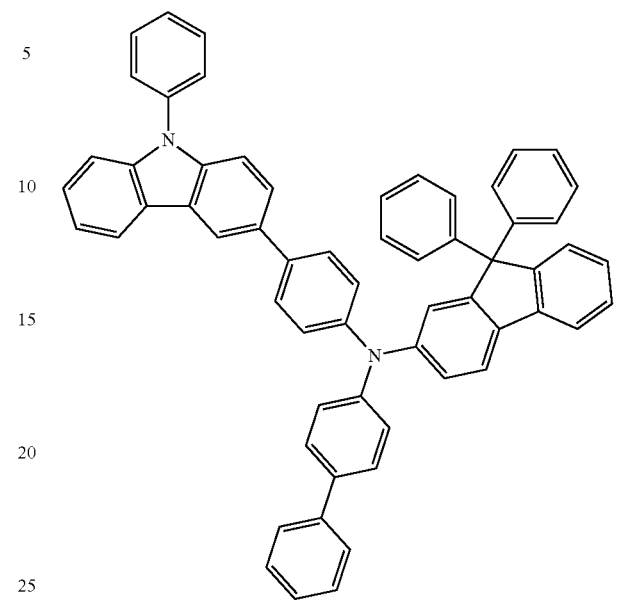
HT5
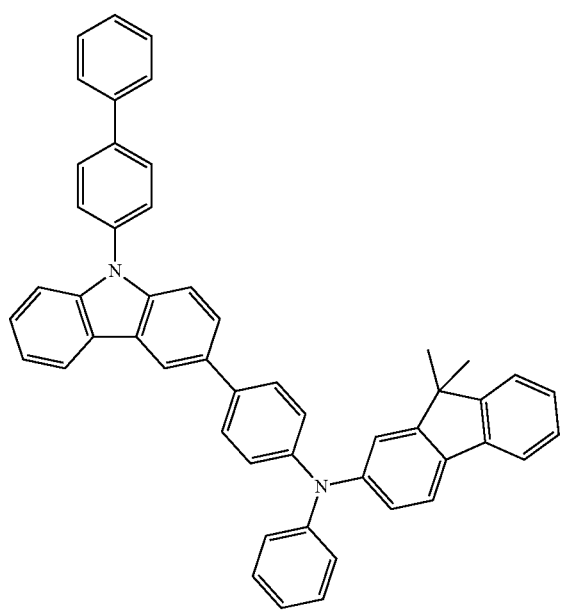
HT4
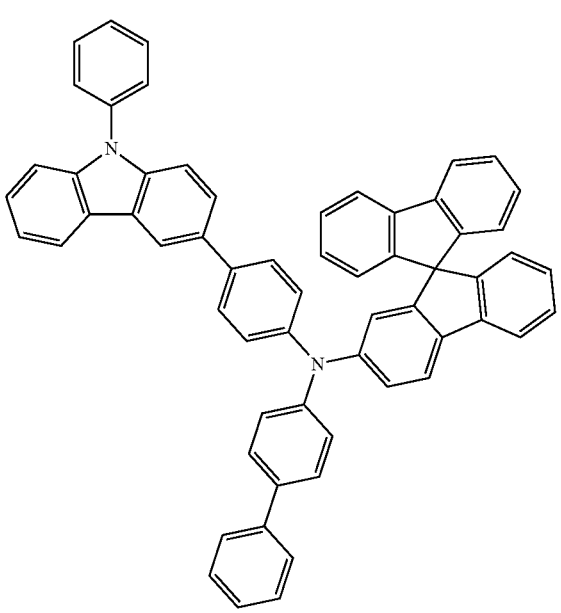
HT6

121 -continued
HT7
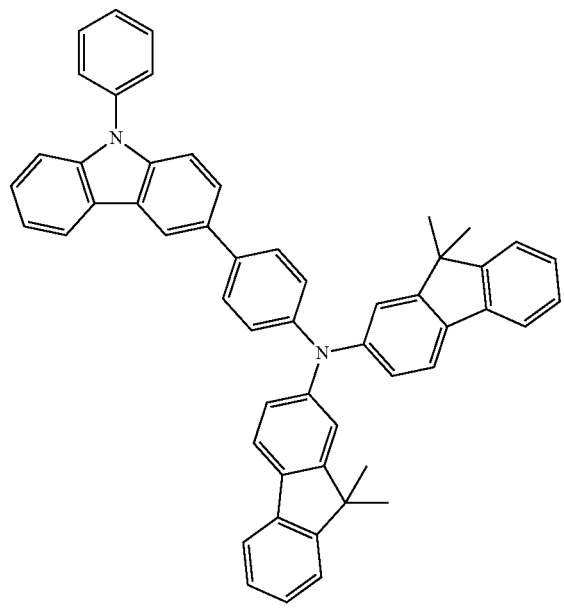
HT8
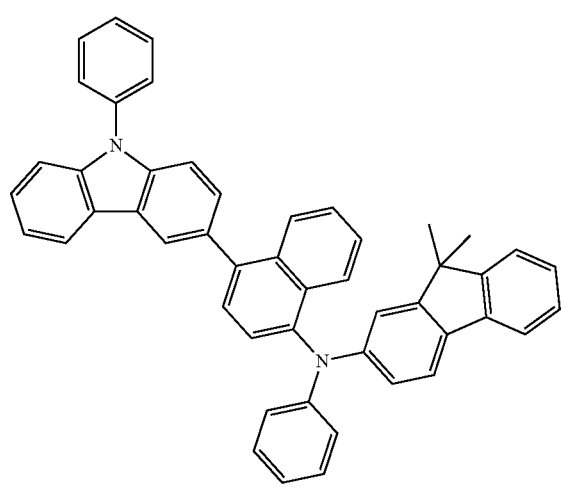
122 -continued
HT9
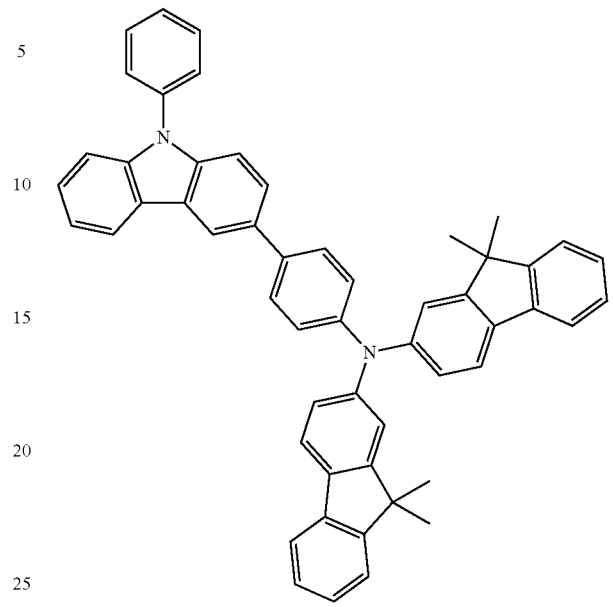
HT10
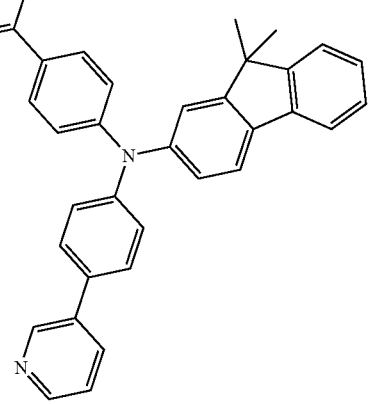

HT11
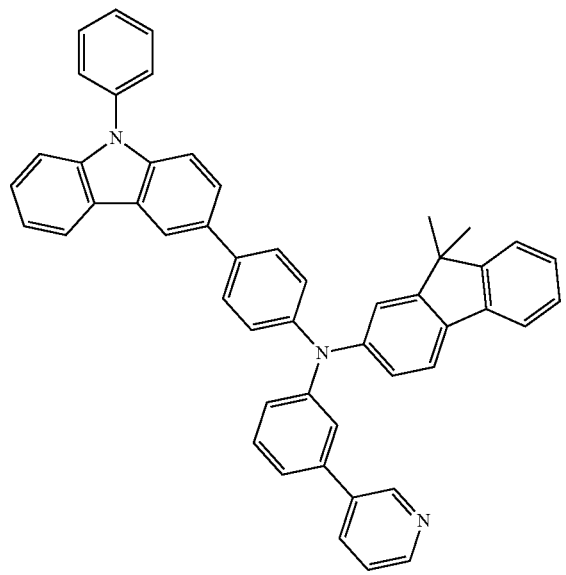
HT12
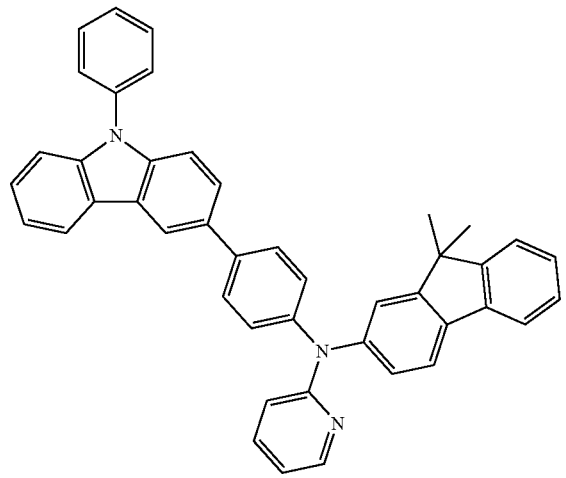
HT13
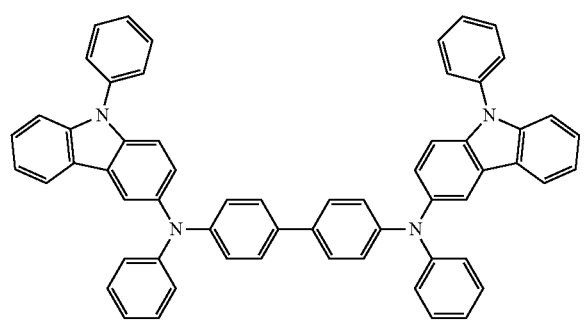
HT14
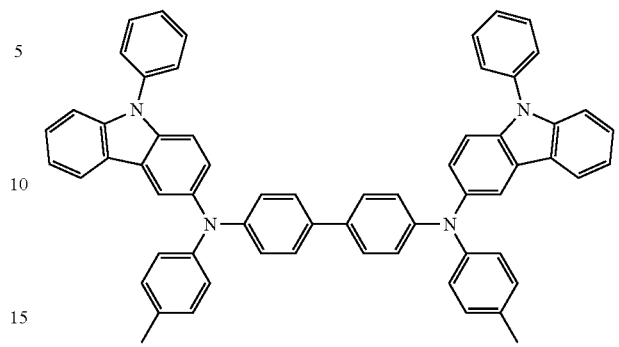
HT15
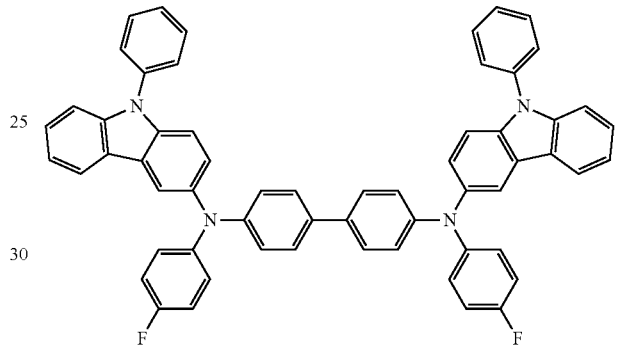
HT16
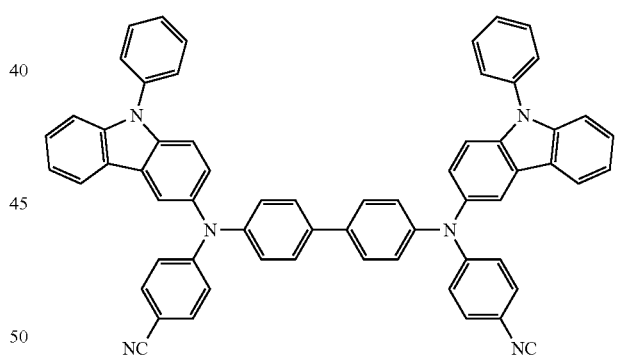
HT17
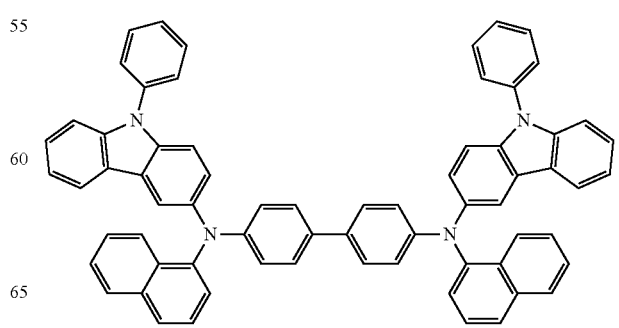

-continued

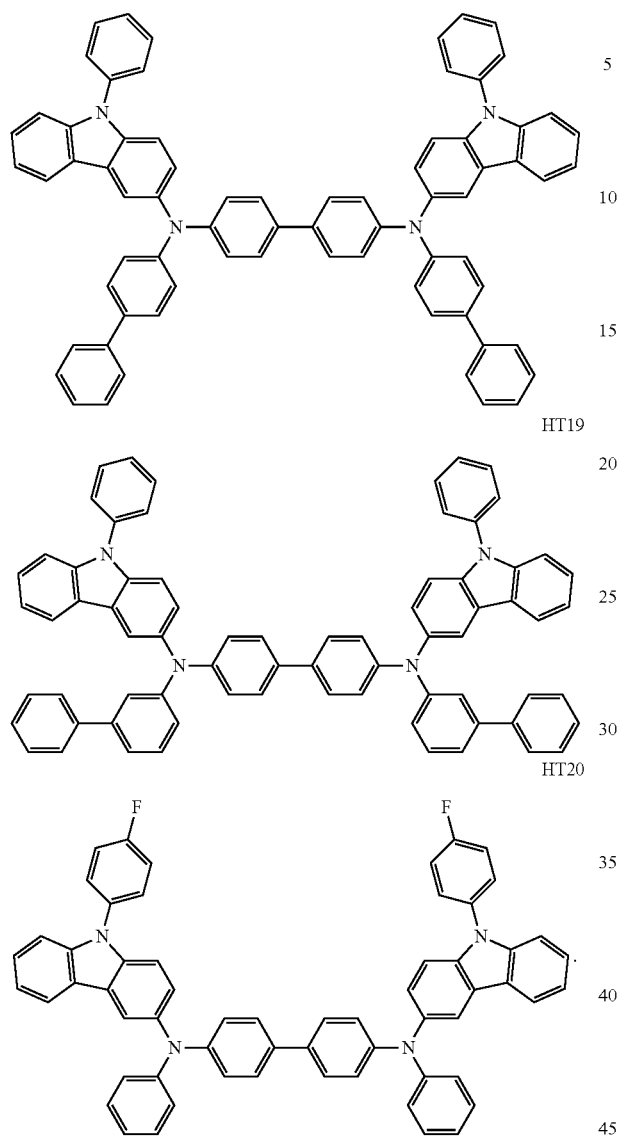

HT18

HT19

HT20

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about, 100 Å to about 1,500 Å. While not wishing to be bound by theory, it is understood that when the thickness values of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 below, but are not limited thereto:

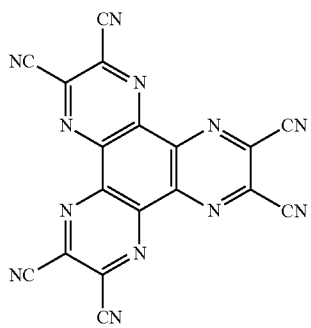

Compound HT-D1

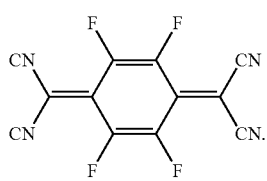

F4-TCNQ

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

Meanwhile, when the hole transport region includes an electron blocking layer, a material for the electron blocking layer may be selected from materials for the hole transport region described above and materials for a host to be explained later.

However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

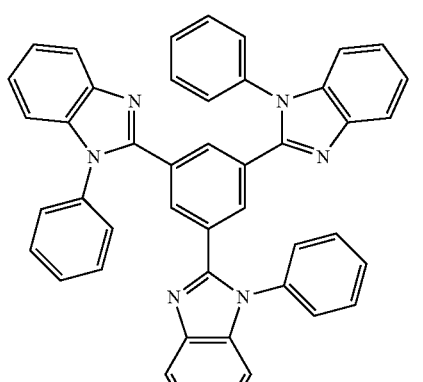
TPBi
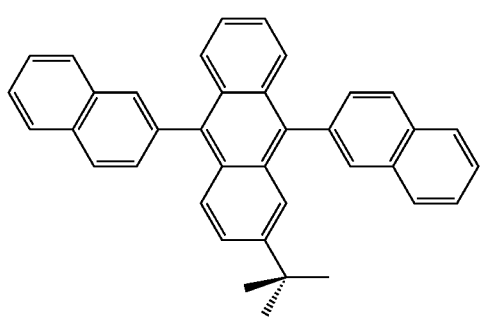
TBADN
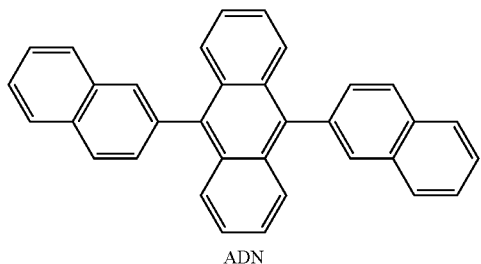
ADN
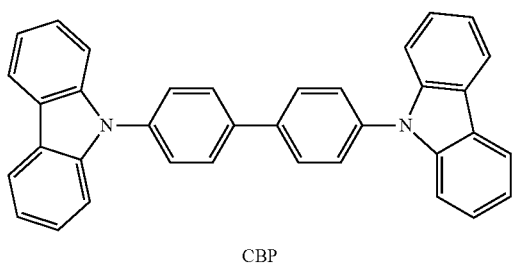
CBP
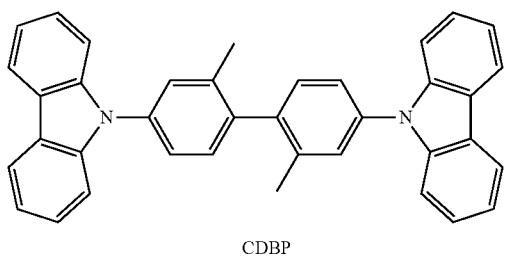
CDBP
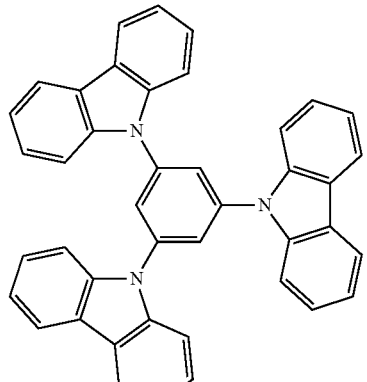
TCP
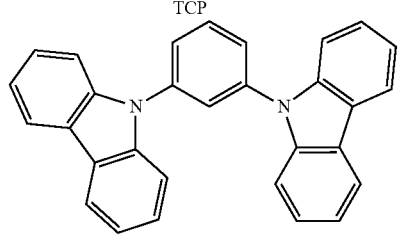
mCP
Compound H50
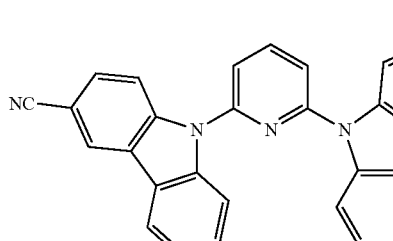
Compound H51
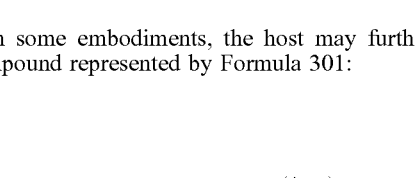
In some embodiments, the host may further include a compound represented by Formula 301:
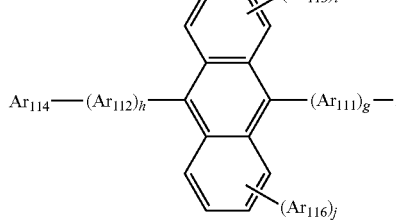
Formula 301
wherein, in Formula 301, $Ar_{111}$ and $Ar_{112}$ may be each independently selected from
a phenylene group, a naphthylene group, a phenanthrenylene group, and a pyrenylene group; and a phenyl group, a phenylene group substituted with at least one selected from a naphthyl group and an anthracenyl group, a naphthylene group, a phenanthrenylene group, and a pyrenylene group.

$Ar_{113}$ to $Ar_{116}$ in Formula 301 may be each independently selected from a $C_1$-$C_{10}$ alkyl group, a phenyl group, a naphthyl group, a phenanthrenyl group, and a pyrenyl group; and a phenyl group, a phenyl group substituted with at least one selected from a naphthyl group and an anthracenyl group, a naphthyl group, a phenanthrenyl group, and a pyrenyl group.

g, h, i, and j in Formula 301 may be each independently an integer selected from 0 to 4, for example, 0, 1, or 2.

$Ar_{113}$ to $Ar_{116}$ in Formula 301 may be each independently selected from a $C_1$-$C_{10}$ alkyl group substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

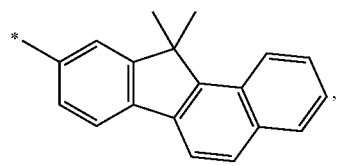

but embodiments are not limited thereto.

In some embodiments, the host may include a compound represented by Formula 302:

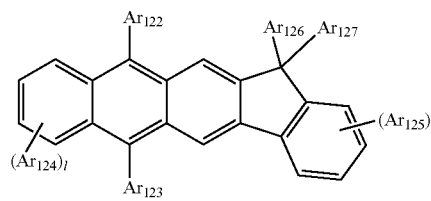

Formula 302

$Ar_{122}$ to $Ar_{125}$ in Formula 302 may be the same as described herein in connection with $Ar_{113}$ in Formula 301.

$Ar_{126}$ and $Ar_{127}$ in Formula 302 may be each independently a $C_1$-$C_{10}$ alkyl group, e.g., a methyl group, an ethyl group, or a propyl group.

k and l in Formula 302 may be each independently an integer selected from 0 to 4. In some embodiments, k and l may each be 0, 1, or 2.

In some embodiments, the compound represented by Formula 301 and the compound represented by Formula 302 may include Compounds HT1 to HT42, but embodiments are not limited thereto:

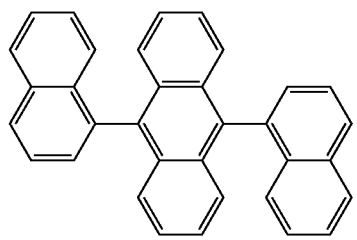

H1

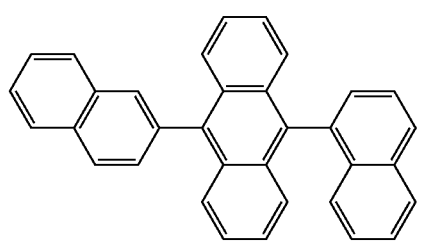

H2

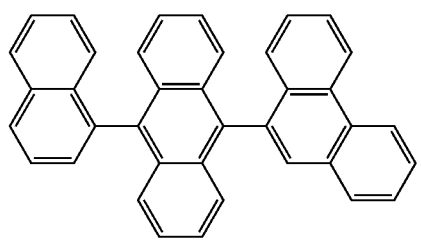

H3

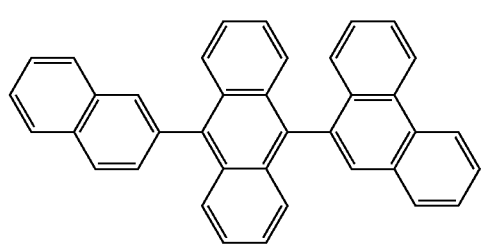

H4

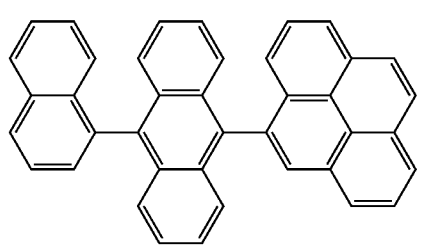

H5

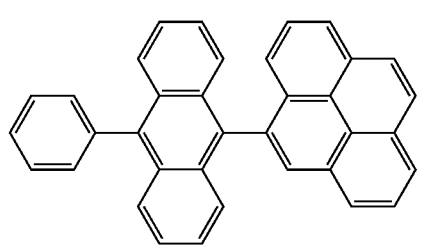

H6

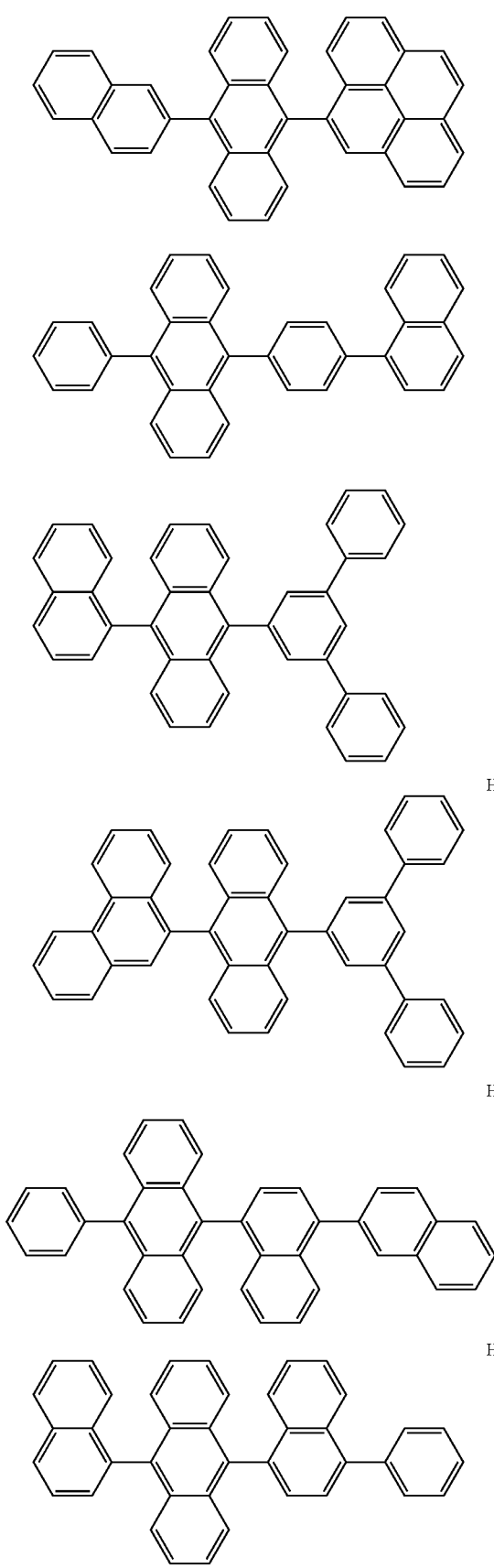

H18
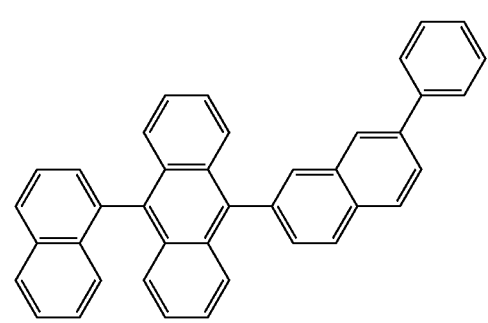
H19
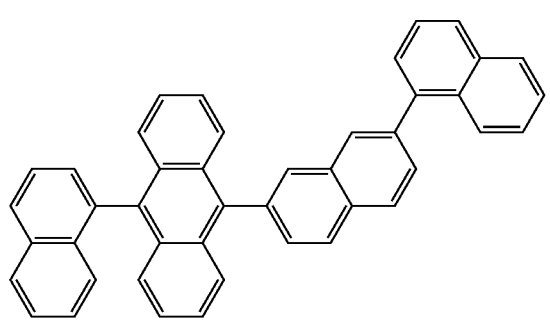
H20
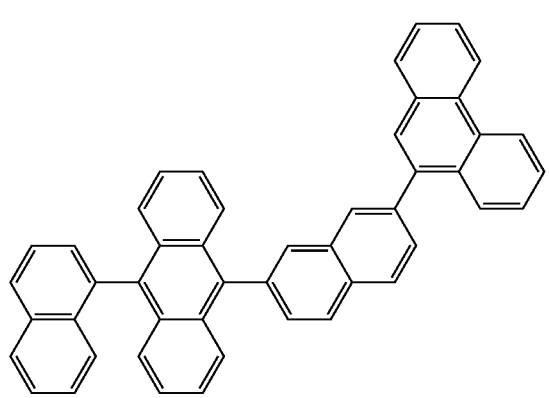
H21
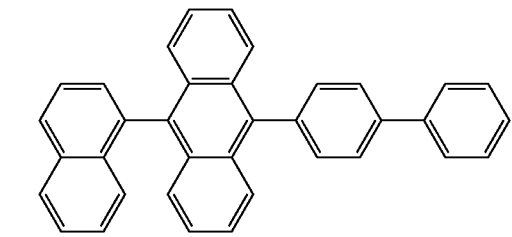
H22
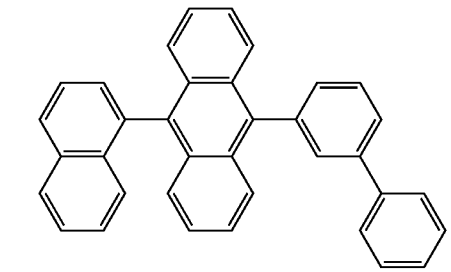
H23
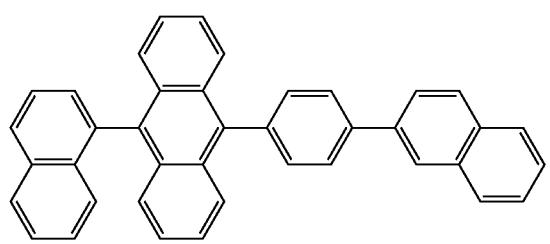
H24
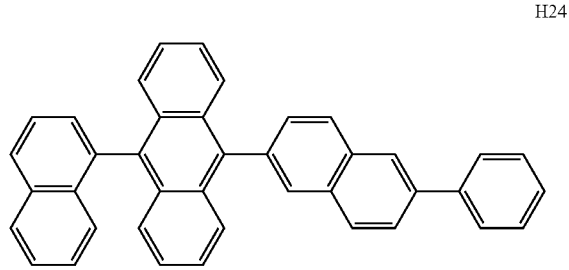
H25
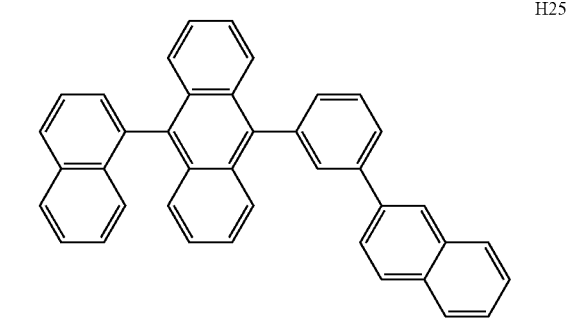
H26
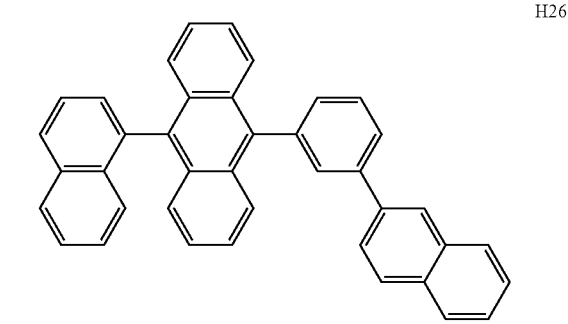
H27
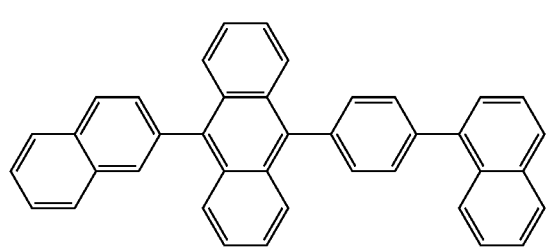

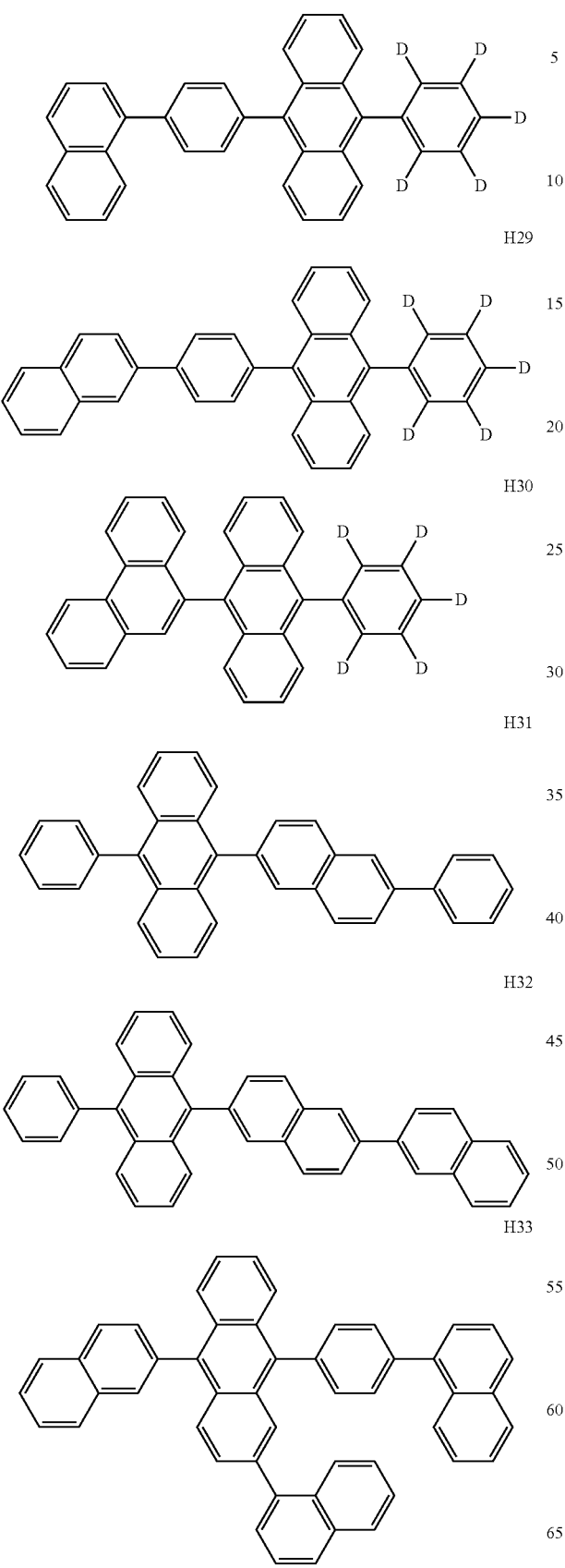

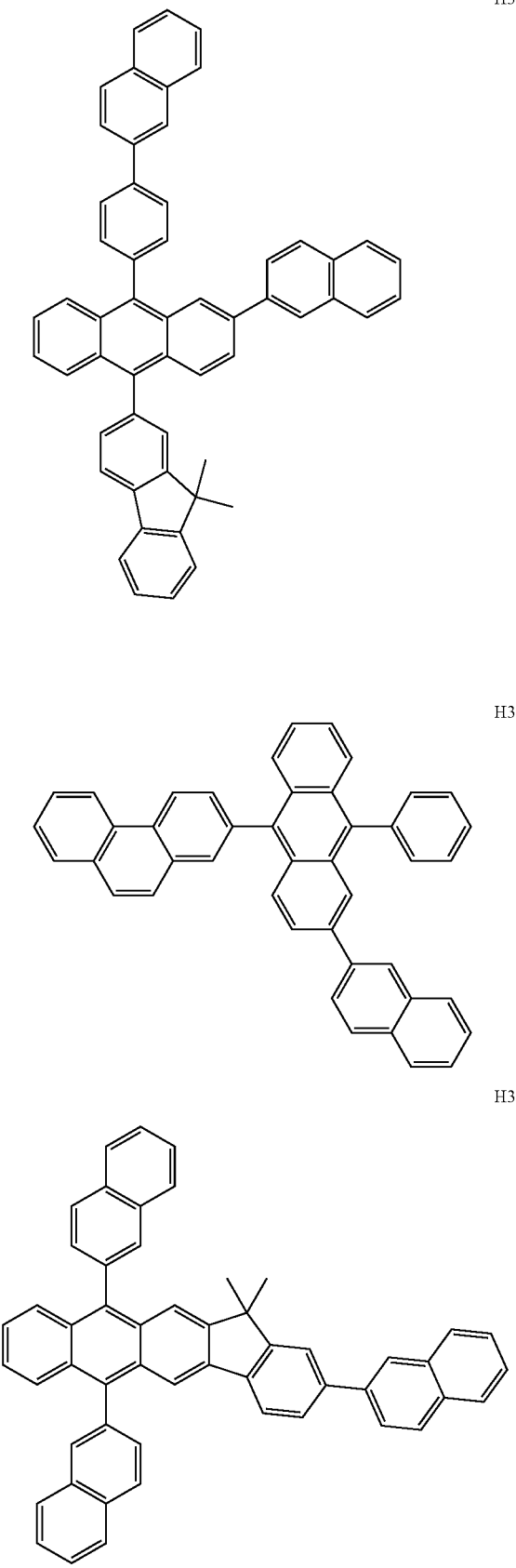

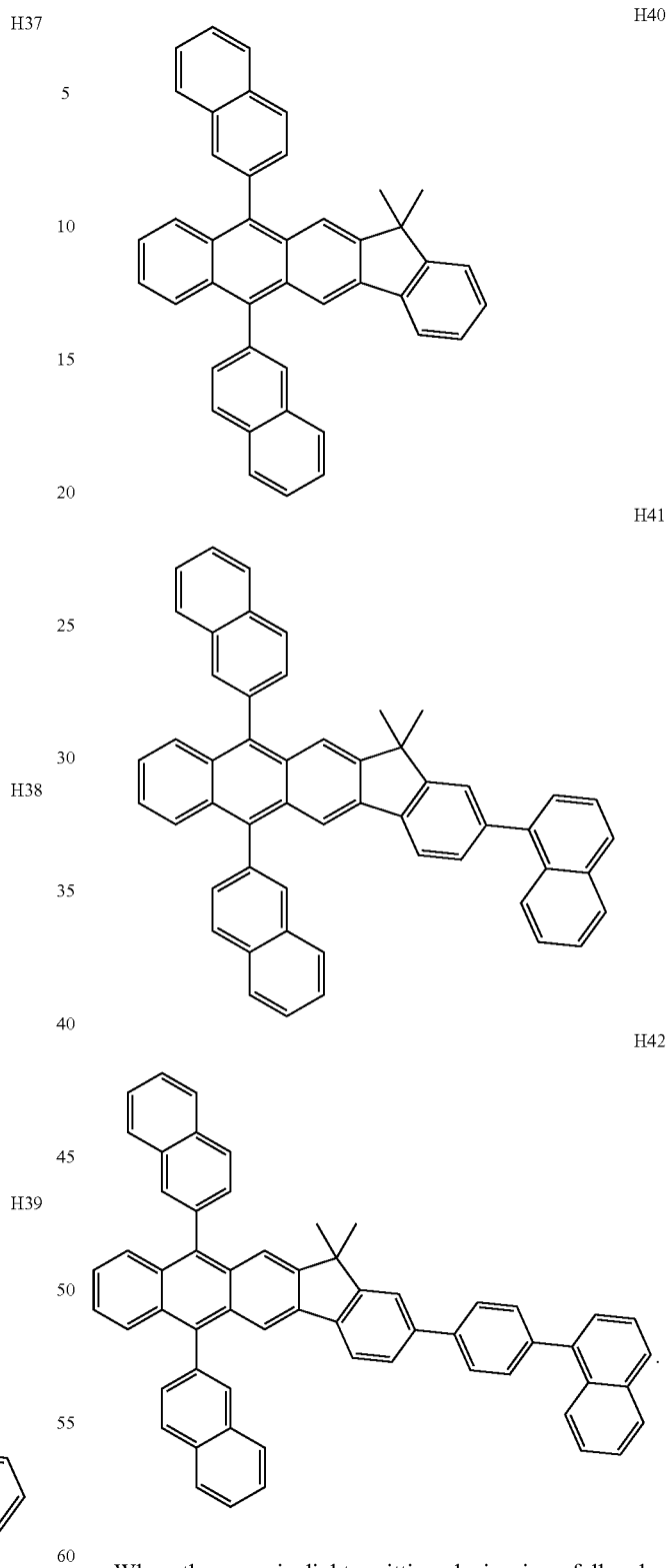

When the organic light-emitting device is a full color organic light-emitting device, the emission layer may be patterned into a red emission layer, a green emission layer, and a blue emission layer. In various embodiments, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq but is not limited thereto:

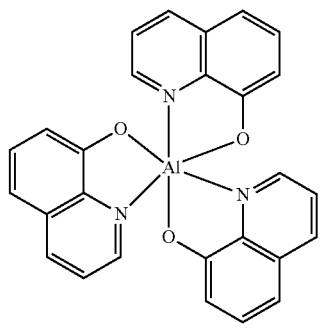

Alq$_3$

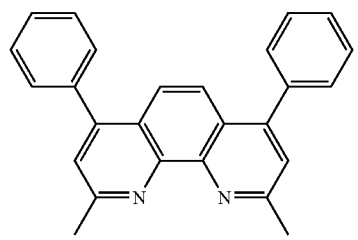

BCP

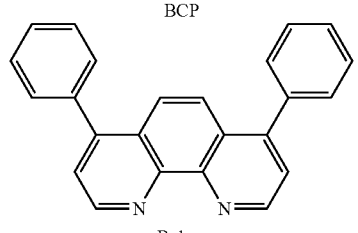

Bphen

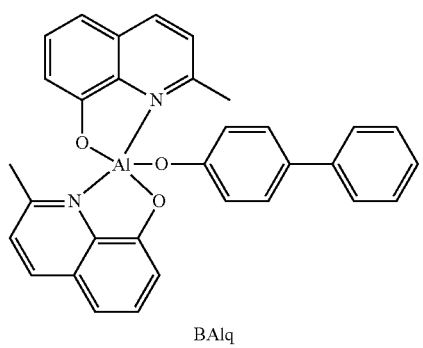

BAlq

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include at least one selected from BCP, Bphen, Alq$_3$, BAlq, TAZ, and NTAZ:

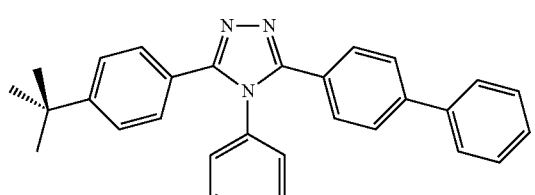

TAZ

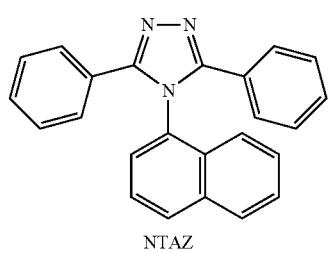

NTAZ

In various embodiments, the electron transport layer may include at least one of ET1 and ET2, but are not limited thereto:

ET1

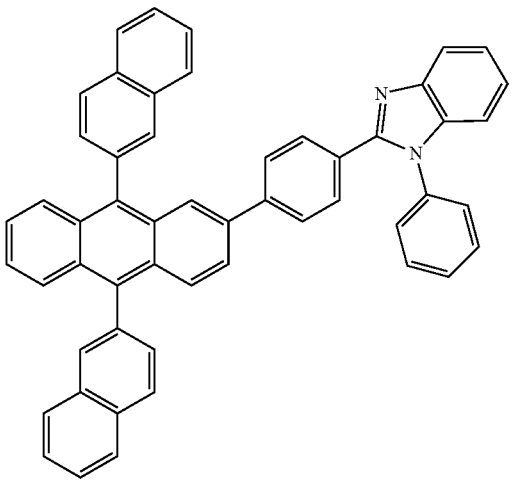

ET2

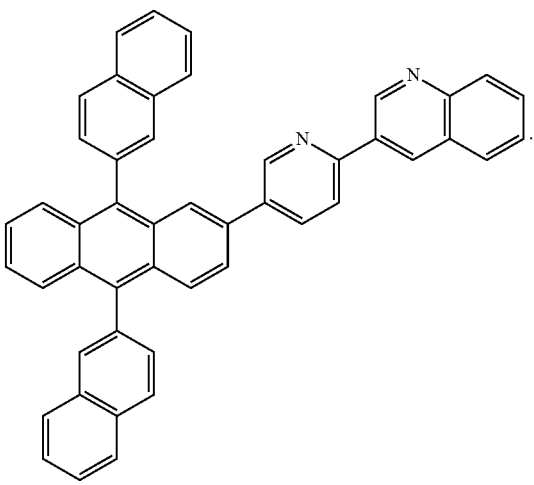

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

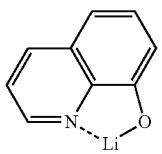

ET-D2

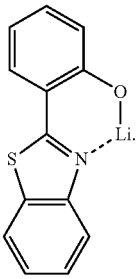

The electron transport region may include an electron injection layer that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the ranges described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission-type light-emitting device, a transmissive electrode formed using ITO or IZO may be used as the second electrode 19.

Hereinbefore, the organic light-emitting device has been described with reference to the FIGURE, but is not limited thereto.

Hereinbefore, the organic light-emitting device has been described with reference to the FIGURE, but is not limited thereto.

According to an aspect of another embodiment, there is provided a composition for diagnosing that includes at least one organometallic compound represented by Formula 1.

Since the organometallic compound represented by Formula 1 may provide high emission efficiency, the diagnostic efficiency of the composition for diagnosing that includes the organometallic compound represented by Formula 1 may be excellent.

The composition for diagnosing may be used in various manners, such as in a diagnostic kit, a diagnostic reagent, a biosensor, or a biomarker.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an iso-propyloxy (iso-propoxy) group.

The term "$C_2$-$C_{60}$ alkenyl group" as used herein refers to a group formed by including at least one carbon-carbon double bond in the middle or at the terminal of the $C_2$-$C_{60}$ alkyl group, and detailed examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by including at least one carbon-carbon triple bond in the middle or at the terminal of the $C_2$-$C_{60}$ alkyl group, and detailed examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si, and S as a ring-forming atom and 1 to 10 carbon atoms, and non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and which is not aromatic. Non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Non-limiting examples of the $C_1$-$C_{10}$ heterocycloalkenyl group include a 2,3-dihydrofuranyl group and a 2,3-dihydrothiophenyl group. The term "$C_1$-$C_{10}$ heterocycloalkenylene group," as used herein, refers to a divalent group having the same structure as the $C_1$-$C_{10}$ heterocycloalkenyl group.

The term "$C_6$-$C_{60}$ aryl group" as used herein refers to a monovalent group having an aromatic system having 6 to 60 carbon atoms, and the term "$C_6$-$C_{60}$ arylene group" as used herein refers to a divalent group having an aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a cyclic aromatic system that has at least one heteroatom selected from N, O, P, Si, and S as a ring-forming atom, and 1 to 60 carbon atoms. The term "$C_1$-$C_{60}$ heteroarylene group" as used herein refers to a divalent group having an aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group (e.g., having 8 to 60 carbon atoms) that has two or more rings condensed to each other, only carbon atoms as a ring-forming atom, and which is non-aromatic in the entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) that has two or more rings condensed to each other, has a heteroatom selected from N, O, P, and S, other than carbon atoms, as a ring-forming atom, and which is non-aromatic in the entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

At least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1: Synthesis of Compound 33

Synthesis of Intermediate A3

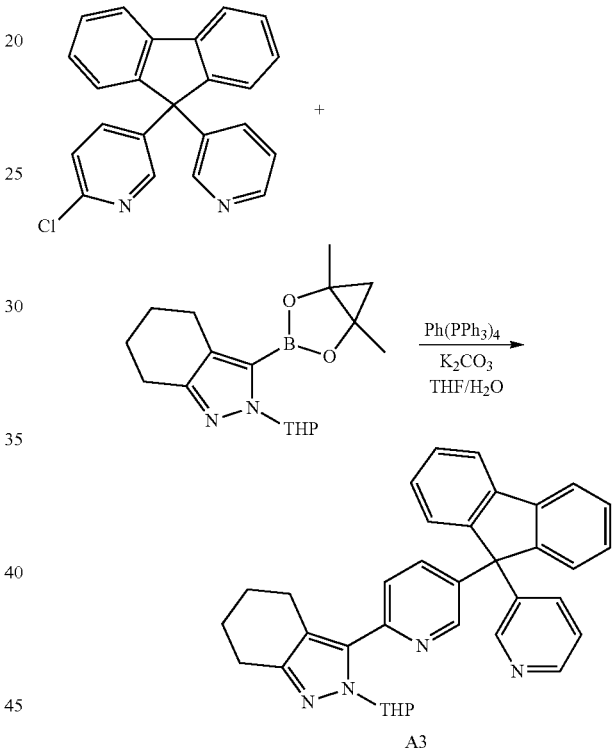

5 grams (g) (14.1 millimoles, mmol) of 2-chloro-5-(9-(pyridin-3-yl)-9H-fluoren-9-yl)pyridine, 5.35 g (16.9 mmol) of 3-(1,5-dimethyl-2,4-dioxa-3-borabicyclo[3.1.0]hexan-3-yl)-2-(tetrahydro-2H-pyran-2-yl)-4,5,6,7-tetrahydro-2H-indazole, 1.14 g (1.0 mmol) of Pd(PPh$_3$)$_4$, and 3.89 g (28.2 mmol) of K$_2$CO$_3$ were mixed together with 60 milliliters (mL) of tetrahydrofuran (THF) and 30 mL of water (H$_2$O). The mixture was stirred at a temperature of about 75° C. for about 18 hours. The temperature was then lowered to room temperature, followed by filtering of the mixture. An organic layer was extracted from the resultant using methylene chloride (MC), and an anhydrous magnesium sulfate (MgSO$_4$) was added thereto to dry the organic layer. The resultant was filtered and a solvent in the obtained filtrate was removed under reduced pressure. The residual was purified by column chromatography using ethyl acetate (EA) and hexane at a ratio of 10:90 to obtain 5.03 g (81%) of Intermediate A3.

Synthesis of Intermediate A2

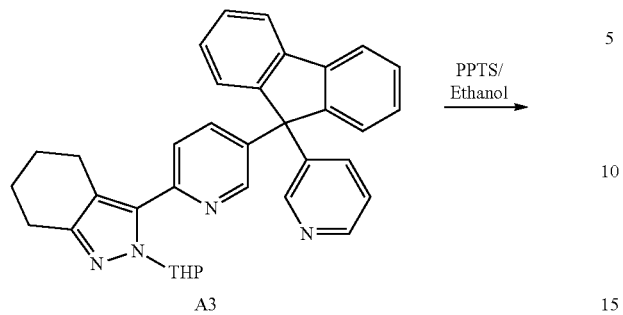

A3

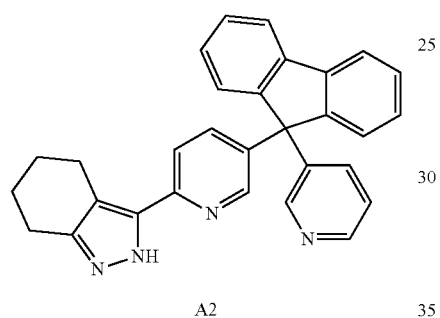

A2

5.03 g (11.4 mmol) of Intermediate A3 and 1.20 g (5.7 mmol) of pyridinium p-toluenesulfonate (PPTS) were mixed together with 100 mL of ethanol. The mixture was stirred at a temperature of about 78° C. for about 12 hours. The temperature was then lowered to room temperature, followed by filtering of the mixture. An organic layer was extracted from the resultant using MC, and an anhydrous magnesium sulfate ($MgSO_4$) was added thereto to dry the organic layer. The resultant was filtered and a solvent in the obtained filtrate was removed under reduced pressure. The residual was purified by column chromatography using EA, hexane, and methanol at a ratio of 24:75:1 to obtain 3.17 g (75%) of Intermediate A2.

Synthesis of Intermediate A1

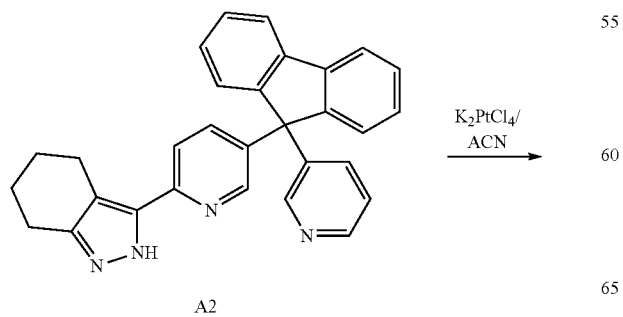

A2

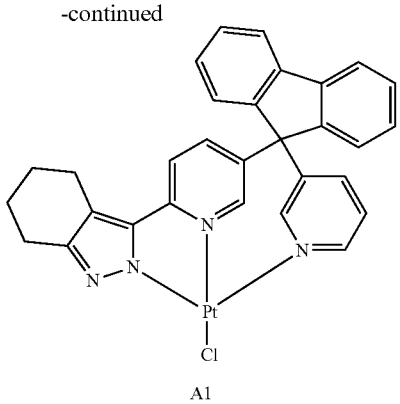

A1

3.1 g (7.04 mmol) of Intermediate $A_2$ and 2.92 g (7.04 mmol) of $K_2PtCl_4$ were mixed together with 60 mL of acetonitrile (ACN). The mixture was stirred at a temperature of about 100° C. for about 24 hours to carry out the reaction. Thereafter, the temperature was lowered. The mixture obtained therefrom was filtered to obtain a solid. The solid was thoroughly washed with methanol and water and dried to obtain 2.83 g (60%) of Intermediate A1.

Synthesis of Compound 33

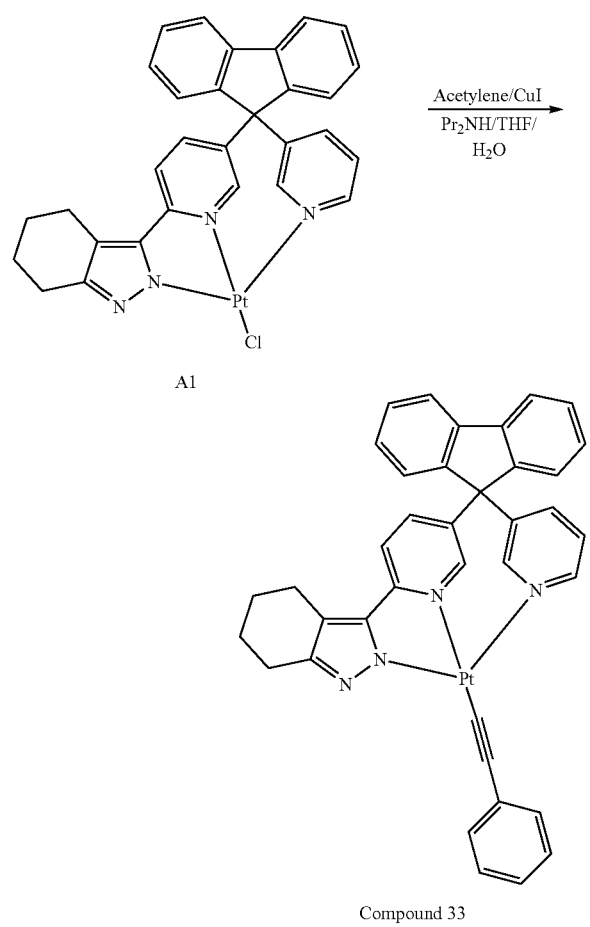

2.8 g (4.18 mmol) of Intermediate A1, 0.51 g (5.01 mmol) of acetylene, 0.04 g (0.21 mmol) of CuI, and 1.27 g (12.54 mmol) of diisopropylamine were mixed together with 40 mL of THF and 20 mL of water. The mixture was stirred at a temperature of about 85° C. for about 24 hours to carry out reaction. Thereafter, the temperature was lowered. The mixture obtained therefrom was filtered to obtain a solid. The solid was thoroughly washed with ethanol and was subsequently purified by column chromatography using ethanol and hexane at a ratio of about 20:80 to obtain 1.08 g (35%) of Compound 33. The identity of the obtained compound was confirmed by using mass spectroscopy and high-performance liquid chromatography (HPLC) analysis.

HRMS(MALDI) calcd for $C_{38}H_{28}N_4Pt$: m/z 735.1962, Found: 735.1960.

Synthesis Example 2: Synthesis of Compound 34

Synthesis of Intermediate B3

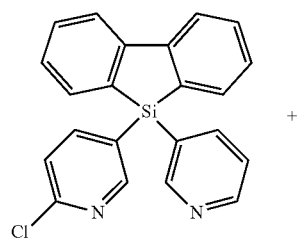

+

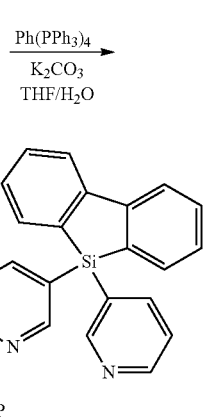

$\xrightarrow{\text{Ph(PPh}_3)_4}_{\text{K}_2\text{CO}_3}_{\text{THF/H}_2\text{O}}$

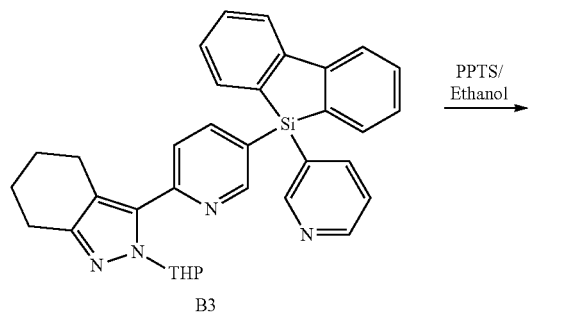

B3

5.54 g (76%) of Intermediate B3 was obtained in the same manner as Intermediate A3 in Synthesis Example 1, except that 5.0 g (13.5 mmol) of 2-chloro-5-(5-(pyridin-3-yl)-5H-dibenzo[b,d]silol-5-yl)pyridine was used instead of 2-chloro-5-(9-(pyridin-3-yl)-9H-fluoren-9-yl)pyridine.

Synthesis of Intermediate B2

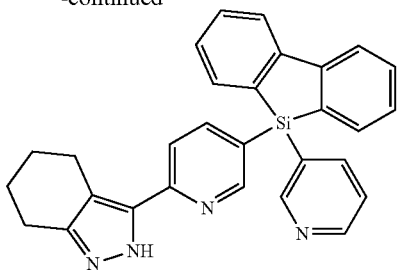

B2

4.02 g (86%) of Intermediate B2 was obtained in the same manner as Intermediate A2 in Synthesis Example 1, except that 5.54 g (10.2 mmol) of Intermediate B3 was used instead of Intermediate A3.

Synthesis of Intermediate B1

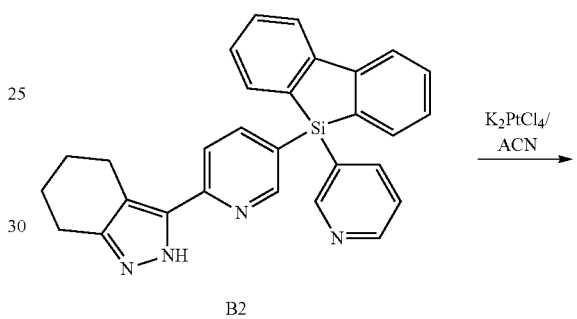

B2

$\xrightarrow{\text{K}_2\text{PtCl}_4/\text{ACN}}$

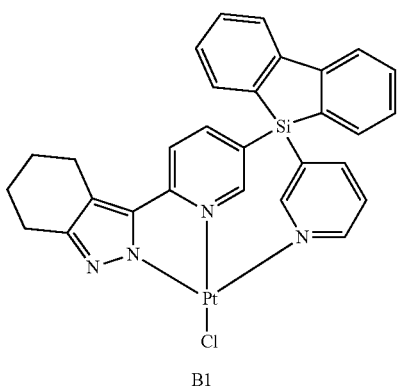

B1

3.31 g (55%) of Intermediate B1 was obtained in the same manner as Intermediate A1 in Synthesis Example 1, except that 4.00 g (8.76 mmol) of Intermediate B2 was used instead of Intermediate A2.

151

Synthesis of Compound 34

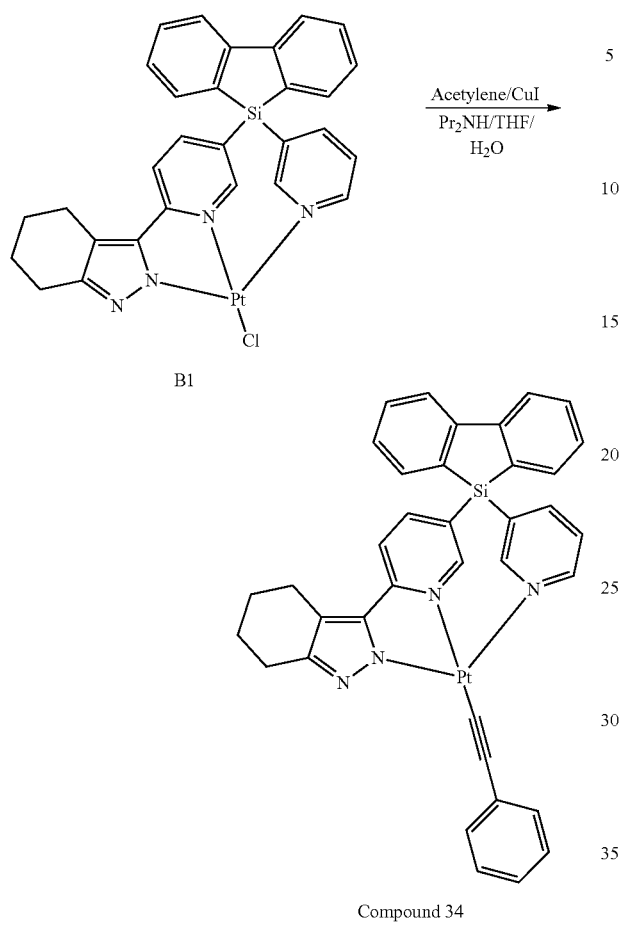

Compound 34

1.12 g (31%) of Compound 34 was obtained in the same manner as Compound 33 in Synthesis Example 1, except that 3.30 g (4.81 mmol) of Intermediate B1 was used instead of Intermediate A1. The identity of the obtained compound was confirmed by using mass spectroscopy and HPLC analysis.

HRMS(MALDI) calcd for $C_{37}H_{28}N_4PtSi$: m/z 751.8280, Found: 751.8278.

Example 1

An ITO glass substrate was cut to a size of 50 millimeters (mm)×50 mm×0.5 mm. Then the glass substrate was sonicated in acetone iso-propyl alcohol and pure water for about 15 minutes in each solvent, and cleaned by exposure to ultraviolet rays with ozone for 30 minutes.

Then, a hole injection layer was formed on an ITO electrode (anode) that is on the glass substrate by vacuum-depositing m-MTDATA at a deposition rate of about 1 Angstrom per second (Å/sec) to have a thickness of about 600 Å. A hole transport layer was formed on the hole injection layer by vacuum-depositing α-NPD at a deposition rate of about 1 Å/sec to have a thickness of about 250 Angstroms (Å).

An emission layer was formed on the hole transport layer by co-depositing Compound 33 (dopant) and CBP (host) at a deposition rate of about 0.1 Å/sec and 1 Å/sec, respectively, to have a thickness of about 400 Å.

152

A hole blocking layer was formed on the emission layer by vacuum-depositing BAlq at a deposition rate of 1 Å/sec to have a thickness of about 50 Å. The electron transport layer was formed on the hole blocking layer by vacuum-depositing $Alq_3$ to have a thickness of about 300 Å. An electron injection layer was formed on the electron transport layer by vacuum-depositing LiF to have a thickness of about 10 Å. A second electrode (cathode) was formed on the electron injection layer by vacuum-depositing Al to have a thickness of about 1,200 Å. Accordingly, the manufacture of an organic light-emitting device was completed, in which the organic light-emitting device included a structure of ITO/m-MTDATA (600 Å)/α-NPD (250 Å)/CBP+10% (Compound 33) (400 Å)/BAlq (50 Å)/$Alq_3$ (300 Å)/LiF (10 Å)/Al (1,200 Å).

Examples 2 and Comparative Examples 1 and 2

An organic light-emitting device was manufactured in the same manner as in Example 1, except that the compounds listed in Table 2 were used instead of Compound 33 as a dopant in the formation of the emission layer.

Evaluation Example 1: Evaluation of Characteristics of Organic Light-Emitting Device The driving voltage, emission efficiency, power efficiency, color-coordination, quantum efficiency, and lifespan ($T_{95}$) of the organic light-emitting devices manufactured in Examples 1 and 2 and Comparative Examples 1 and 2 were evaluated. The results thereof are shown in Table 2. A Keithley 2400 current voltmeter and a luminance meter (Minolta Cs-1000A) were used in the evaluation. The lifespan ($T_{95}$) refers to time required for the initial luminance of 6,000 nit of the organic light-emitting device to reduce by 95%.

TABLE 2

| | Dopant | Driving voltage (V) | Emission Efficiency (cd/A) | Power Efficiency (lm/W) | CIEx | CIEy | Quantum efficiency (%) | Lifespan (hr) ($T_{95}$) |
|---|---|---|---|---|---|---|---|---|
| Example 1 | Compound 33 | 5.0 | 47.8 | 29.1 | 0.369 | 0.602 | 17.2 | 180 |
| Example 2 | Compound 34 | 5.2 | 45.2 | 28.0 | 0.363 | 0.598 | 16.5 | 185 |
| Comparative Example 1 | Compound A | 6.9 | 20.1 | 13.4 | 0.390 | 0.623 | 8.3 | 63 |
| Comparative Example 2 | Compound B | 6.8 | 25.2 | 15.1 | 0.386 | 0.635 | 9.2 | 50 |

TABLE 2-continued

| Dopant | Driving voltage (V) | Emission Efficiency (cd/A) | Power Efficiency (lm/W) | CIEx | CIEy | Quantum efficiency (%) | Lifespan (hr) ($T_{95}$) |
|---|---|---|---|---|---|---|---|

Compound 33

Compound 34

Compound A

Compound B

Referring to Table 2, it was found that the organic light-emitting devices manufactured in Examples 1 and 2 had excellent driving voltage, emission efficiency, power efficiency, color-coordination, quantum efficiency, and lifespan characteristics, as compared with the organic light-emitting devices of Comparative Examples 1 and 2.

The organometallic compound has excellent electric characteristics and thermal stability. Accordingly, an organic light-emitting device using the organometallic compound has a low driving voltage, high emission efficiency, high power efficiency, high color coordination, and excellent lifespan characteristics. Further, a composition for diagnosing including the organometallic compound may have high diagnostic efficiency, since the organometallic compound has excellent phosphorescent emission characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. An organometallic compound represented by Formula 1:

$$M(L_1)(L_2) \quad \text{Formula 1}$$

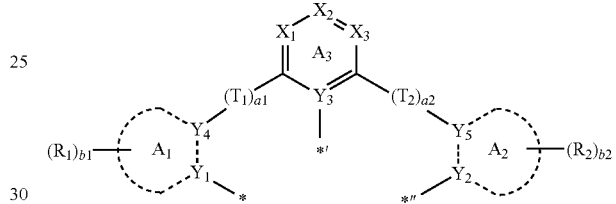

Formula 2 wherein, in Formulae 1 and 2,

M is palladium, gold, or platinum, $L_1$ is selected from tridentate ligands represented by Formula 2, $L_2$ is selected from monodentate organic ligands,

*, ', and *'' in Formula 2 each indicate a binding site to M in Formula 1, $Y_1$ to $Y_3$ are each nitrogen, $Y_4$ and $Y_5$ are each carbon, $Y_1$ is bound to $Y_4$ via a single or double bond, $Y_2$ is bound to $Y_5$ via a single or double bond, a bond between $Y_1$ and M and a bond between ligand $L_2$ and M are each a covalent bond, and a bond between $Y_3$ and M and a bond between $Y_2$ and M are each a coordinate bond, $T_1$ is a group selected from a single bond, *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom, $T_2$ is a group selected from *—O—*', *—S—*', *—C($R_6$)($R_7$)—*', *—C($R_6$)=*', *=C($R_6$)—*, *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom, $R_6$ and $R_7$ are optionally bound to each other to form a substituted or unsubstituted $C_5$-$C_{30}$ carbocyclic group or a substituted or unsubstituted $C_2$-$C_{30}$ heterocyclic group, a1 and a2 are each independently an integer selected from 1 to 3, a moiety in Formula 2 represented by
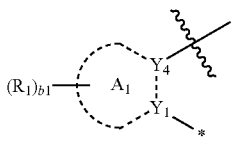
is represented by one of Formulae 3-32 to 3-34 and 3-48 to 3-50,
a moiety in Formula 2 represented by
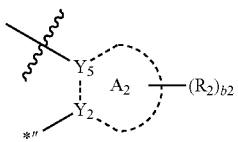
is represented by one of Formulae 4-1 to 4-53, and
a moiety in Formula 2 represented by
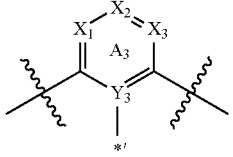
is represented by one of Formulae 5-1 to 5-48:
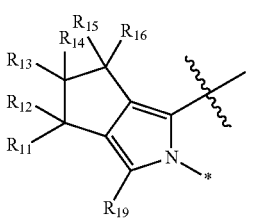
Formula 3-32
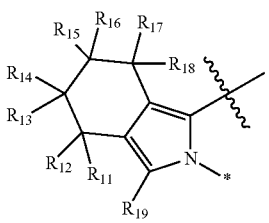
Formula 3-33
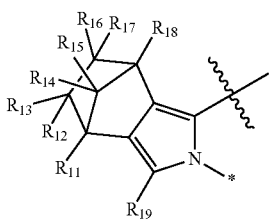
Formula 3-34
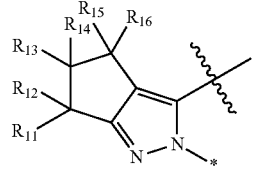
Formula 3-48
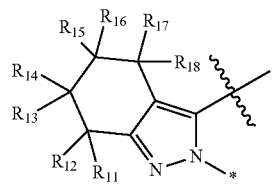
Formula 3-49
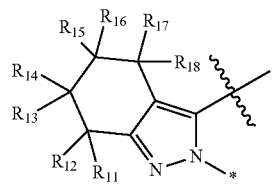
Formula 3-50
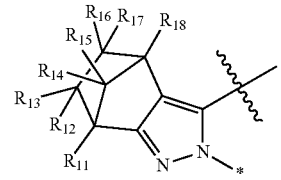
Formula 4-1
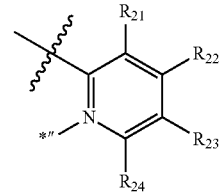
Formula 4-2
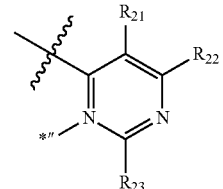
Formula 4-3
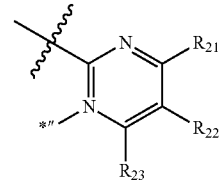
Formula 4-4
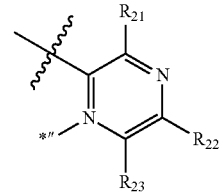
Formula 4-5
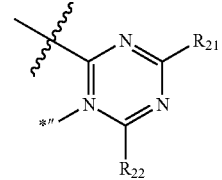

-continued
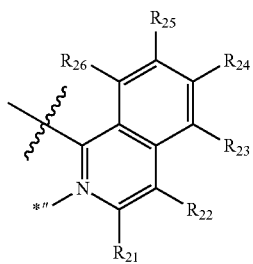
Formula 4-6
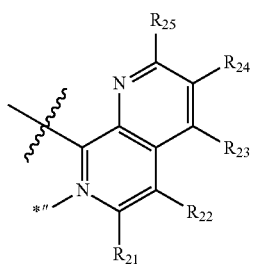
Formula 4-7
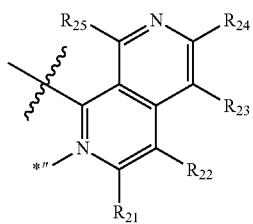
Formula 4-8
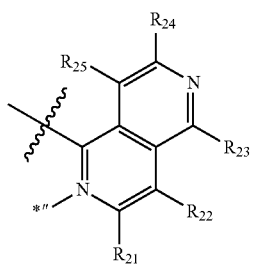
Formula 4-9
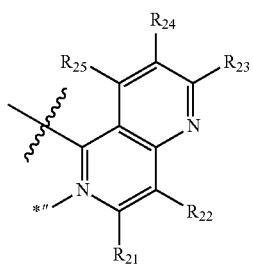
Formula 4-10
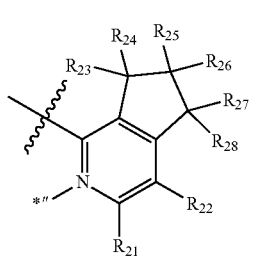
Formula 4-11
-continued
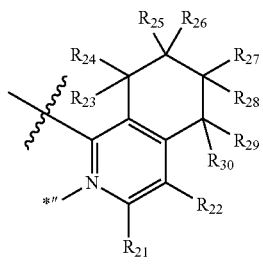
Formula 4-12
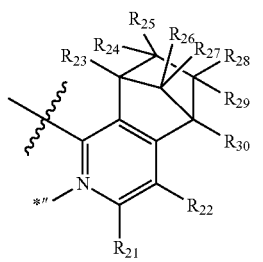
Formula 4-13
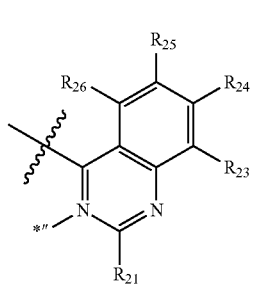
Formula 4-14
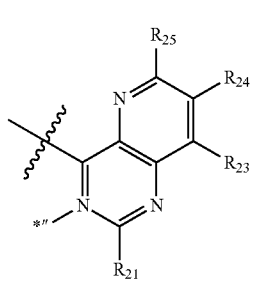
Formula 4-15
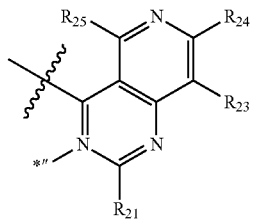
Formula 4-16
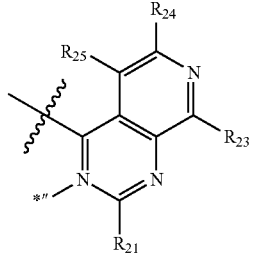
Formula 4-17

-continued
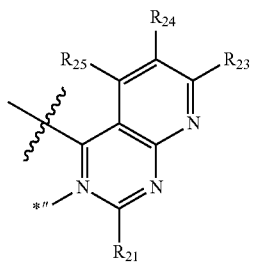
Formula 4-18
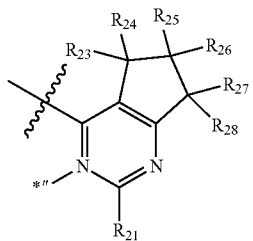
Formula 4-19
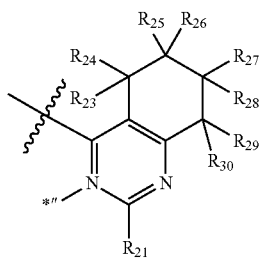
Formula 4-20
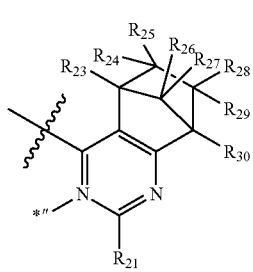
Formula 4-21
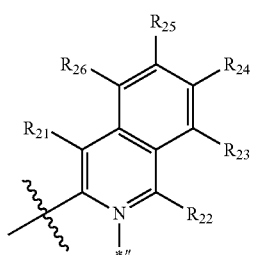
Formula 4-22
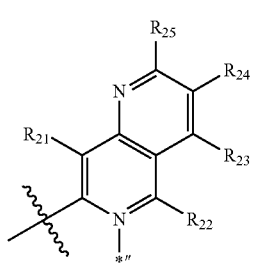
Formula 4-23
-continued
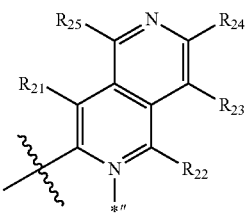
Formula 4-24
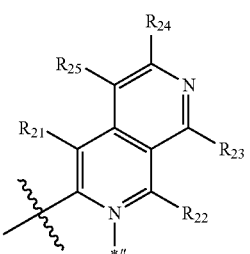
Formula 4-25
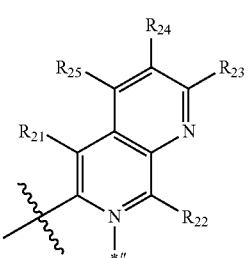
Formula 4-26
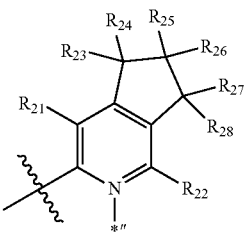
Formula 4-27
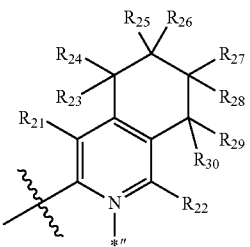
Formula 4-28
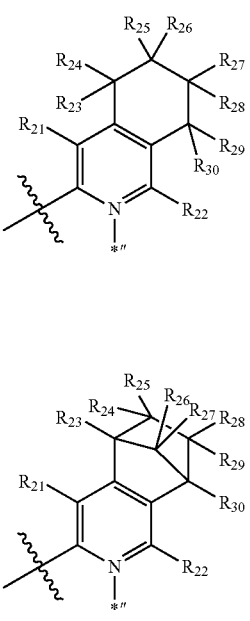
Formula 4-29

Formula 4-30 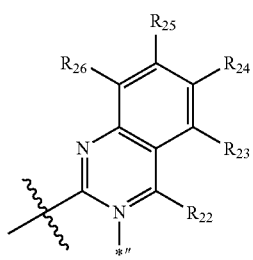
Formula 4-31 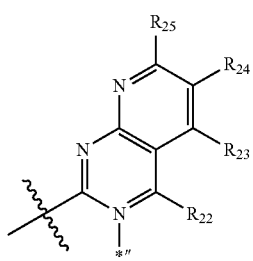
Formula 4-32 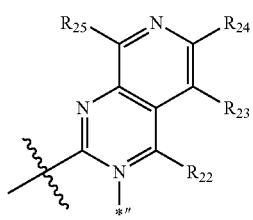
Formula 4-33 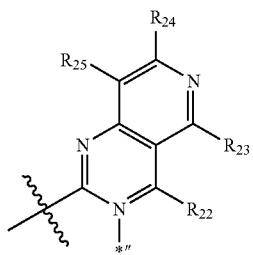
Formula 4-34 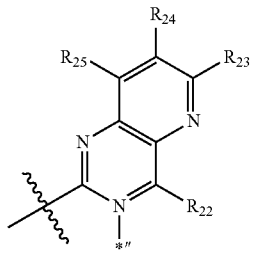
Formula 4-35 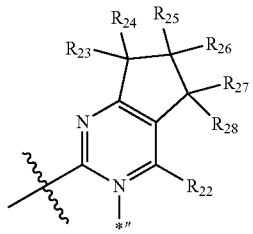
Formula 4-36 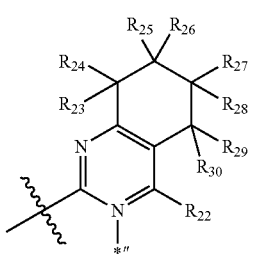
Formula 4-37 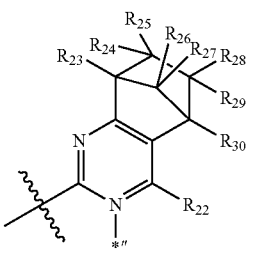
Formula 4-38 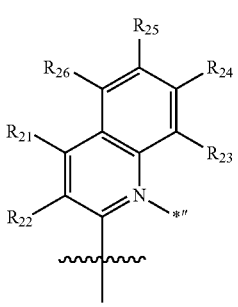
Formula 4-39 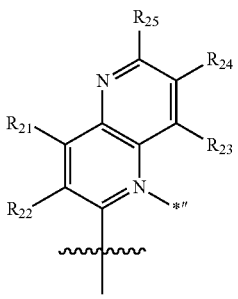
Formula 4-40 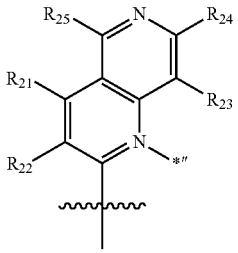

Formula 4-41
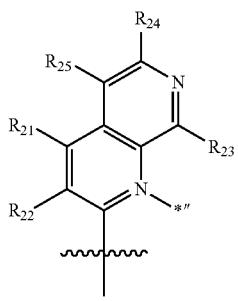
Formula 4-42
Formula 4-43
Formula 4-44
Formula 4-45
Formula 4-46
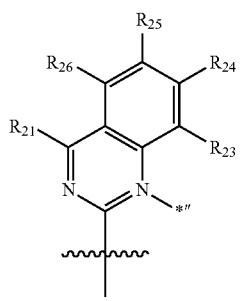
Formula 4-47
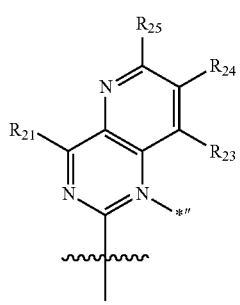
Formula 4-48
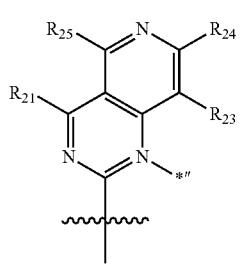
Formula 4-49
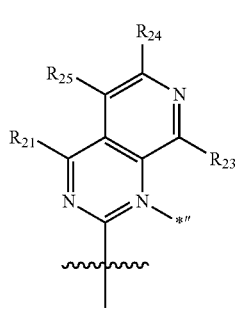
Formula 4-50
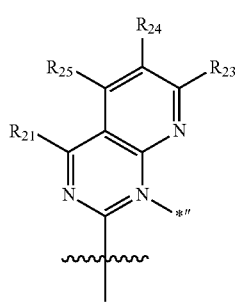

Formula 4-51
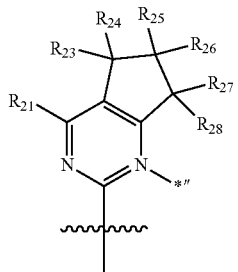
Formula 5-5
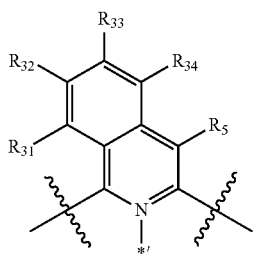
Formula 4-52
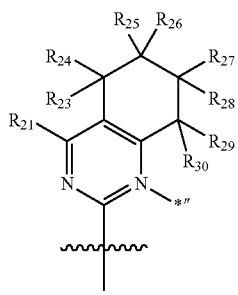
Formula 5-6
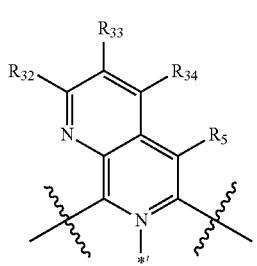
Formula 4-53
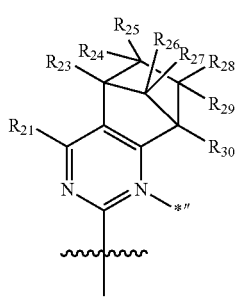
Formula 5-7
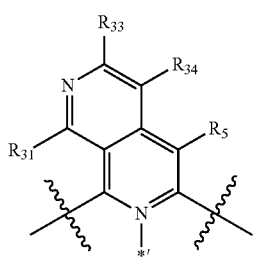
Formula 5-1
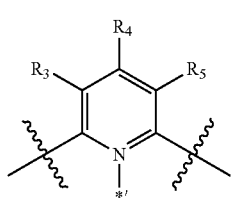
Formula 5-8
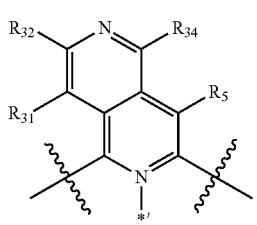
Formula 5-2
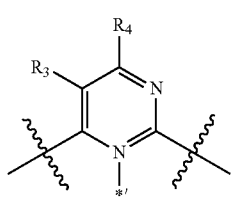
Formula 5-9
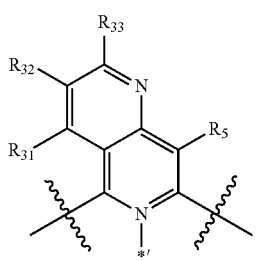
Formula 5-3
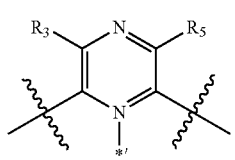
Formula 5-10
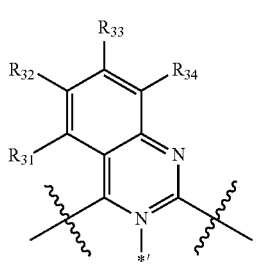
Formula 5-4
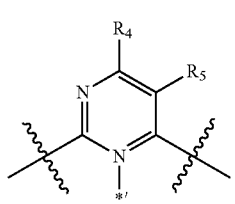

Formula 5-11
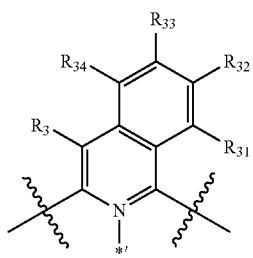
Formula 5-12
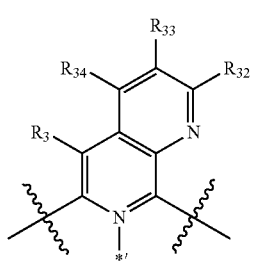
Formula 5-13
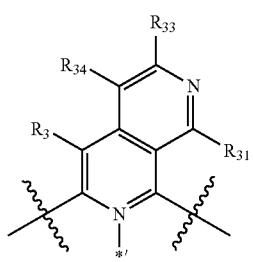
Formula 5-14
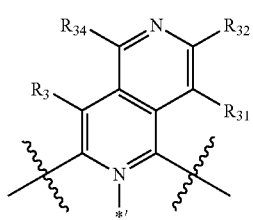
Formula 5-15
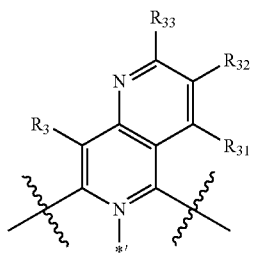
Formula 5-16
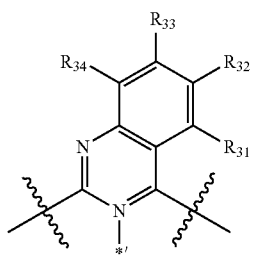
Formula 5-17
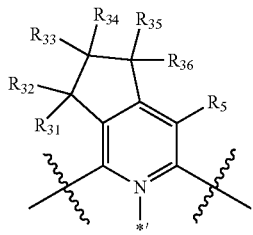
Formula 5-18
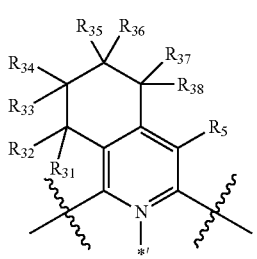
Formula 5-19
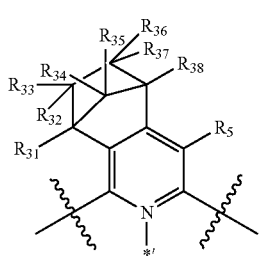
Formula 5-20
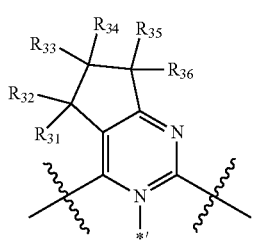
Formula 5-21
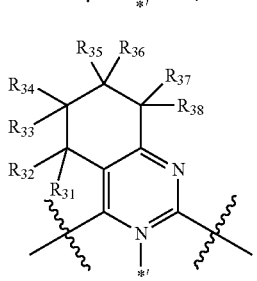
Formula 5-22
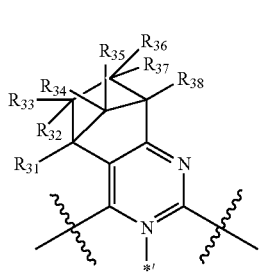

Formula 5-23
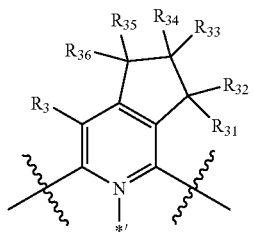
Formula 5-24
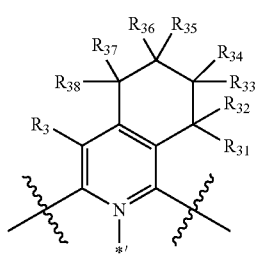
Formula 5-25
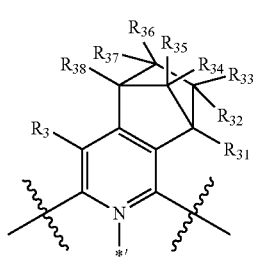
Formula 5-26
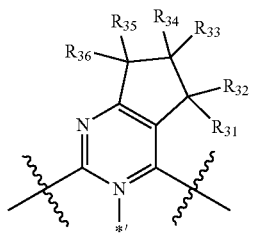
Formula 5-27
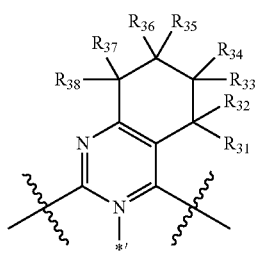
Formula 5-28
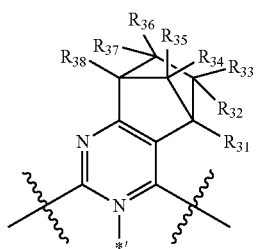
Formula 5-29
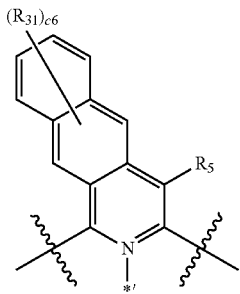
Formula 5-30
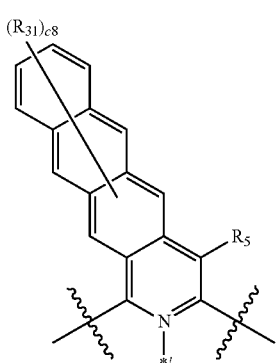
Formula 5-31
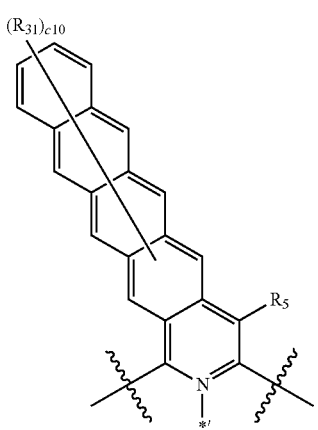
Formula 5-32
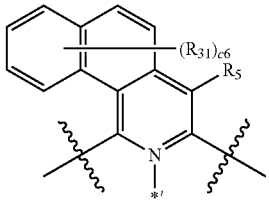
Formula 5-33
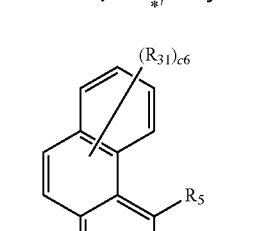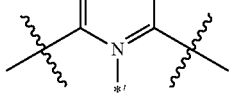

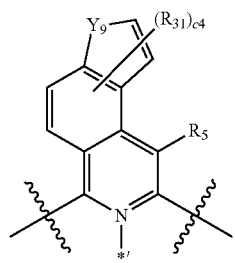
Formula 5-34
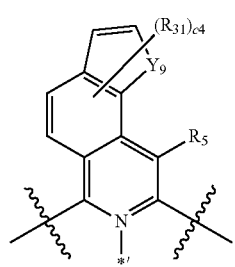
Formula 5-35
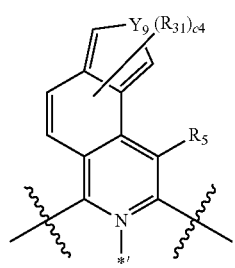
Formula 5-36
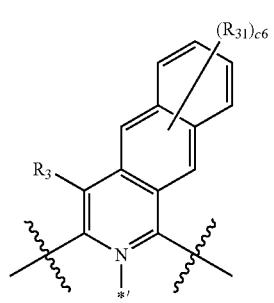
Formula 5-37
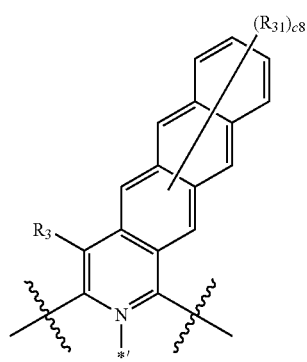
Formula 5-38
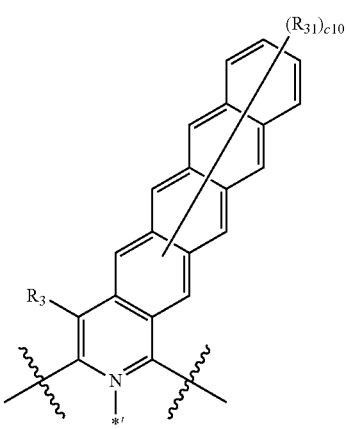
Formula 5-39
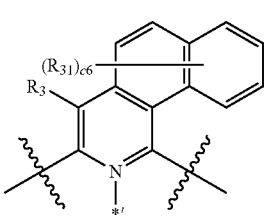
Formula 5-40
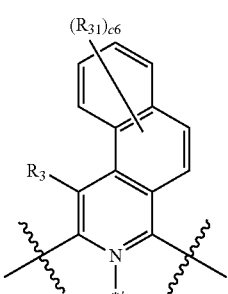
Formula 5-41
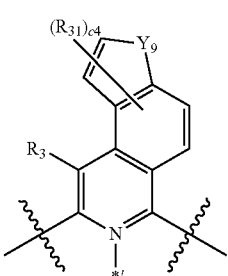
Formula 5-42
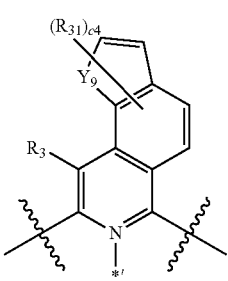
Formula 5-43

-continued

Formula 5-44

Formula 5-45

Formula 5-46

Formula 5-47

Formula 5-48 wherein, in the above Formulae, $Y_7$ and $Y_8$ are each independently O or S, $Y_9$ is O, S, or $N(R_{39})$, $R_3$ to $R_7$ and $R_{11}$ to $R_{39}$ are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), c3 is an integer selected from 0 to 3, c4 is an integer selected from 0 to 4, c6 is an integer selected from 0 to 6, c7 is an integer selected from 0 to 7, c8 is an integer selected from 0 to 8, c10 is an integer selected from 0 to 10, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), wherein Q$_1$ to Q$_9$, Q$_{11}$ to Q$_{19}$, Q$_{21}$ to Q$_{29}$, and Q$_{31}$ to Q$_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryl group substituted with at least one selected from a C$_1$-C$_{60}$ alkyl group and a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group.

2. The organometallic compound of claim 1, wherein R$_3$ to R$_7$ and R$_{11}$ to R$_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

3. The organometallic compound of claim 1, wherein $R_3$ to $R_7$ and $R_{11}$ to $R_{39}$ are each independently selected from hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

4. The organometallic compound of claim 1, wherein $R_3$ to $R_7$ and $R_{11}$ to $R_{39}$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-38, and —$Si(Q_3)(Q_4)(Q_5)$:

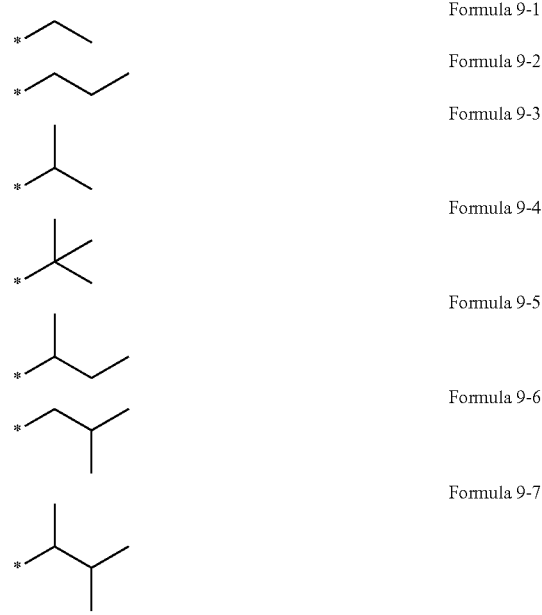

-continued
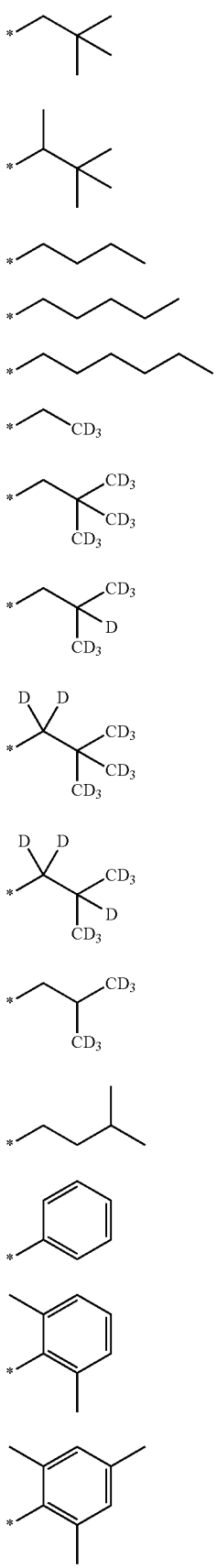
-continued
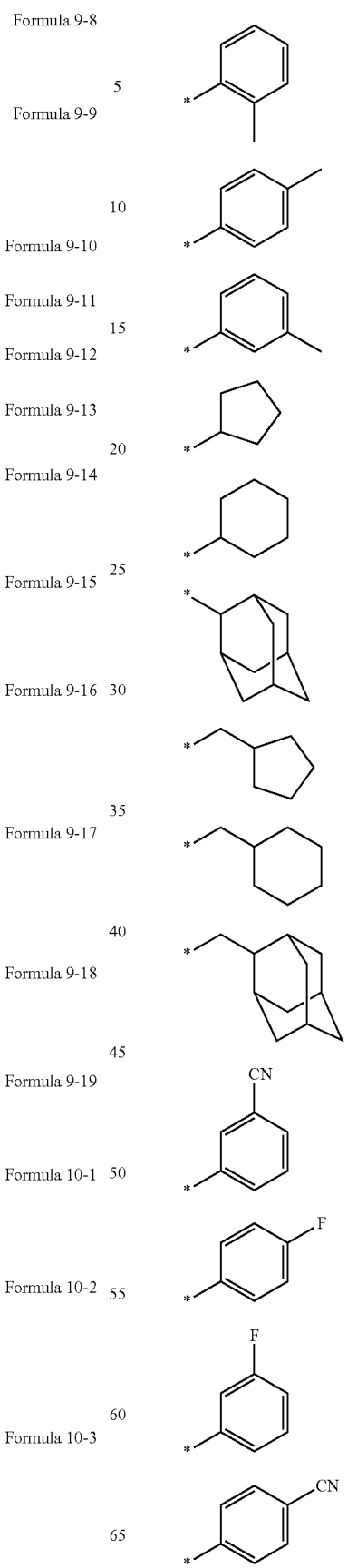
Formula 9-8
Formula 9-9
Formula 9-10
Formula 9-11
Formula 9-12
Formula 9-13
Formula 9-14
Formula 9-15
Formula 9-16
Formula 9-17
Formula 9-18
Formula 9-19
Formula 10-1
Formula 10-2
Formula 10-3
Formula 10-4
Formula 10-5
Formula 10-6
Formula 10-7
Formula 10-8
Formula 10-9
Formula 10-10
Formula 10-11
Formula 10-12
Formula 10-13
Formula 10-14
Formula 10-15
Formula 10-16

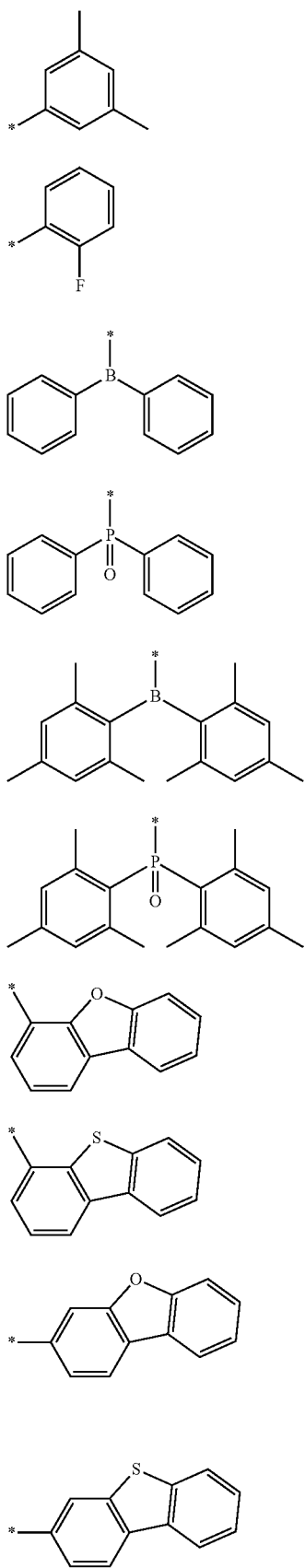
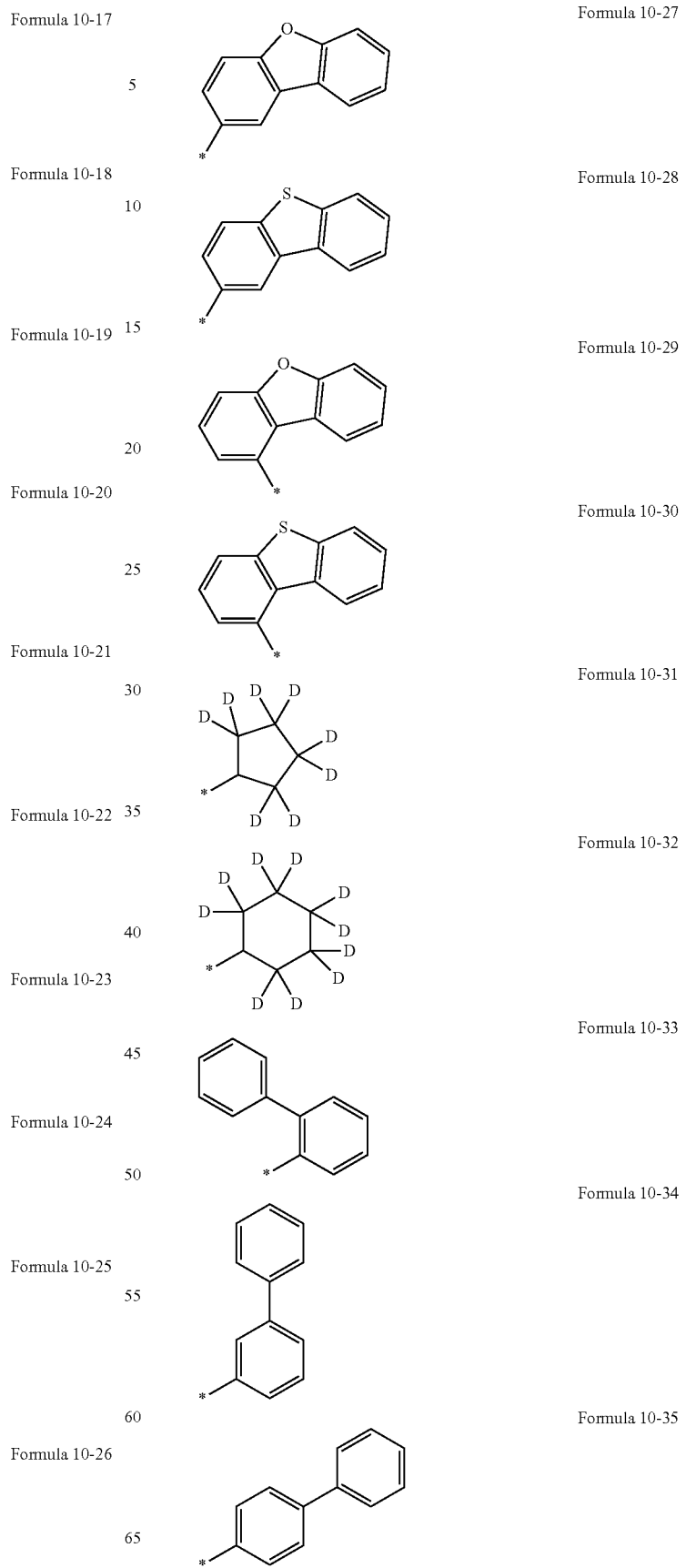

-continued

Formula 10-36

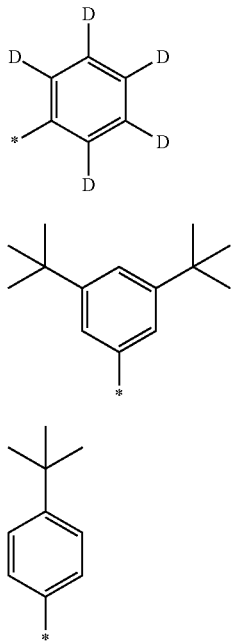

Formula 10-37

Formula 10-38

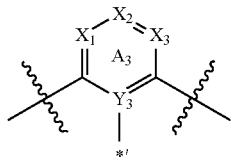

wherein, in Formulae 9-1 to 9-19 and 10-1 to 10-38, * indicates a binding site to an adjacent atom.

5. The organometallic compound of claim 1, wherein the moiety represented by

in Formula 2 is represented by one of Formulae 5-1 to 5-28, 5-29, and 5-45.

6. The organometallic compound of claim 1, wherein
$T_1$ is a single bond,
$T_2$ is a group selected from *—O—*', *—S—*', *—C($R_6$)($R_7$)—*', *—N($R_6$)—*', and *—Si($R_6$)($R_7$)—*', wherein * and *' in each of the foregoing groups independently indicate a binding site to a neighboring atom, and
$R_6$ and $R_7$ are optionally bound to each other via a first linking group,
wherein the first linking group is selected from
a single bond, a $C_1$-$C_3$ alkylene group, and a $C_2$-$C_3$ alkenylene group;
a $C_1$-$C_3$ alkylene group and a $C_2$-$C_3$ alkenylene group, each substituted with at least one selected from deuterium, a cyano group, $C_1$-$C_{10}$ alkyl group, $C_1$-$C_{10}$ alkoxy group, a phenyl group, and a biphenyl group, and
a2 is 1.

7. An organometallic compound represented by Formula 1:

$$M(L_1)(L_2), \quad \text{Formula 1}$$

wherein $L_1$ in Formula 1 is selected from ligands represented by one of Formulae 2B to 2C:

Formula 2B

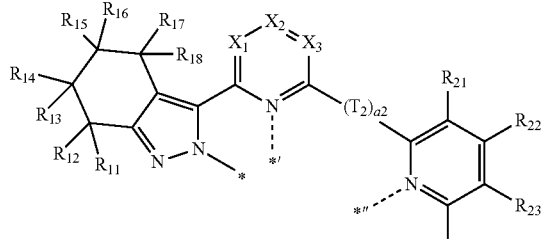

Formula 2C

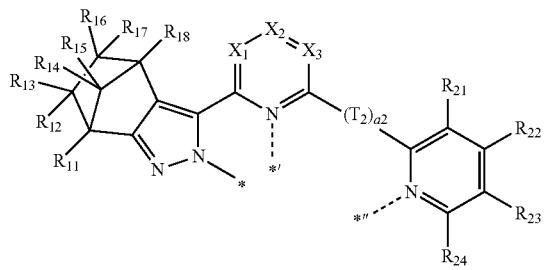

M in Formula 1 is palladium, gold, or platinum,
$L_2$ in Formula 1 is selected from monodentate organic ligands,
wherein, in Formulae 2B to 2C,
$T_2$ is a group selected from *—O—*', *—S—*', *—C($R_6$)($R_7$)—*', *—C($R_6$)=*', *=C($R_6$)—*, *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom,
$R_6$ and $R_7$ are optionally bound to each other to form a substituted or unsubstituted $C_5$-$C_{30}$ carbocyclic group or a substituted or unsubstituted $C_2$-$C_{30}$ heterocyclic group,
a2 is an integer selected from 1 to 3,
$X_1$ is N or C($R_3$), $X_2$ is N or C($R_4$), $X_3$ is N or C($R_5$), at least two selected from $R_3$ to $R_5$ are optionally bound to each other to form a substituted or unsubstituted $C_5$-$C_{30}$ carbocyclic group or a substituted or unsubstituted $C_2$-$C_{30}$ heterocyclic group,
*, *', and *'' in Formulae 2A to 2C each indicate a binding site to M in Formula 1,
$R_3$ to $R_7$, $R_{11}$ to $R_{18}$, and $R_{21}$ to $R_{24}$ are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), at least two of $R_{21}$ to $R_{24}$ are optionally bound to each other to form a substituted or unsubstituted $C_5$-$C_{30}$ carbocyclic group or a substituted or unsubstituted $C_2$-$C_{30}$ heterocyclic group, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

8. The organometallic compound of claim 1, wherein $L_2$ in Formula 1 is selected from ligands represented by Formula 6-1:

$$*\!-\!(T_3)_{a3}\!-\!R_{61} \qquad \text{Formula 6-1}$$

wherein, in Formula 6-1, $T_3$ is a group selected from a single bond, *—O—*', *—S—*', *—C($R_{62}$)($R_{63}$)—*', *—C($R_{62}$)=*', *=C($R_{62}$)—*', *—C($R_{62}$)=C($R_{63}$)—*', *—C(=O)—*', *—C(=S)—*', *—C≡C—*', and *—N($R_{62}$)—*', wherein * and *' in each of the foregoing groups independently indicate a binding site to a neighboring atom, a3 is an integer selected from 1 to 5, $R_{61}$ is selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), —P(=O)(Q$_8$)(Q$_9$), and P(Q$_{41}$)(Q$_{42}$)(Q$_{43}$), wherein Q$_1$ to Q$_9$ and Q$_{41}$ to Q$_{43}$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, R$_{62}$ to R$_{63}$ are each independently selected from hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, R$_{62}$ and R$_{63}$ are optionally bound to each other to form a substituted or unsubstituted C$_5$-C$_{30}$ carbocyclic group or a substituted or unsubstituted C$_2$-C$_{30}$ heterocyclic group, and

* in Formula 1 indicates a binding site to M.

9. The organometallic compound of claim 1, wherein L$_2$ in Formula 1 is selected from ligands represented by one of Formulae 13-1 to 13-49 and 14-1 to 14-28:

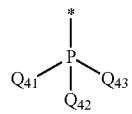

Formula 13-1

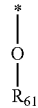

Formula 13-2

Formula 13-3

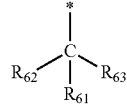

Formula 13-4

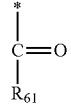

Formula 13-5

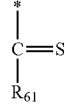

Formula 13-6

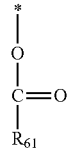

Formula 13-7

Formula 13-8

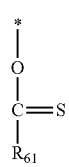

Formula 13-9

-continued
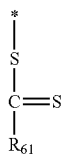
Formula 13-10
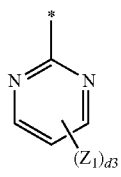
Formula 13-19
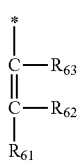
Formula 13-11
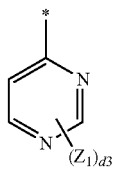
Formula 13-20
Formula 13-12
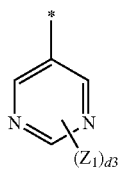
Formula 13-21
Formula 13-13
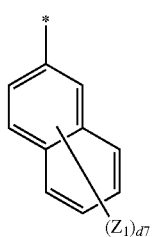
Formula 13-22
Formula 13-14
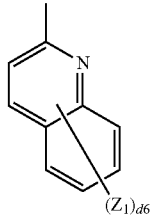
Formula 13-23
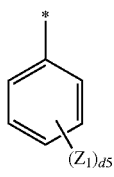
Formula 13-15
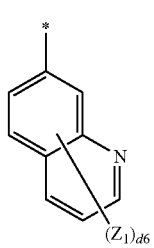
Formula 13-24
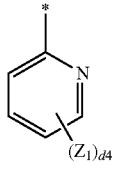
Formula 13-16
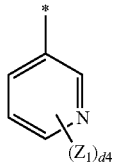
Formula 13-17
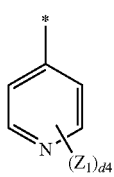
Formula 13-18
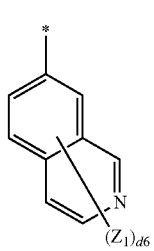
Formula 13-25

Formula 13-26
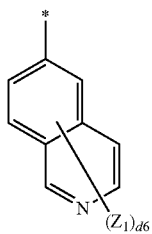
Formula 13-32
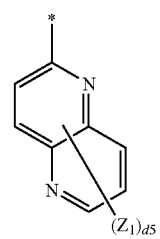
Formula 13-27
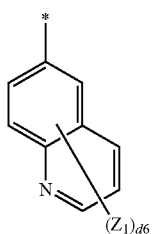
Formula 13-33
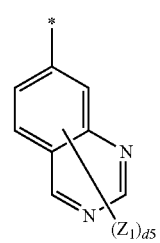
Formula 13-28
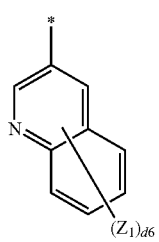
Formula 13-34
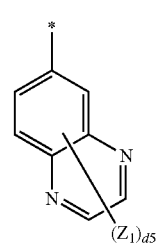
Formula 13-29
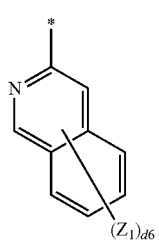
Formula 13-35
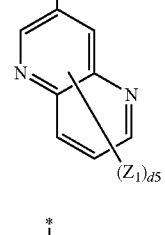
Formula 13-30
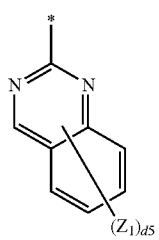
Formula 13-36
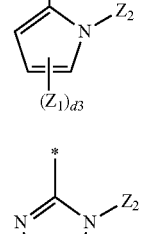
Formula 13-31
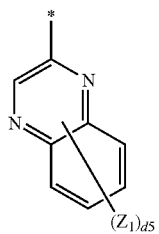
Formula 13-37
Formula 13-38
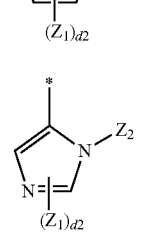

-continued
Formula 13-39
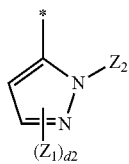
Formula 13-48
Formula 13-40
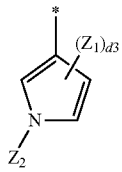
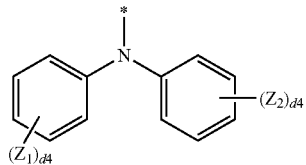
Formula 13-49
Formula 13-41
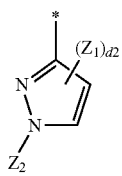
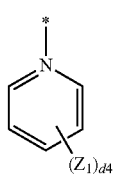
Formula 14-1
Formula 13-42
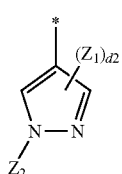
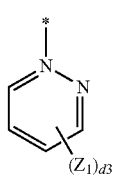
Formula 14-2
Formula 13-43
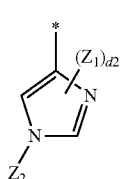
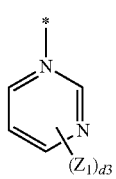
Formula 14-3
Formula 13-44
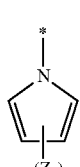
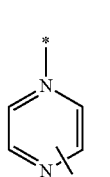
Formula 14-4
Formula 13-45
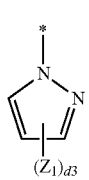
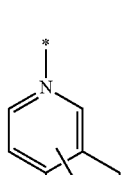
Formula 14-5
Formula 13-46
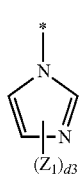
Formula 14-6
Formula 13-47
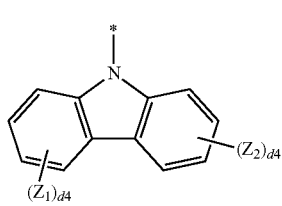
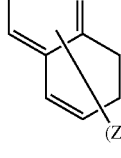

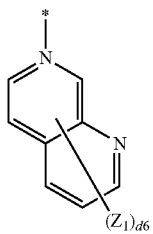
Formula 14-7
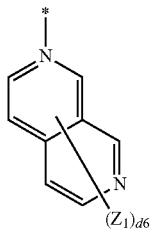
Formula 14-8
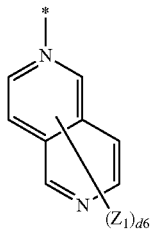
Formula 14-9
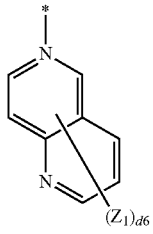
Formula 14-10
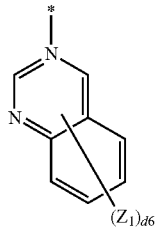
Formula 14-11
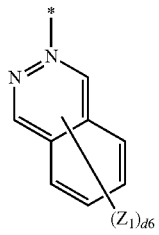
Formula 14-12
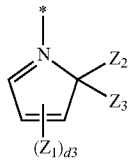
Formula 14-13
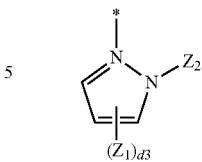
Formula 14-14
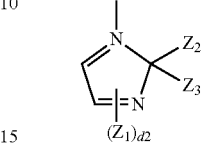
Formula 14-15
Formula 14-16
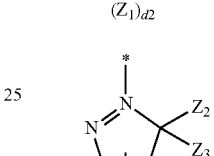
Formula 14-17
Formula 14-18
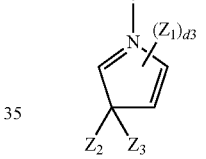
Formula 14-19
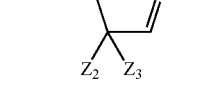
Formula 14-20
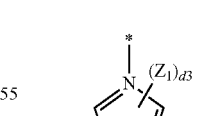
Formula 14-21
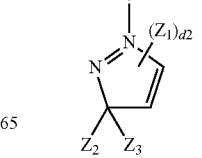
Formula 14-22

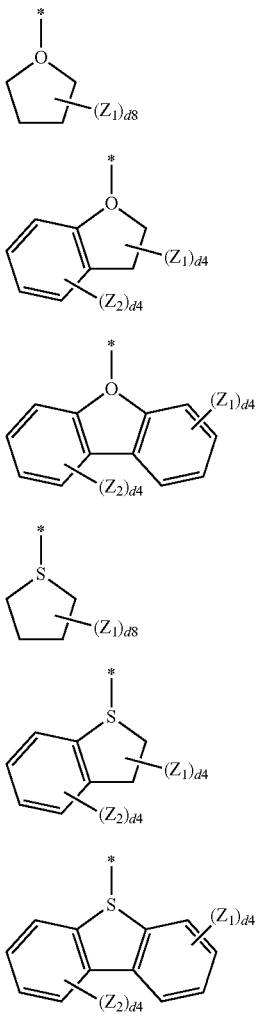

Formula 14-23
Formula 14-24
Formula 14-25
Formula 14-26
Formula 14-27
Formula 14-28 wherein, in Formulae 13-1 to 13-49 and 14-1 to 14-28, $R_{61}$ is selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$N(Q_1)(Q_2)$, —$Si(Q_3)(Q_4)(Q_5)$, —$B(Q_6)(Q_7)$, —$P(=O)(Q_8)(Q_9)$, and $P(Q_{41})(Q_{42})(Q_{43})$, $Z_1$ to $Z_3$ are each independently selected from hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, wherein $Q_1$ to $Q_9$, $Q_{31}$ to $Q_{39}$ and $Q_{41}$ to $Q_{43}$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, d2 is an integer selected from 1 and 2, d3 is an integer selected from 1 to 3, d4 is an integer selected from 1 to 4, d5 is an integer selected from 1 to 5, d6 is an integer selected from 1 to 6, d7 is an integer selected from 1 to 7, d8 is an integer selected from 1 to 8, and

* in Formula 1 indicates a binding site to M.

10. An organometallic compound being one of Compounds 1 to 180:

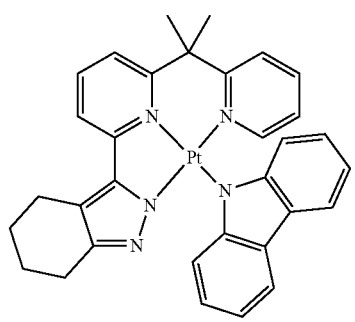

1

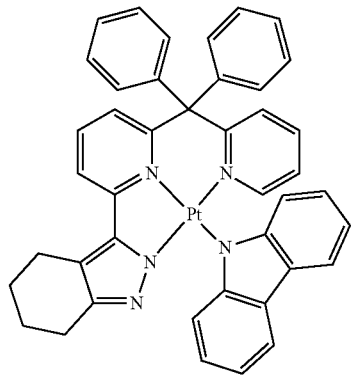

2

201
-continued
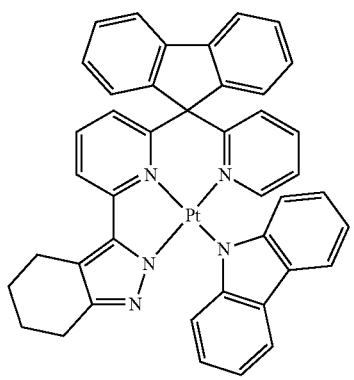
3
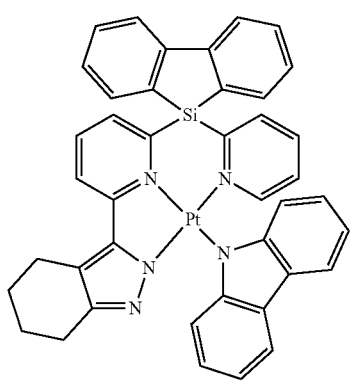
4
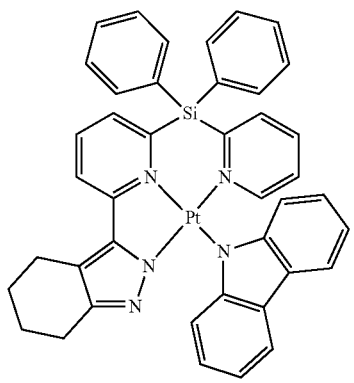
5
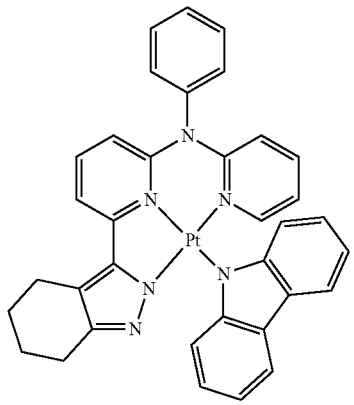
6
202
-continued
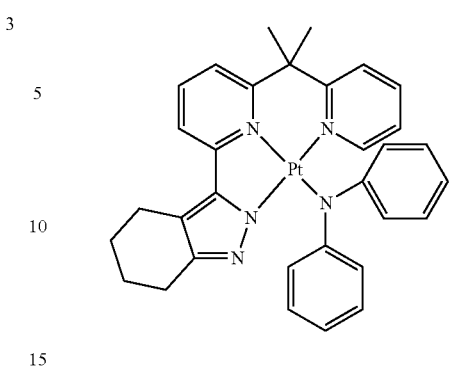
7
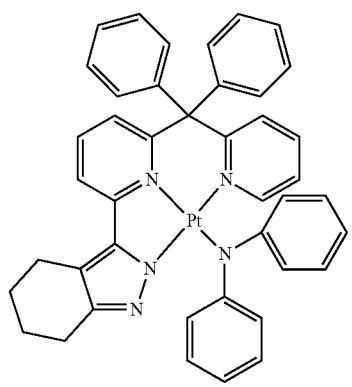
8
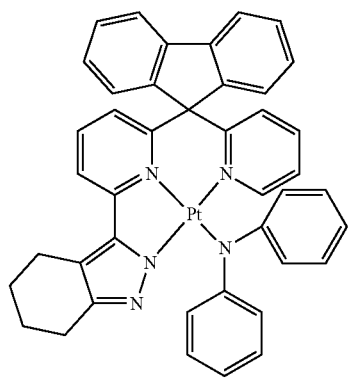
9
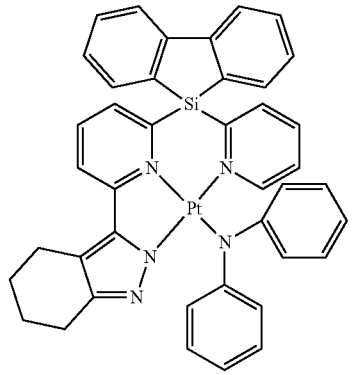
10

11
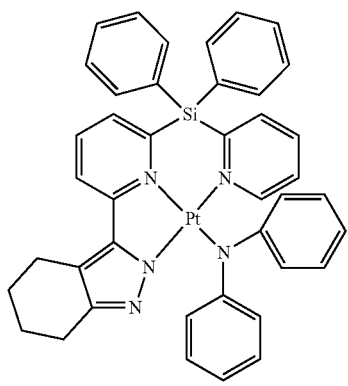
12
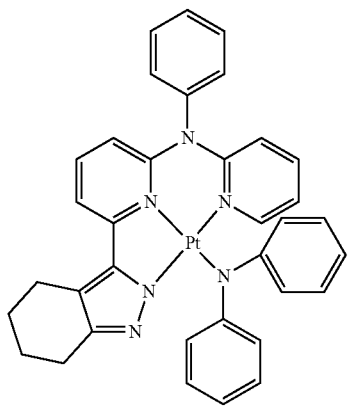
13
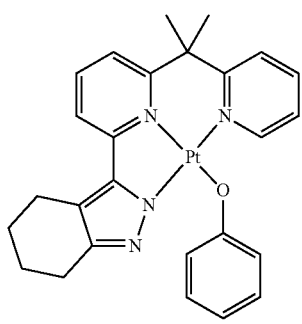
14
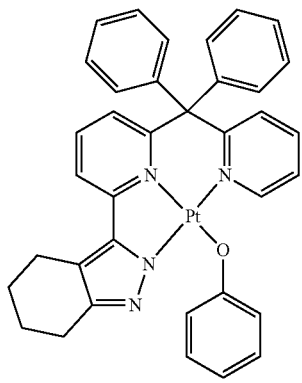
15
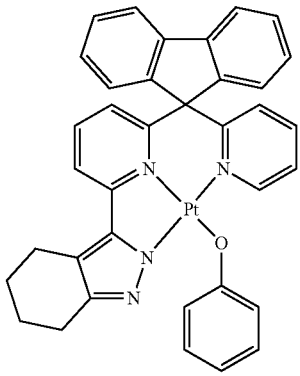
16
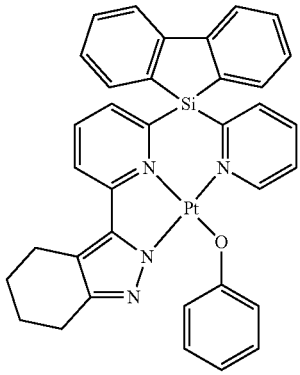
17
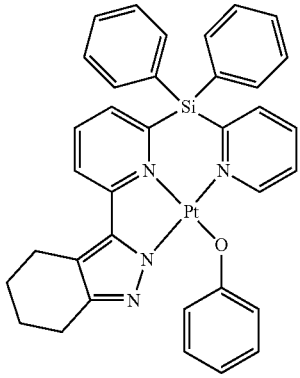
18
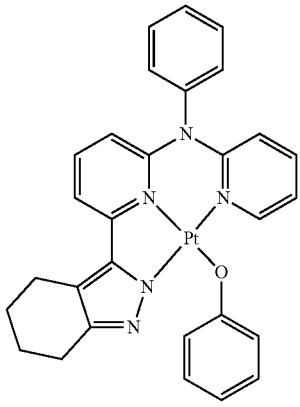

205
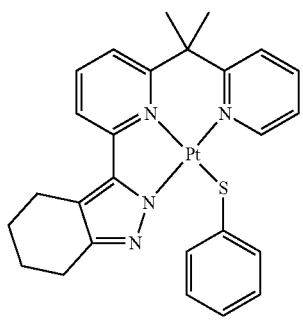
19
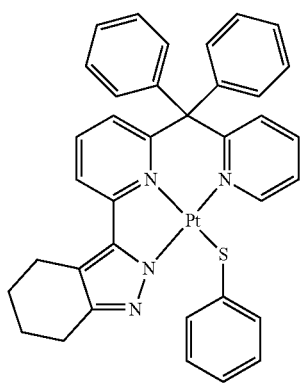
20
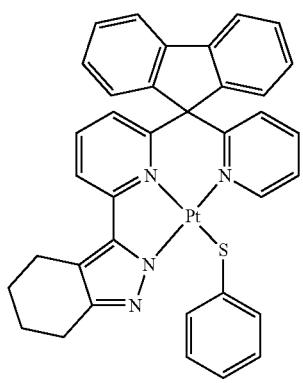
21
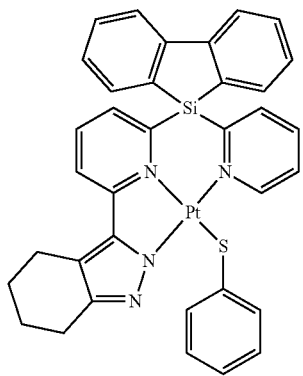
22
206
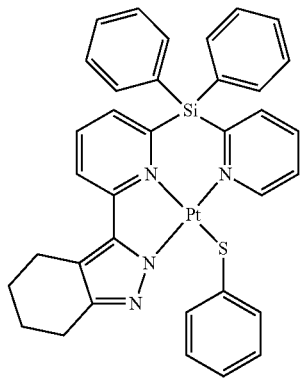
23
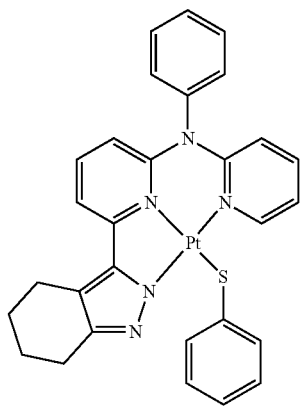
24
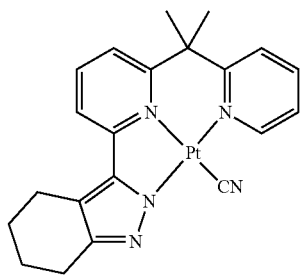
25
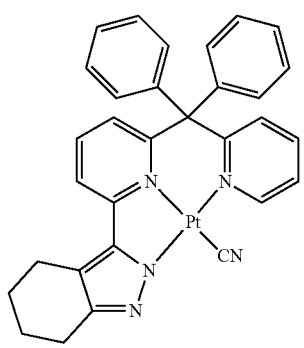
26

27
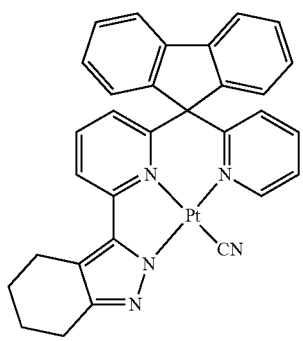
28
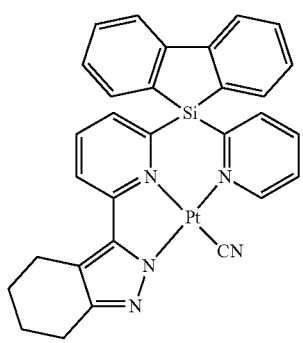
29
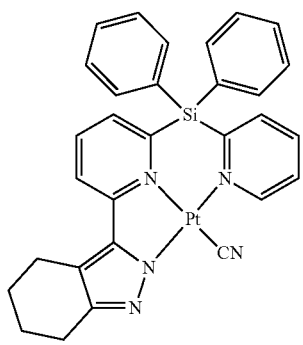
30
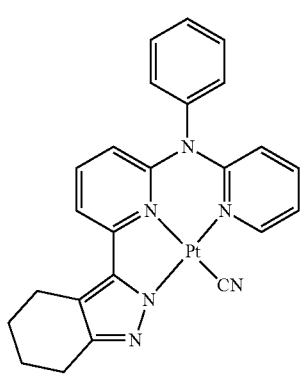
31
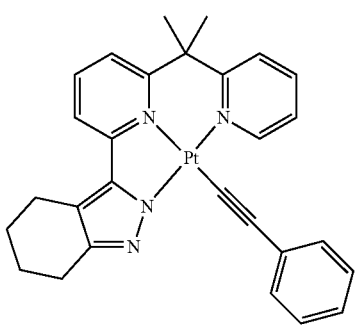
32
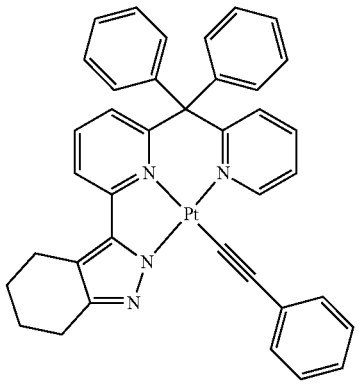
33
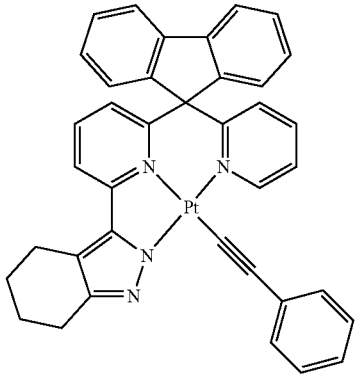
34
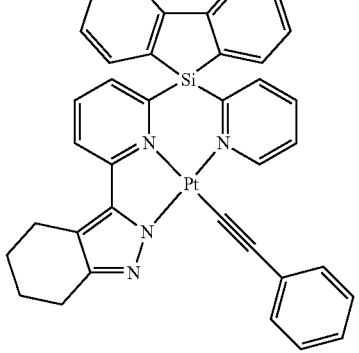

209
-continued
35
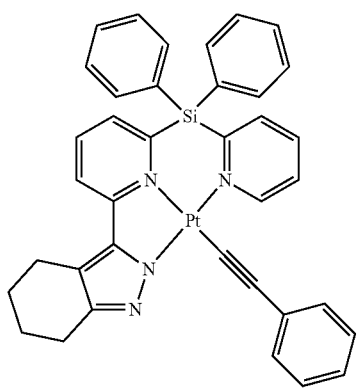
36
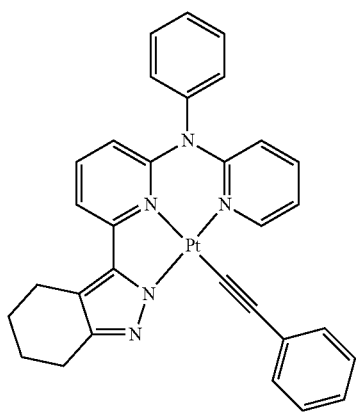
37
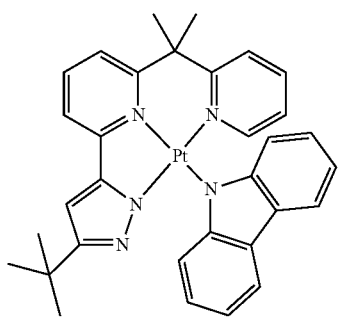
38
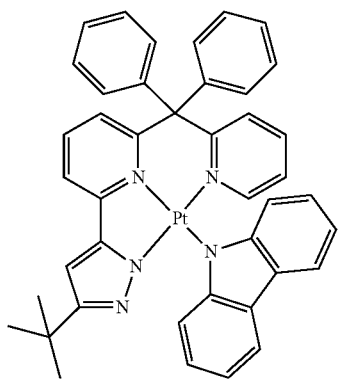
210
-continued
39
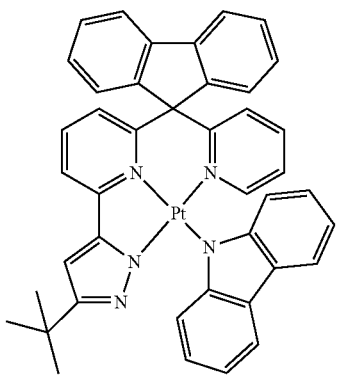
40
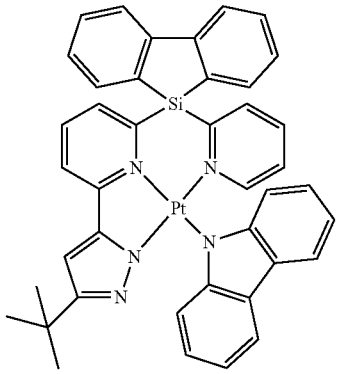
41
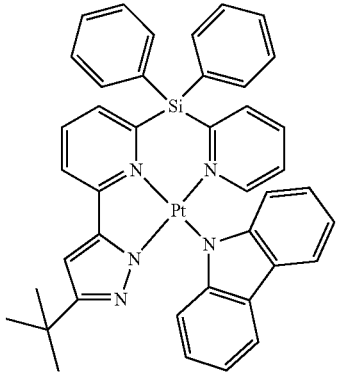
42
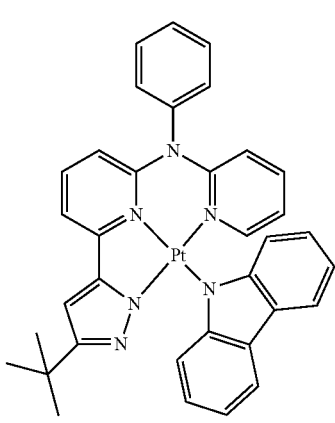

211
-continued
43
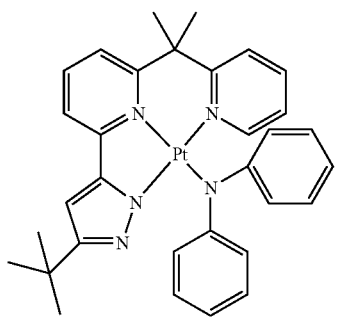
44
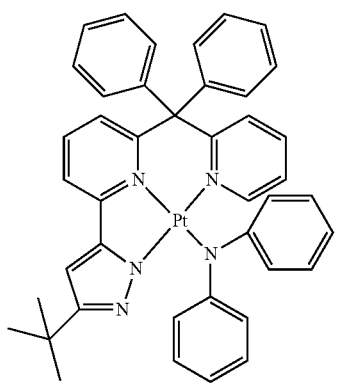
45
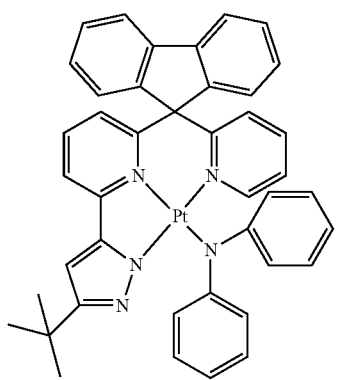
46
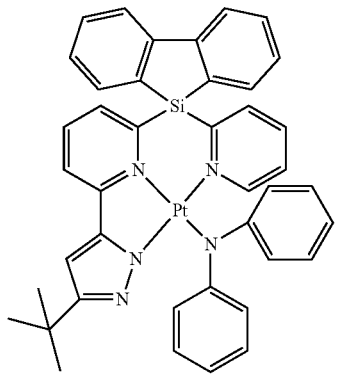
212
-continued
47
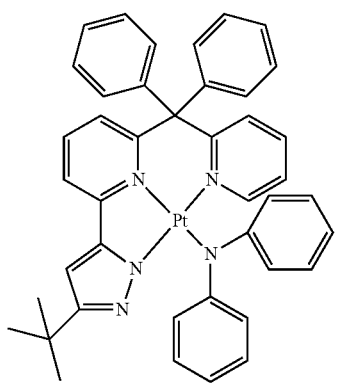
48
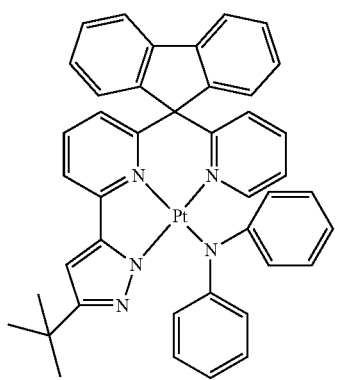
49
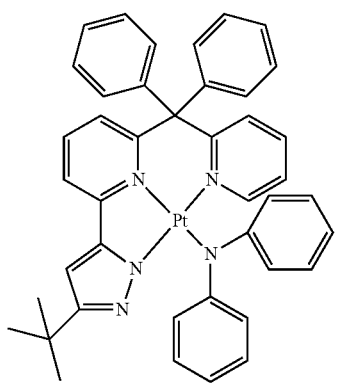
50
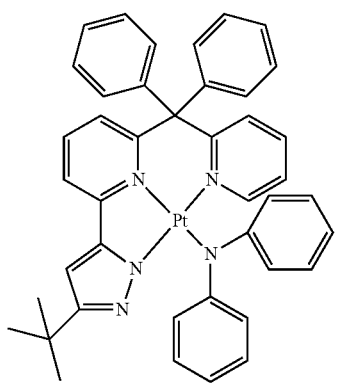

-continued
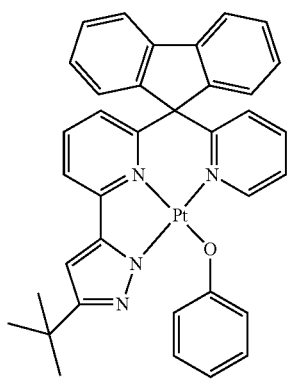
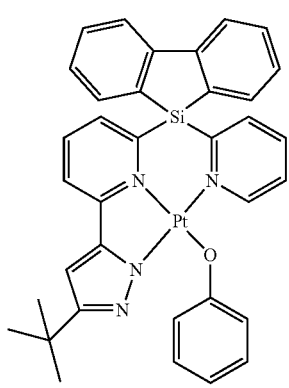
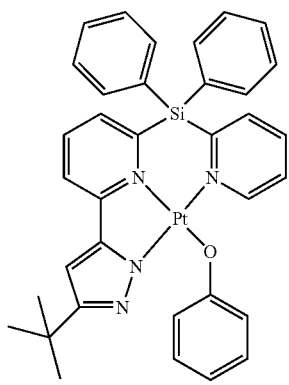
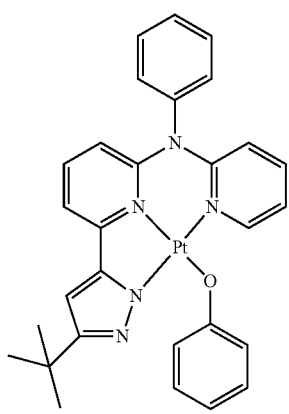
-continued
51
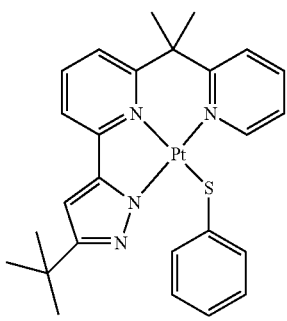
52
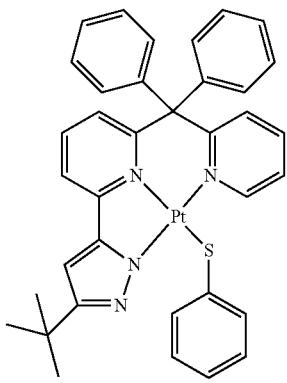
53
57
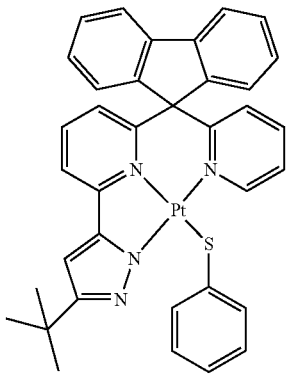
54
58
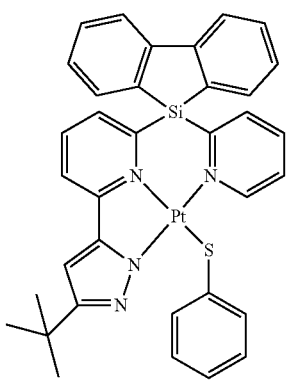

215
-continued
59
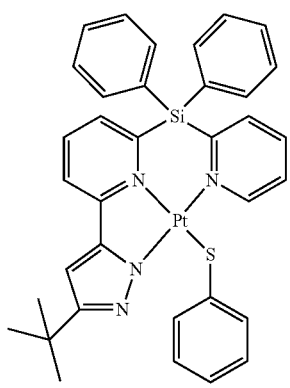
60
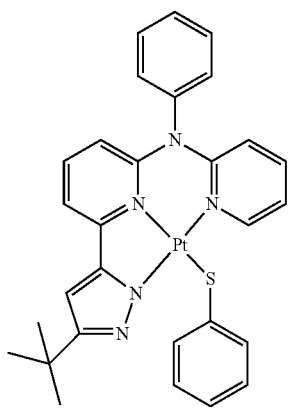
61
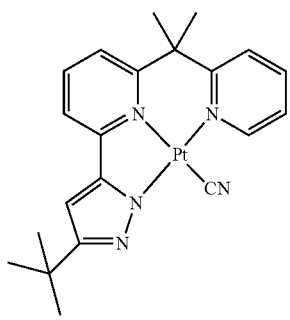
62
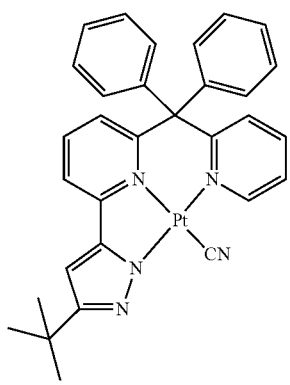
216
-continued
63
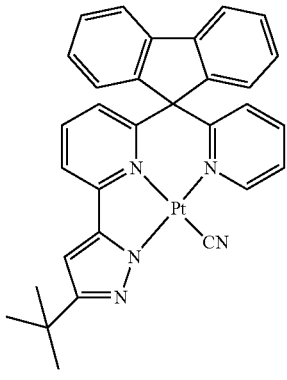
64
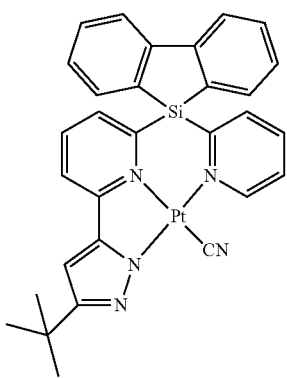
65
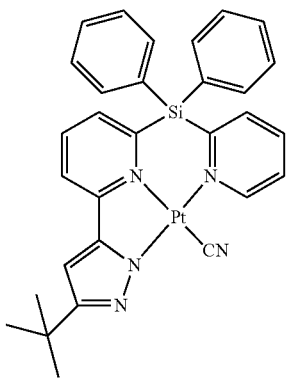
66
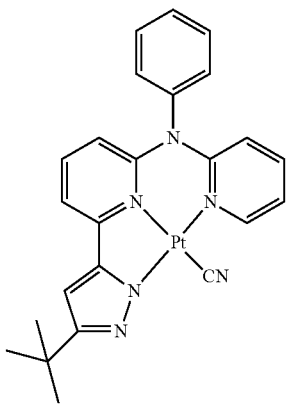

217
-continued
67
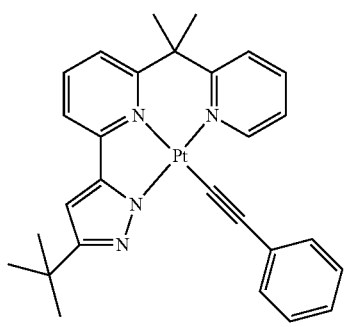
68
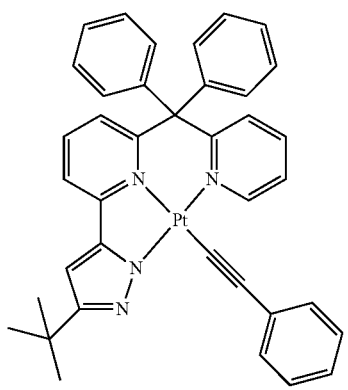
69
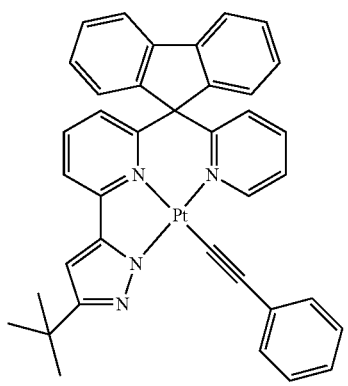
70
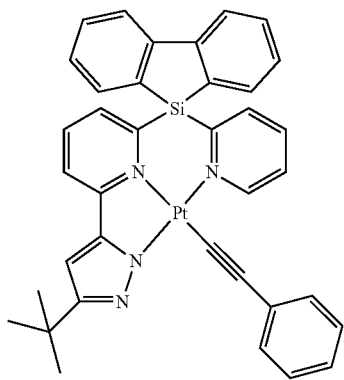
218
-continued
71
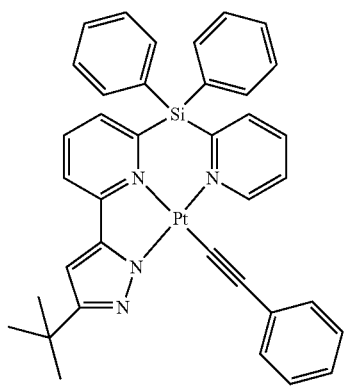
72
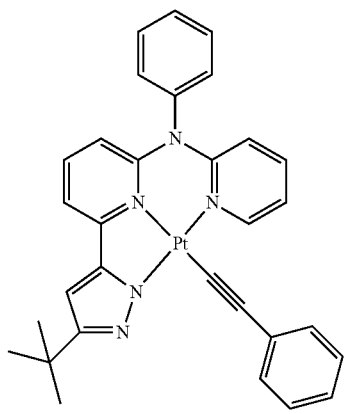
73
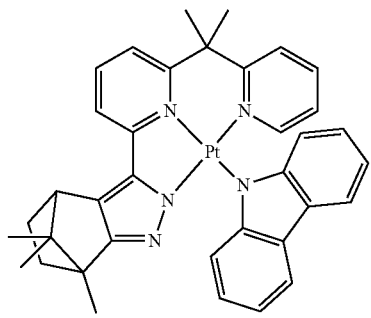
74
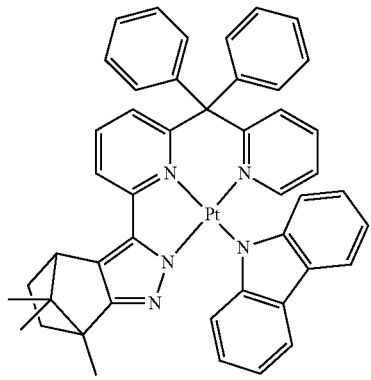

75
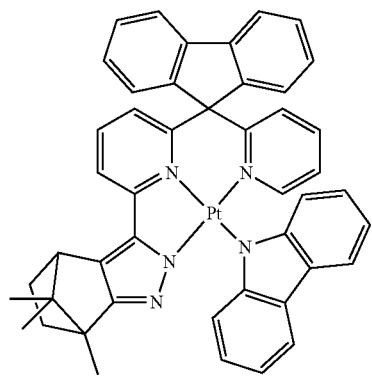
76
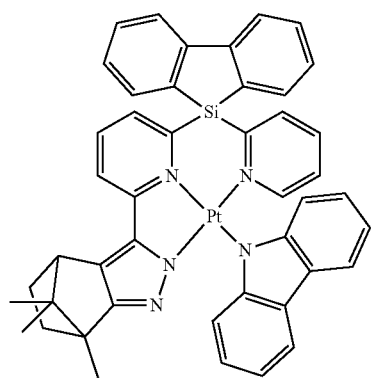
77
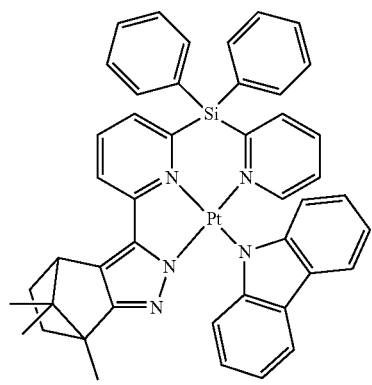
78
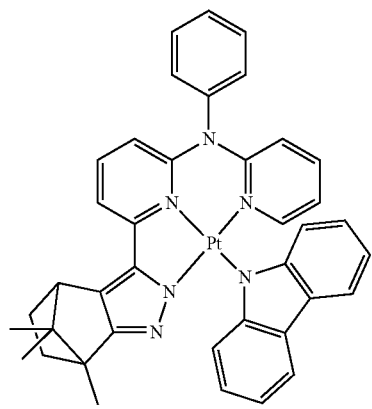
79
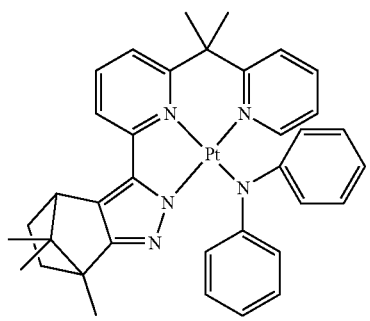
80
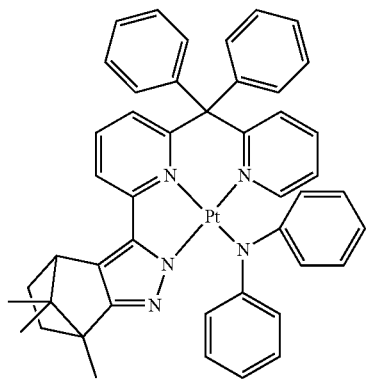
81
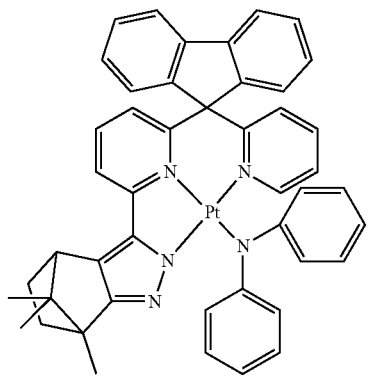
82
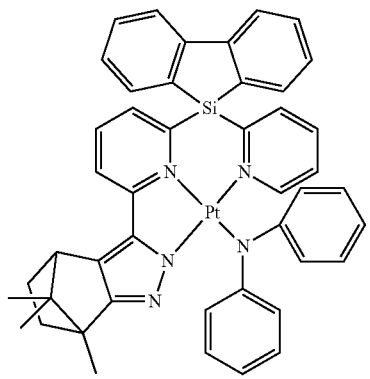

221
-continued
83
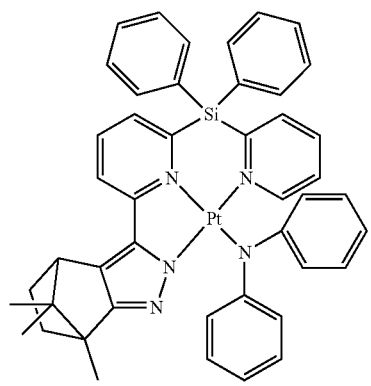
84
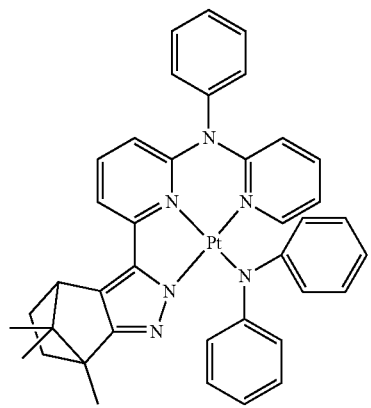
85
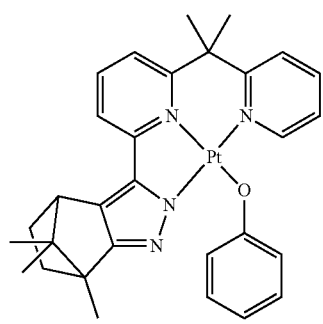
86
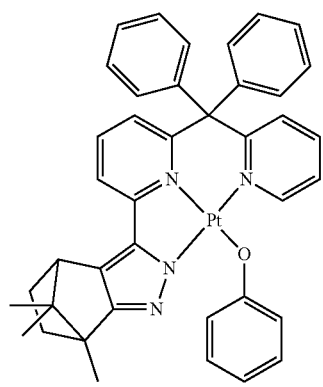
222
-continued
87
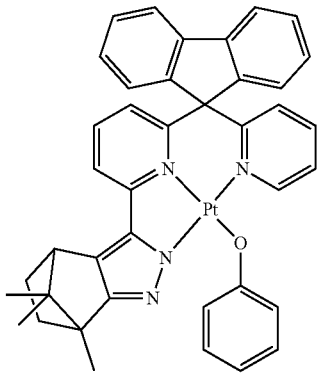
88
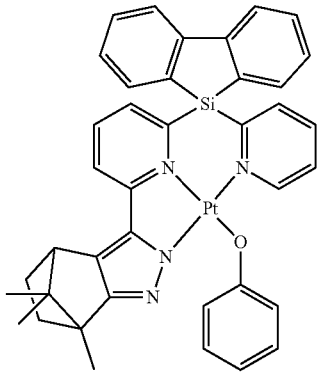
89
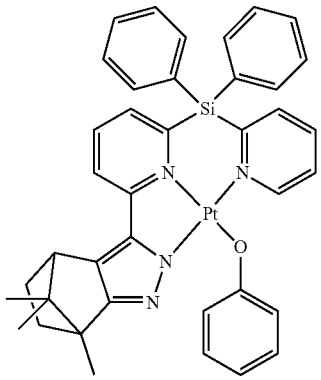
90
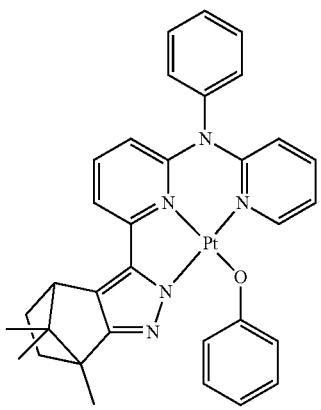

223
-continued
91
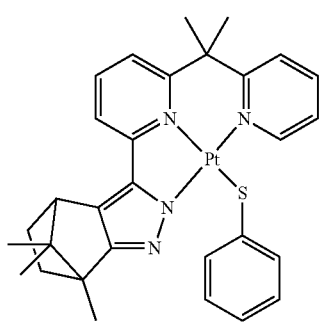
92
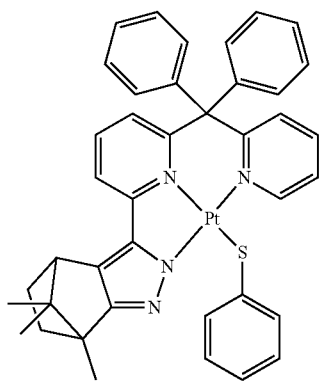
93
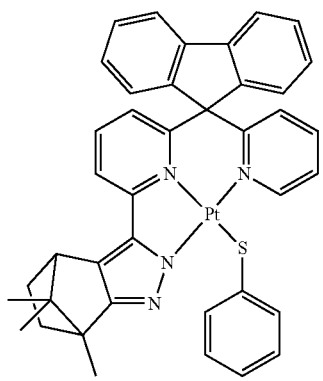
94
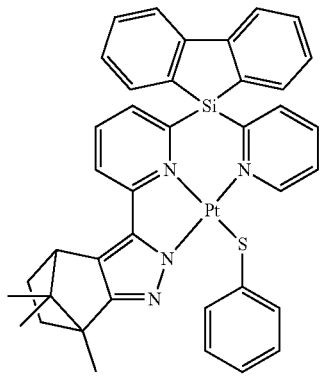
224
-continued
95
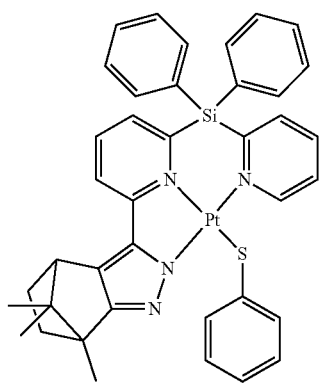
96
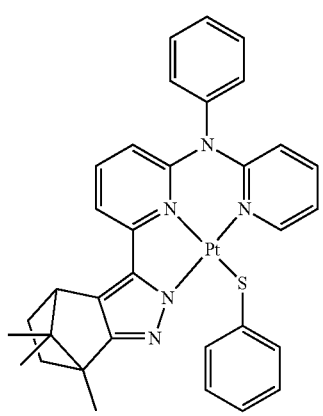
97
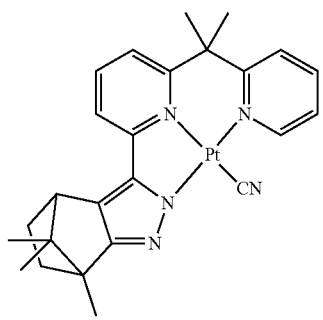
98
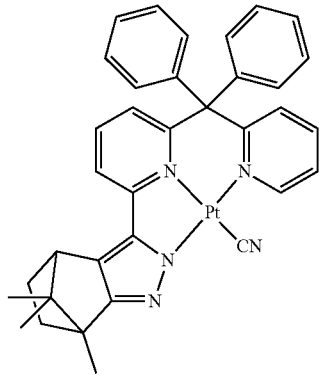

225
-continued
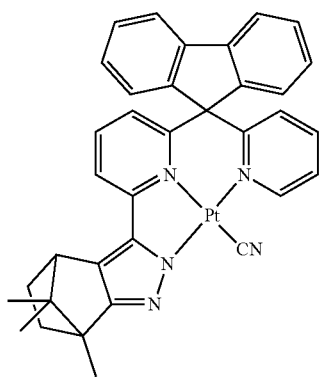
99
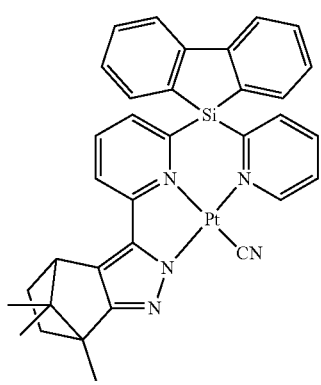
100
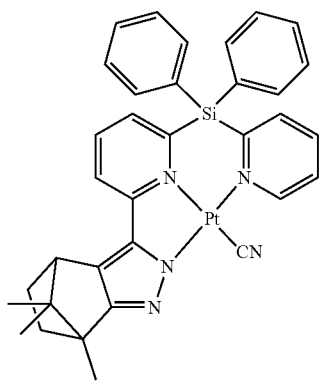
101
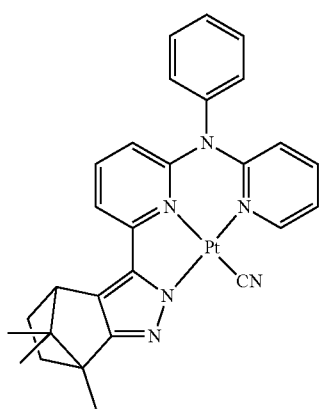
102
226
-continued
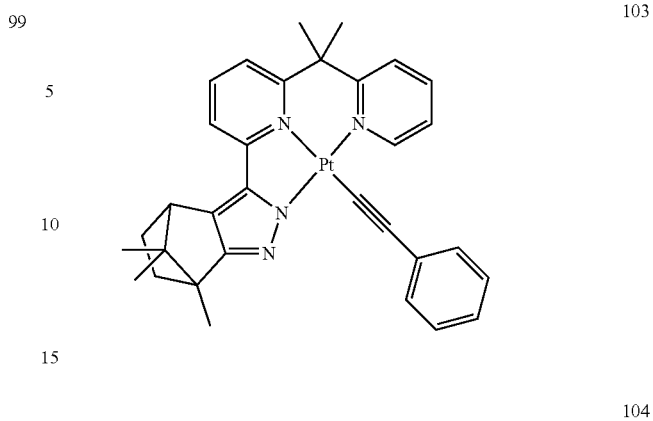
103
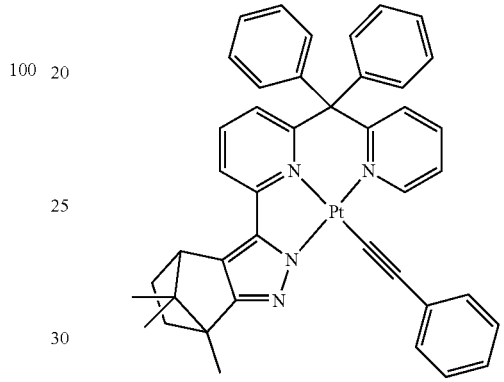
104
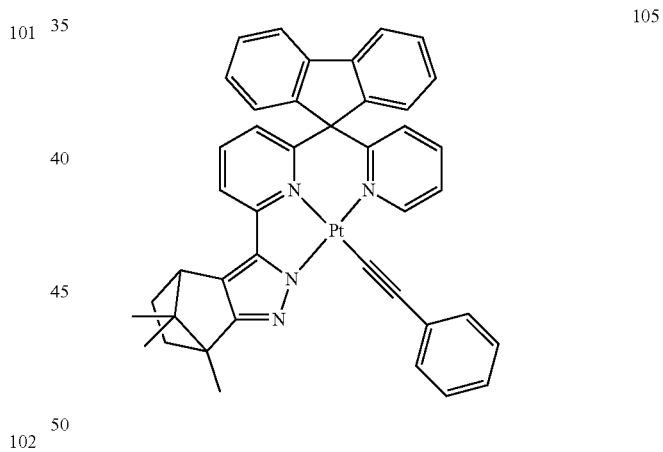
105
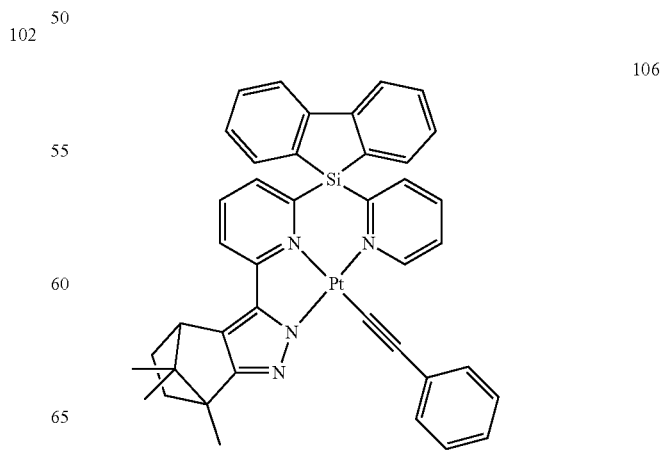
106

227
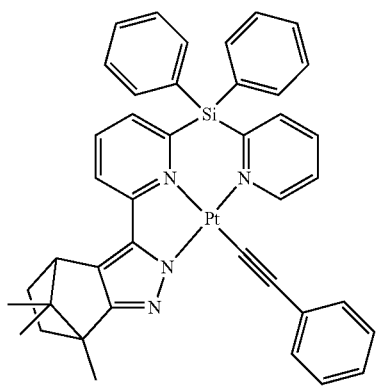
107
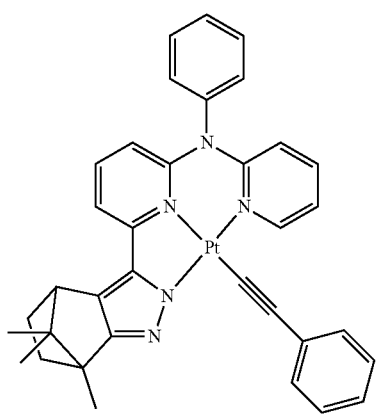
108
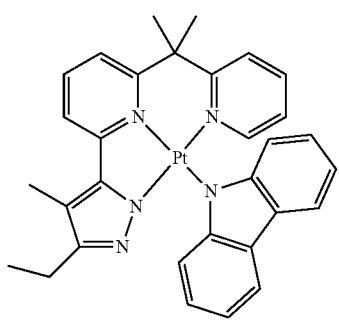
109
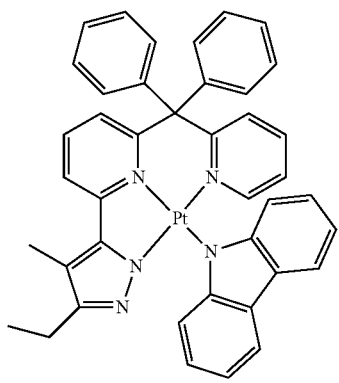
110
228
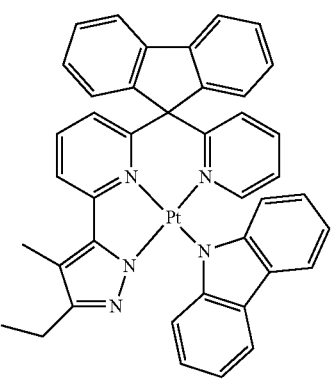
111
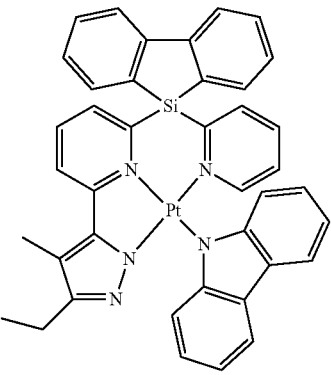
112
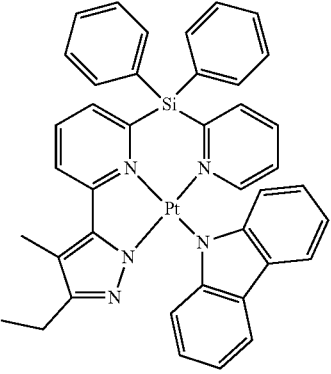
113
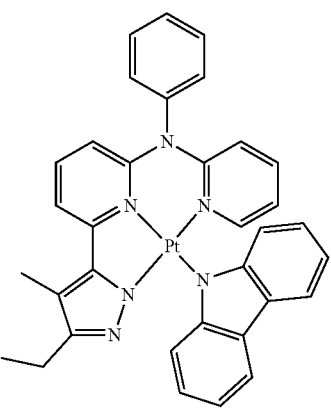
114

| 115 | 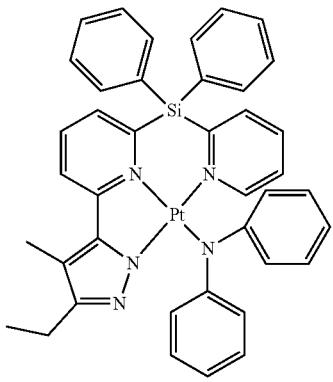 | 119 |
| 116 | 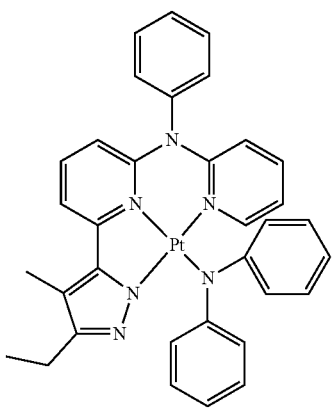 | 120 |
| 117 | 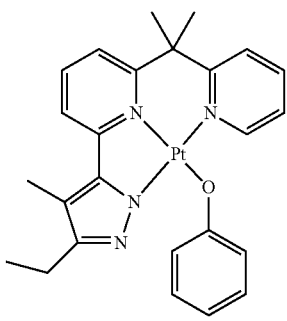 | 121 |
| 118 | 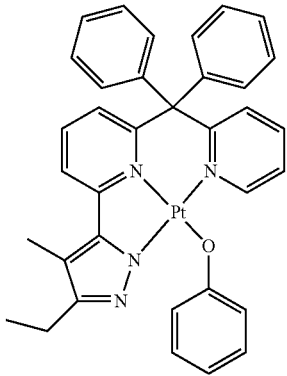 | 122 |
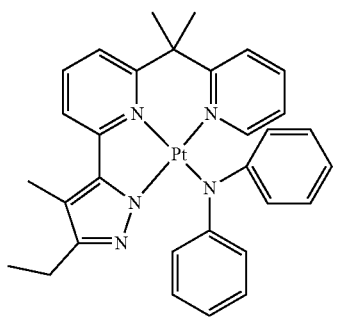
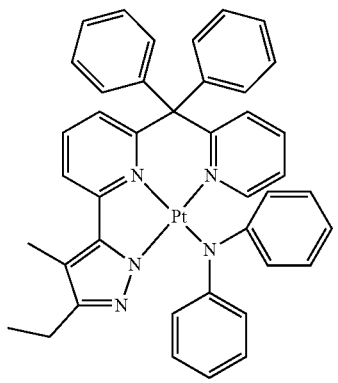
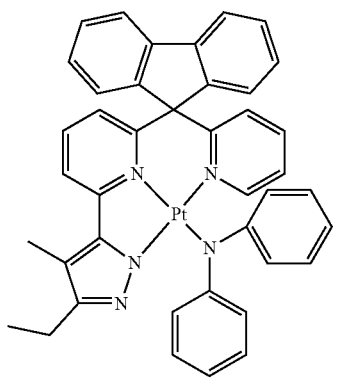
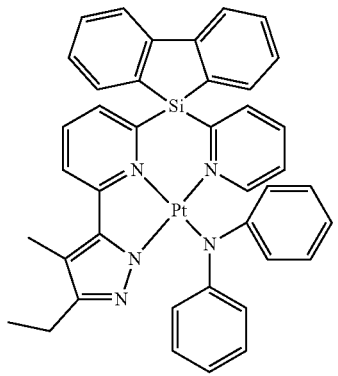

-continued
123
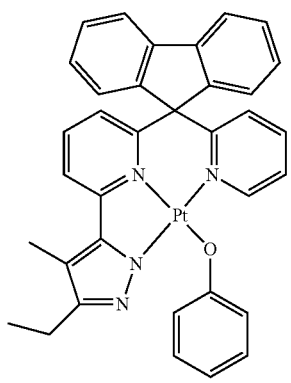
124
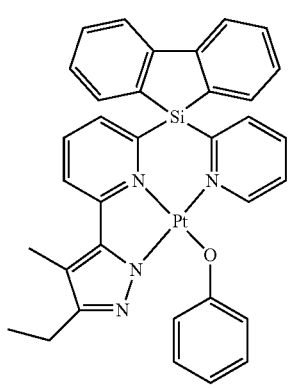
125
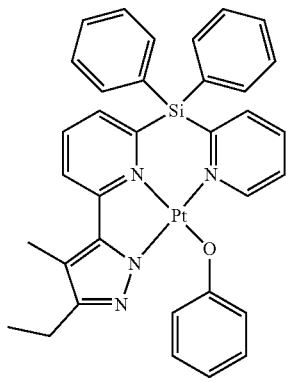
126
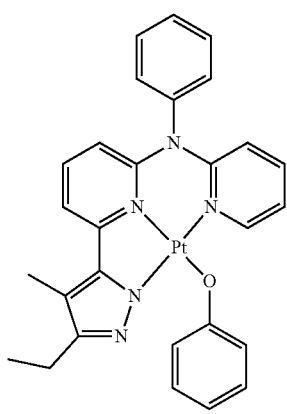
-continued
127
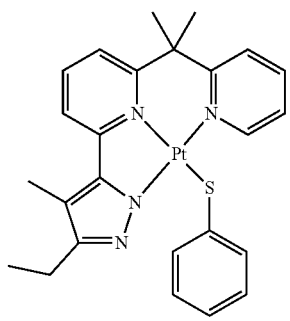
128
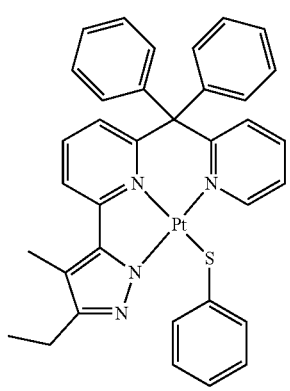
129
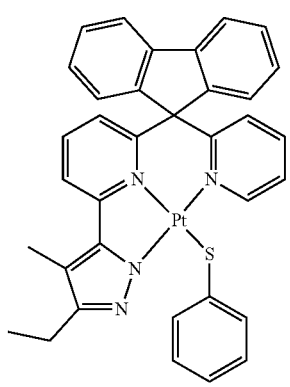
130
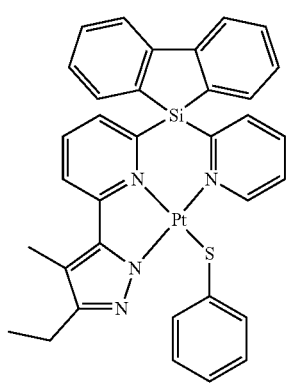

233
-continued
131 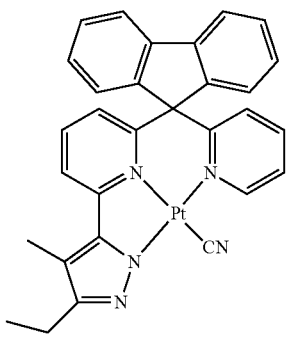
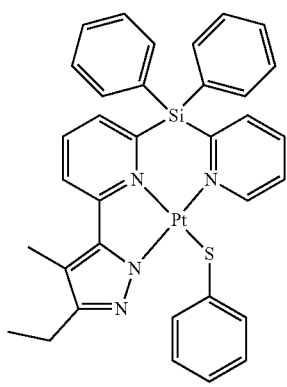
132
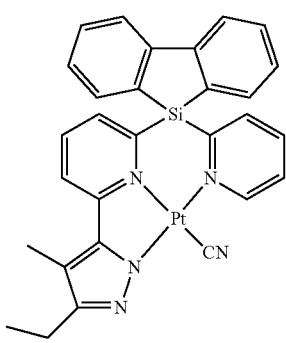
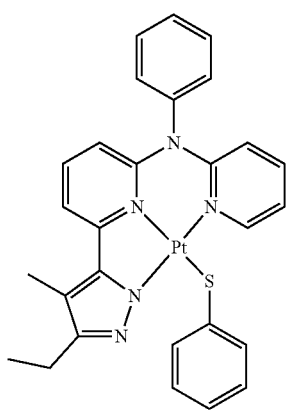
133
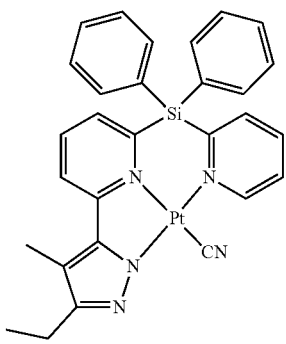
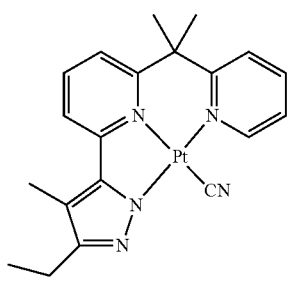
134
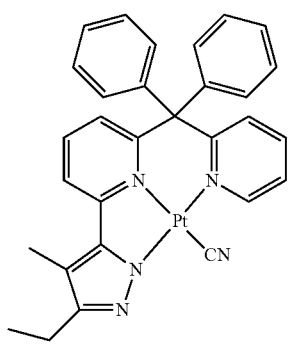
135
136
137
138 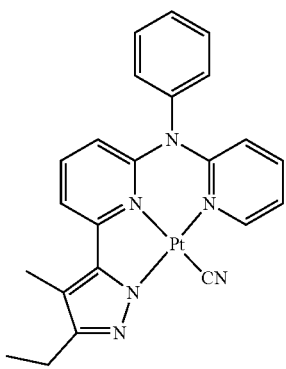

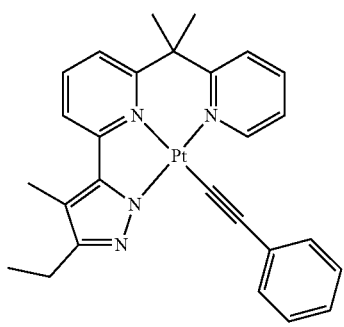
139
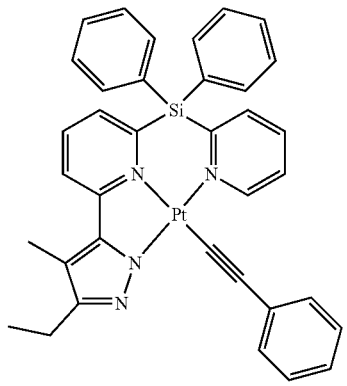
143
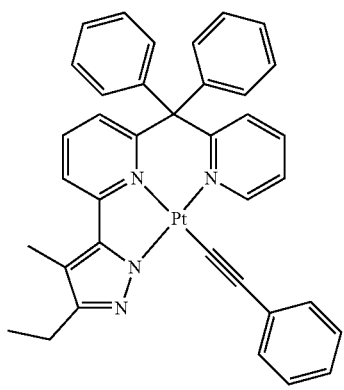
140
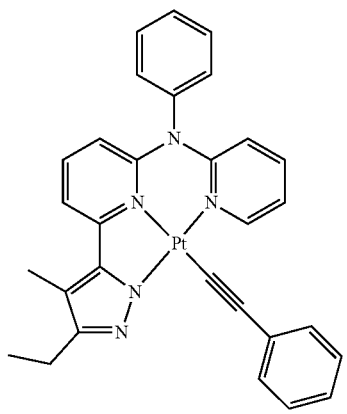
144
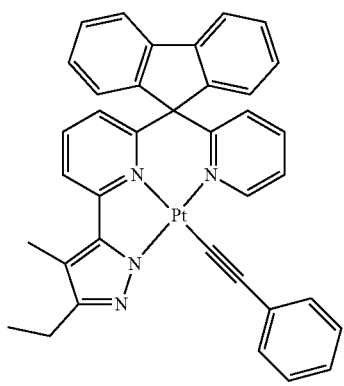
141
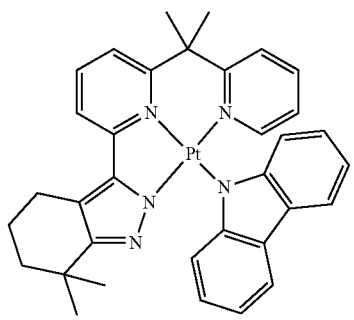
145
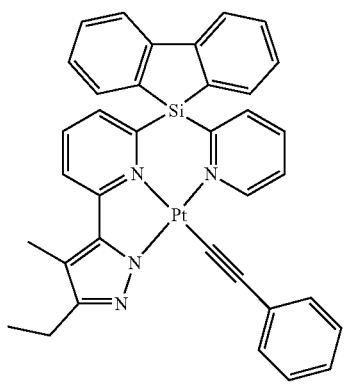
142
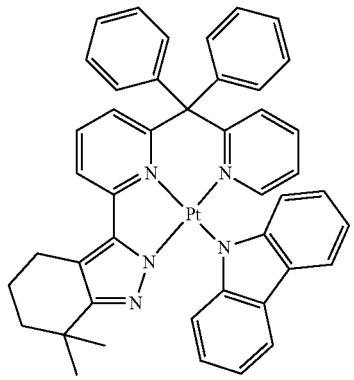
146

147
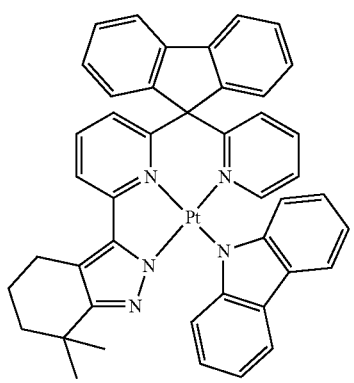
148
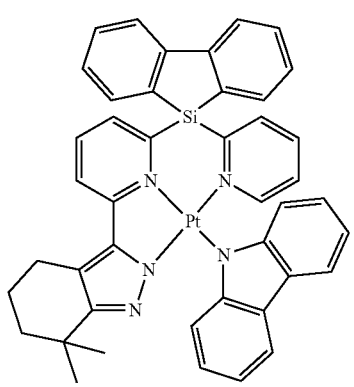
149
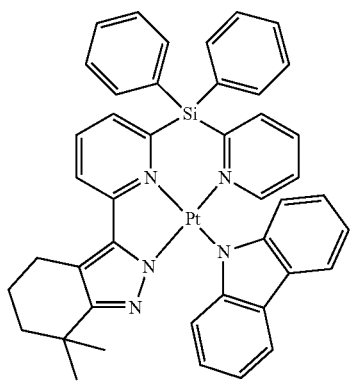
150
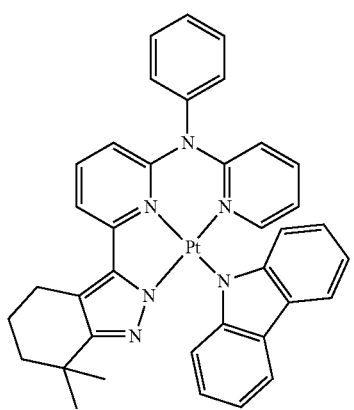
151
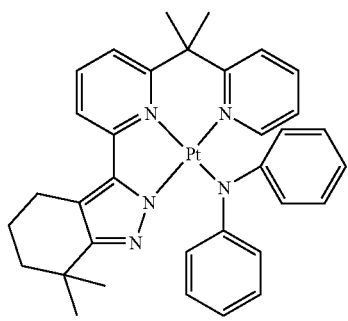
152
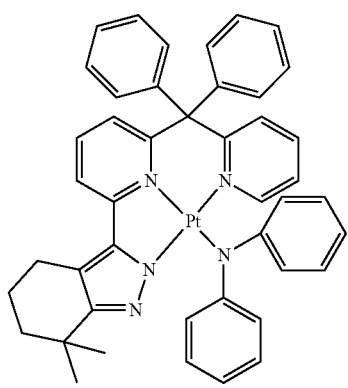
153
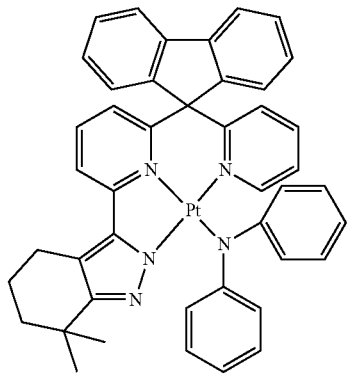
154

239
-continued
155
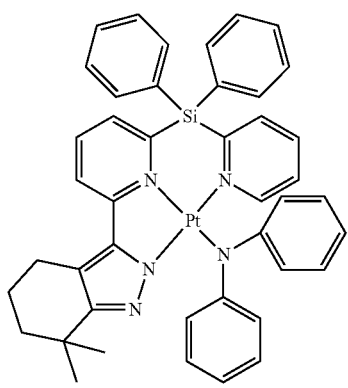
156
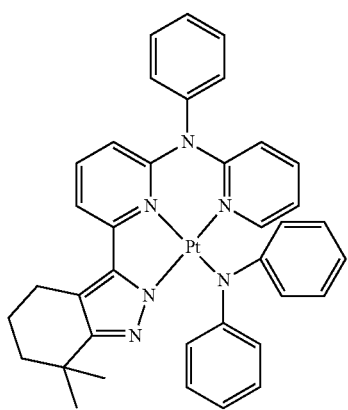
157
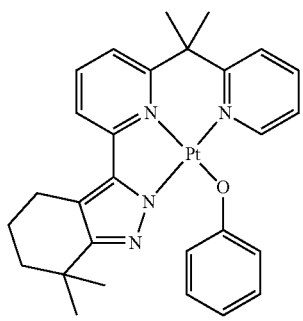
158
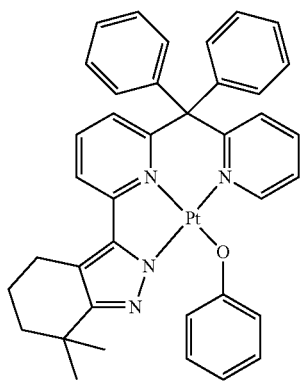
240
-continued
159
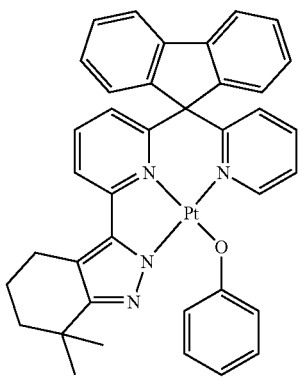
160
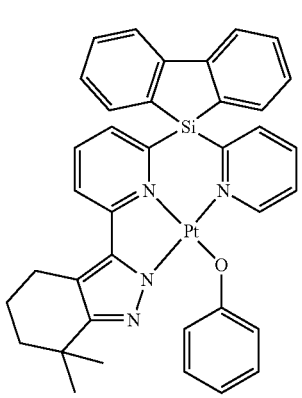
161
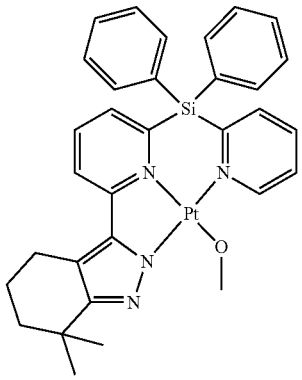
162
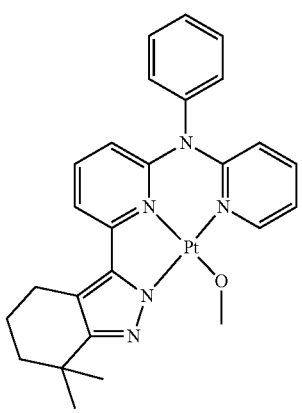

163
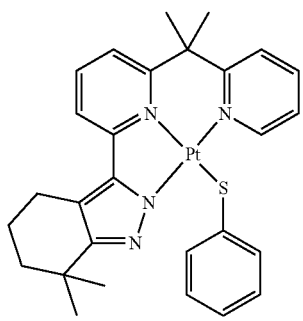
164
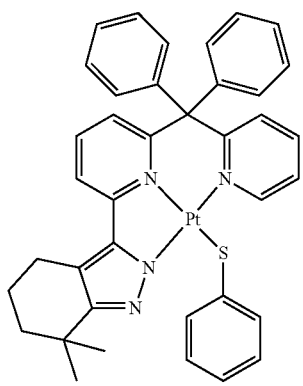
165
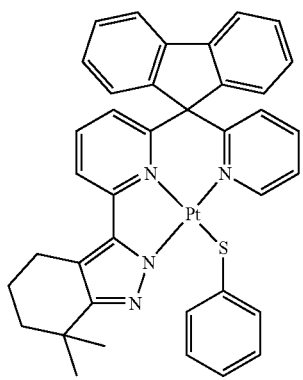
166
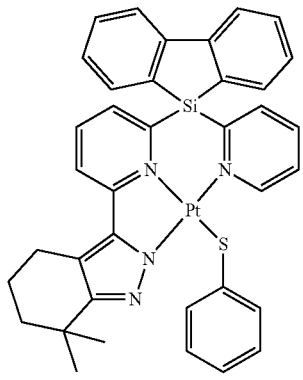
167
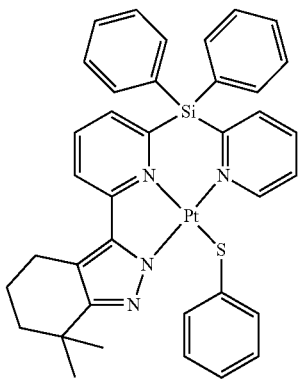
168
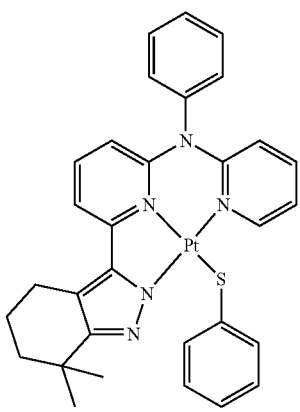
169
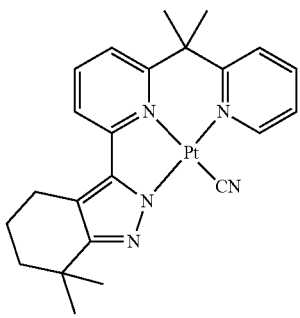
170
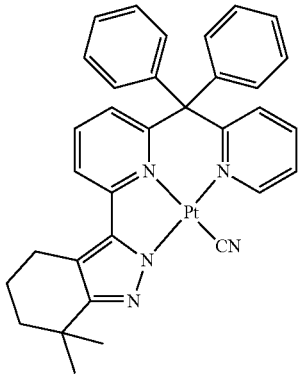

-continued
171
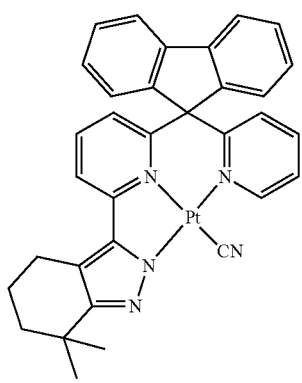
175
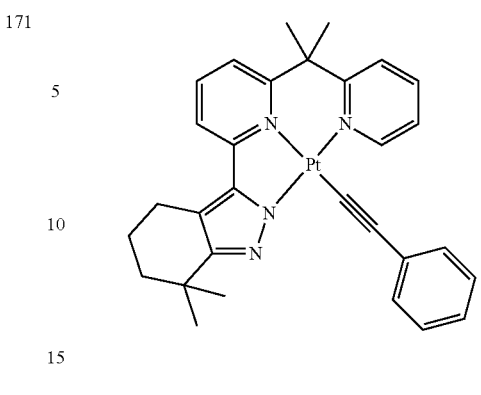
172
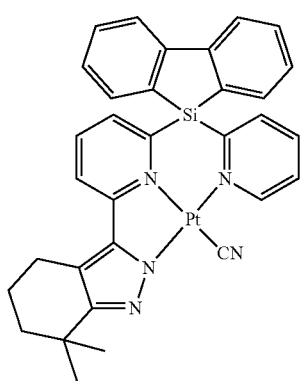
176
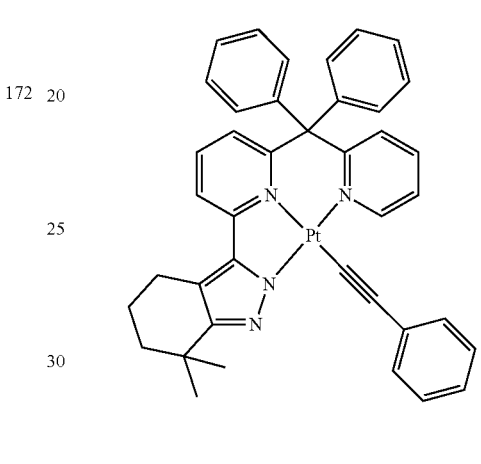
173
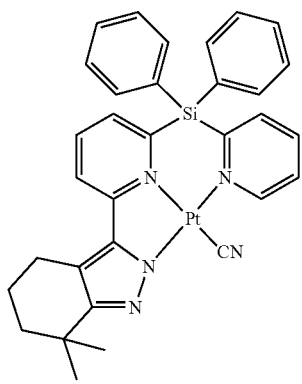
177
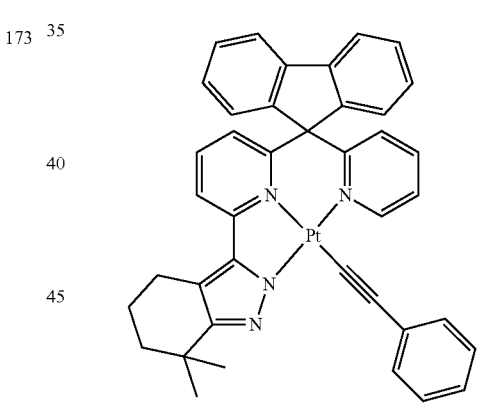
174
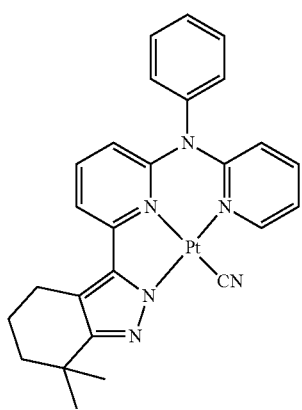
178
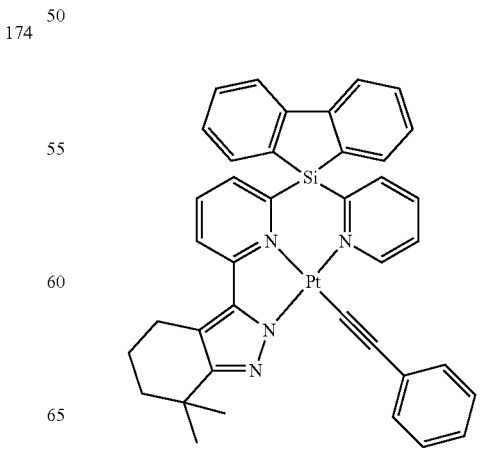

-continued

179

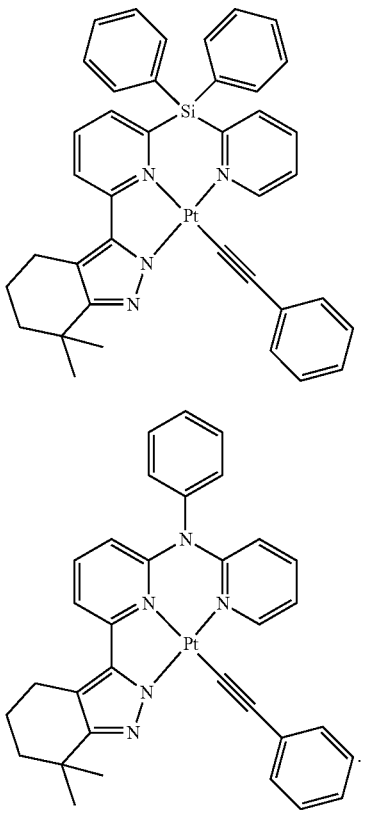

180

11. An organic light-emitting device comprising:
a first electrode;
a negative electrode; and
an organic layer disposed between the first electrode and the second electrode, wherein the organic layer comprises an emission layer and at least one organometallic compound of claim 1.

12. The organic light-emitting device of claim 11, wherein the emission layer comprises the organometallic compound.

13. A composition for diagnosing comprising at least one organometallic compound of claim 1.

14. An organometallic compound represented by Formula 1:

$$M(L_1)(L_2) \quad \text{Formula 1}$$

Formula 2

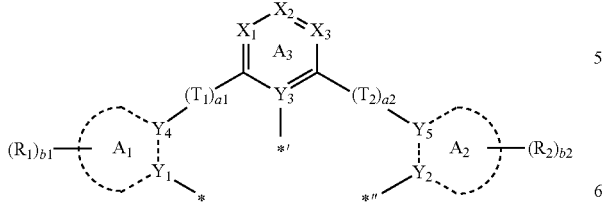

wherein, in Formulae 1 and 2,
M is beryllium, magnesium, aluminum, calcium, titanium, manganese, cobalt, copper, zinc, gallium, germanium, zirconium, ruthenium, rhodium, palladium, silver, rhenium, gold, or platinum, $L_1$ is selected from tridentate ligands represented by Formula 2,
$L_2$ is selected from monodentate organic ligands,
*, *', and *'' in Formula 2 each indicate a binding site to M in Formula 1,
$Y_1$ to $Y_3$ are each nitrogen,
$Y_4$ and $Y_5$ are each carbon,
$Y_1$ is bound to $Y_4$ via a single or double bond, $Y_2$ is bound to $Y_5$ via a single or double bond,
provided that one selected from a bond between $Y_1$ and M, a bond between $Y_2$ and M, and a bond between ligand $L_2$ and M is a coordinate bond, while the rest are each a covalent bond,
a bond between $Y_3$ and M is a coordinate bond,
ring $A_1$ is a 5-membered ring comprising at least one nitrogen as a ring-forming atom,
ring $A_2$ is a 6-membered ring comprising at least one nitrogen as a ring-forming atom,
$X_1$ is N or $C(R_3)$, $X_2$ is N or $C(R_4)$, $X_3$ is N or $C(R_5)$, at least two selected from $R_3$ to $R_5$ are optionally bound to each other to form a substituted or unsubstituted $C_5$-$C_{30}$ carbocyclic group or a substituted or unsubstituted $C_2$-$C_{30}$ heterocyclic group,
$T_1$ is a group selected from a single bond, *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom,
$T_2$ is a group selected from *—O—*', *—S—*', *—C($R_6$)($R_7$)—*', *—C($R_6$)=*', *=C($R_6$)—*', *—C($R_6$)=C($R_7$)—*', *—C(=O)—*', *—C(=S)—*', *—C≡C—*', *—N($R_6$)—*', *—Si($R_6$)($R_7$)—*', and *—P($R_6$)($R_7$)—*', wherein * and *' in each of the foregoing groups independently indicate a binding site to a neighboring atom,
$R_6$ and $R_7$ are optionally bound to each other to form a substituted or unsubstituted $C_5$-$C_{30}$ carbocyclic group or a substituted or unsubstituted $C_2$-$C_{30}$ heterocyclic group,
a1 and a2 are each independently an integer selected from 1 to 3, $R_1$ to $R_7$ are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), b1 and b2 are each independently an integer selected from 0 to 3, and when b1 is 2 or greater, groups $R_1$ are identical to or different from each other, and when b2 is 2 or greater, groups $R_2$ are identical to or different from each other, two of the b1 number of groups $R_1$ are optionally bound to each other to form a substituted or unsubstituted $C_5$-$C_{30}$ carbocyclic group or a substituted or unsubstituted $C_2$-$C_{30}$ heterocyclic group, two of the b2 number of groups $R_2$ are optionally bound to each other to form a substituted or unsubstituted $C_5$-$C_{30}$ carbocyclic group or a substituted or unsubstituted $C_2$-$C_{30}$ heterocyclic group, provided that, i) $T_2$ is a group selected from *—$C(R_6)(R_7)$—*' and *—$Si(R_6)(R_7)$—*' and $R_6$ and $R_7$ are bound to each other to form a substituted or unsubstituted $C_5$-$C_{30}$ carbocyclic group or a substituted or unsubstituted $C_2$-$C_{30}$ heterocyclic group, ii) $L_2$ is a monodentate organic ligand represented by Formula 13-47 or iii) $T_2$ is a group selected from *—$C(R_6)(R_7)$—*' and *—$Si(R_6)(R_7)$—*' and $R_6$ and $R_7$ are bound to each other to form a substituted or unsubstituted $C_5$-$C_{30}$ carbocyclic group or a substituted or unsubstituted $C_2$-$C_{30}$ heterocyclic group; and $L_2$ is a monodentate organic ligand represented by Formula 13-47,

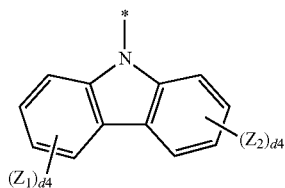

Formula 13-47 wherein, in Formulae 13-47, $Z_1$ and $Z_2$ are each independently selected from hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

d4 is an integer selected from 1 to 4,

* indicates a binding site to M in Formula 1, at least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

\* \* \* \* \*